US011883201B2

(12) United States Patent
Just et al.

(10) Patent No.: US 11,883,201 B2
(45) Date of Patent: *Jan. 30, 2024

(54) PHYSIOLOGICAL MONITORING DEVICES WITH ADJUSTABLE STABILITY

(71) Applicant: YUKKA MAGIC LLC, Wilmington, DE (US)

(72) Inventors: Steven Matthew Just, Cary, NC (US); Steven Francis LeBoeuf, Raleigh, NC (US); Jesse Berkley Tucker, Youngsville, NC (US); Michael Edward Aumer, Raleigh, NC (US); Mark Andrew Felice, Cary, NC (US)

(73) Assignee: YUKKA MAGIC LLC, Wilmington, DE (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/487,849

(22) Filed: Sep. 28, 2021

(65) Prior Publication Data

US 2022/0015707 A1 Jan. 20, 2022

Related U.S. Application Data

(63) Continuation of application No. 15/318,449, filed as application No. PCT/US2015/042636 on Jul. 29, 2015, now Pat. No. 11,129,572.

(Continued)

(51) Int. Cl.
*A61B 5/00* (2006.01)
*A61B 5/11* (2006.01)
*A61B 5/0205* (2006.01)
*A61B 5/021* (2006.01)
*A61B 5/024* (2006.01)
*A61B 5/08* (2006.01)

(52) U.S. Cl.
CPC ........ *A61B 5/6844* (2013.01); *A61B 5/02055* (2013.01); *A61B 5/1118* (2013.01);
(Continued)

(58) Field of Classification Search
CPC ... A61B 5/6838; A61B 5/6843; A61B 5/6816; A61B 5/6826; A61B 5/681; A61B 5/6844
See application file for complete search history.

(56) References Cited

U.S. PATENT DOCUMENTS 3,412,729 A 11/1968 Smith
4,331,154 A 5/1982 Broadwater et al.
(Continued)

FOREIGN PATENT DOCUMENTS

JP 2008279061 A 11/2008
WO 2013093923 A2 6/2013

OTHER PUBLICATIONS

"Communication with European Search Report", EP Application No. 21189243.5, dated Jan. 14, 2022, 10 pp.
(Continued)

*Primary Examiner* — Lynsey C Eiseman
*Assistant Examiner* — Amanda L. Steinberg
(74) *Attorney, Agent, or Firm* — Brownstein Hyatt Farber Schreck, LLP

(57) ABSTRACT

A monitoring device configured to be attached to a body of a subject includes a physiological sensor configured to detect and/or measure physiological information from the subject, an activity sensor configured to sense physical activity information from the subject, an actuator configured to adjust stability of the monitoring device relative to the body of the subject, and a processor in communication with the activity sensor and the actuator. The processor is configured to process the physical activity information to detect a change in the physical activity of the subject and to control the at least one actuator to adjust the stability of the monitoring device relative to the body of the subject in response to detecting that a change in the physical activity of the subject has occurred.

18 Claims, 38 Drawing Sheets

Related U.S. Application Data

(60) Provisional application No. 62/110,784, filed on Feb. 2, 2015, provisional application No. 62/031,019, filed on Jul. 30, 2014.

(52) U.S. Cl.
CPC ............ *A61B 5/681* (2013.01); *A61B 5/6816* (2013.01); *A61B 5/6826* (2013.01); *A61B 5/6838* (2013.01); *A61B 5/6843* (2013.01); *A61B 5/021* (2013.01); *A61B 5/0205* (2013.01); *A61B 5/02438* (2013.01); *A61B 5/0816* (2013.01); *A61B 5/4266* (2013.01); *A61B 2560/0242* (2013.01)

(56) References Cited

U.S. PATENT DOCUMENTS

| | | |
|---|---|---|
| 4,413,620 A | 11/1983 | Tucker |
| 5,485,848 A | 1/1996 | Jackson et al. |
| 6,491,647 B1 | 12/2002 | Bridger et al. |
| 7,620,450 B2 | 11/2009 | Kim et al. |
| 9,254,088 B2 | 2/2016 | Park et al. |
| 2007/0244399 A1 | 10/2007 | Kim et al. |
| 2008/0167572 A1 | 7/2008 | Stivoric et al. |
| 2008/0194917 A1 | 8/2008 | Muehlsteff et al. |
| 2009/0253996 A1 | 10/2009 | Lee et al. |
| 2010/0234714 A1 | 9/2010 | Mercier et al. |
| 2012/0150086 A1* | 6/2012 | Cohen ................... A61F 5/0104 602/27 |
| 2013/0053661 A1 | 2/2013 | Alberth et al. |
| 2014/0070042 A1 | 3/2014 | Beers et al. |
| 2016/0287108 A1 | 10/2016 | Wei et al. |
| 2017/0034615 A1 | 2/2017 | Mankodi et al. |

OTHER PUBLICATIONS

"Extended European Search Report corresponding to European Application No. 15827029.8 dated Jun. 14, 2017".

"International Search Report and Written Opinion, PCT/US2015/042636, dated Oct. 29, 2015, 10 pages".

* cited by examiner

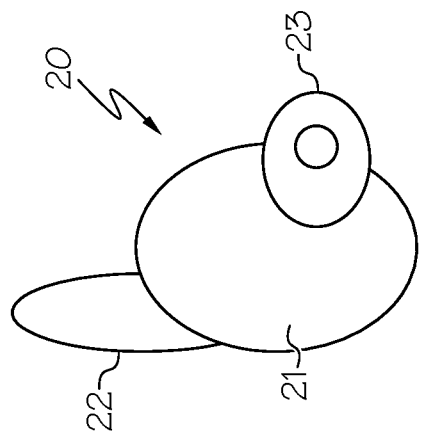
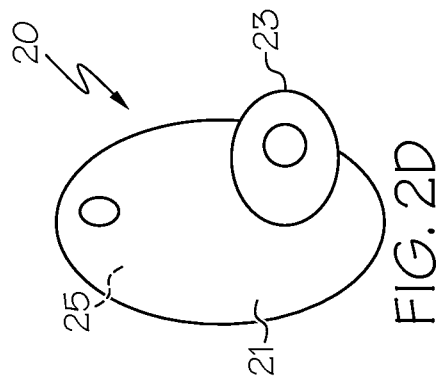
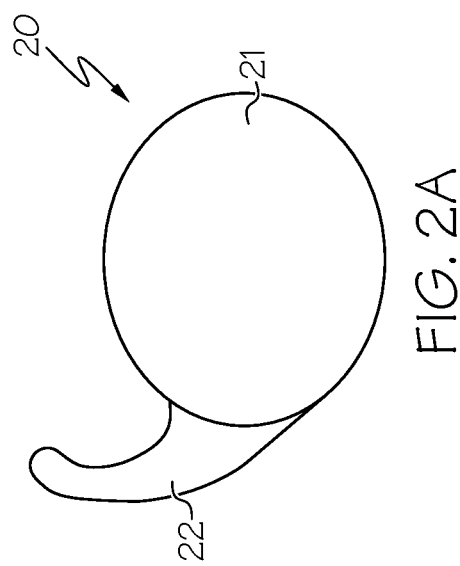
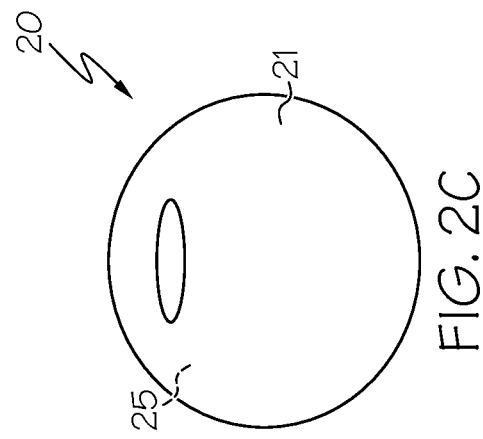

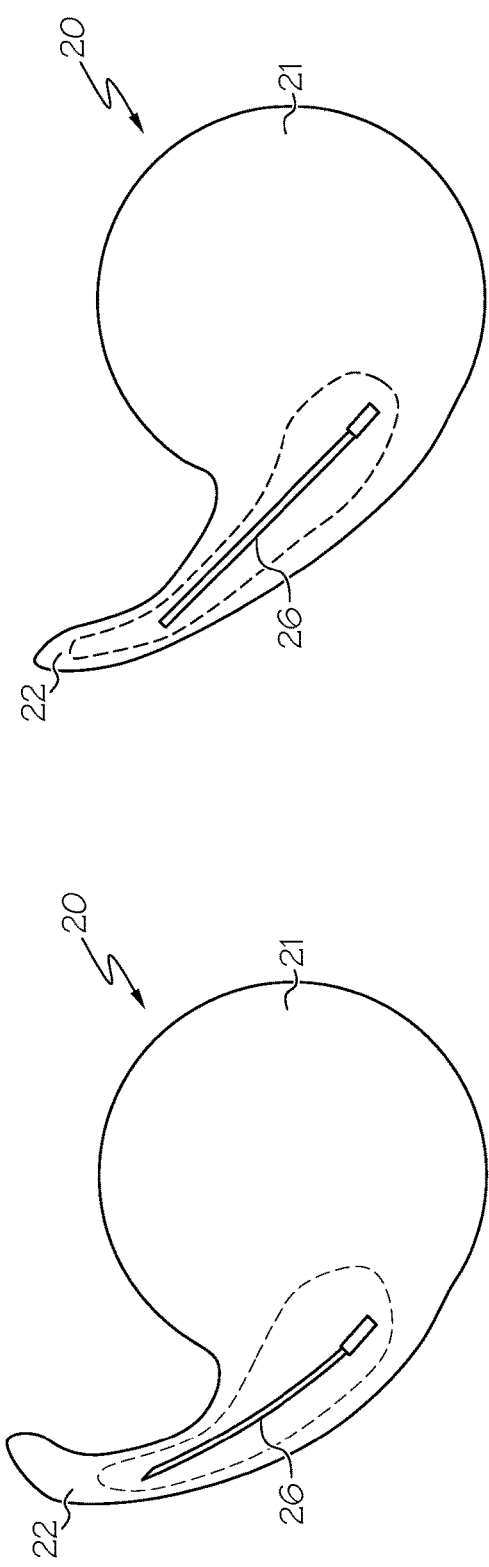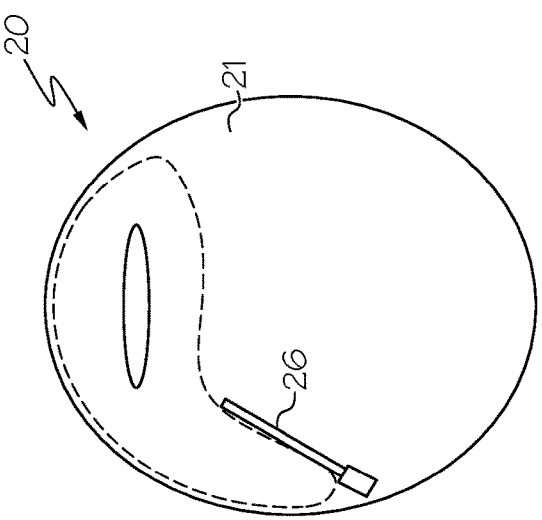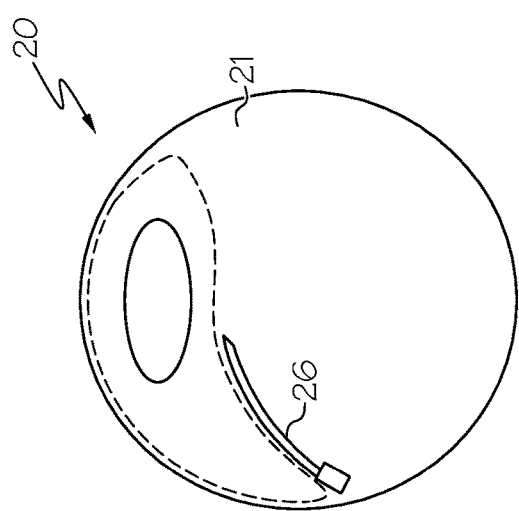

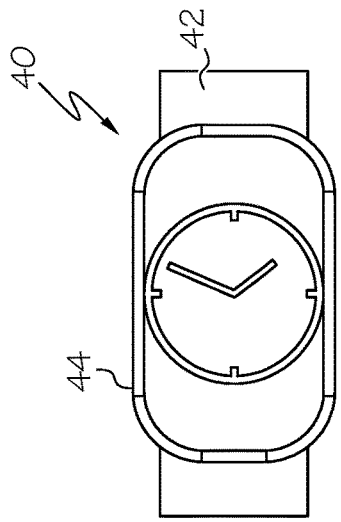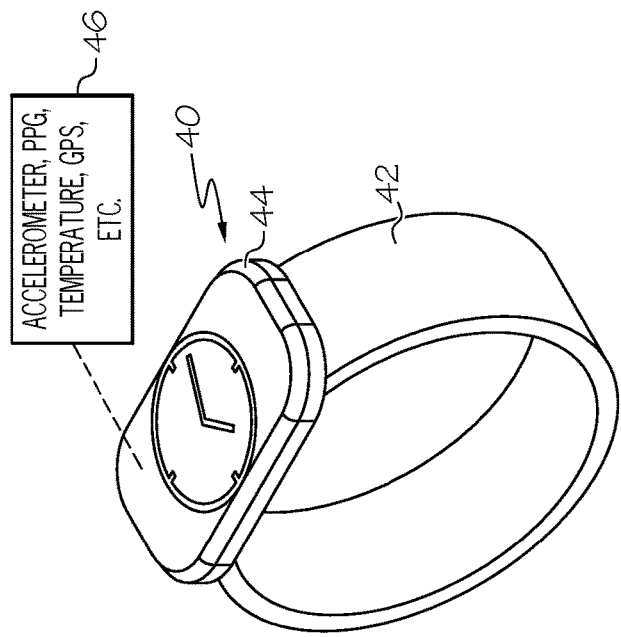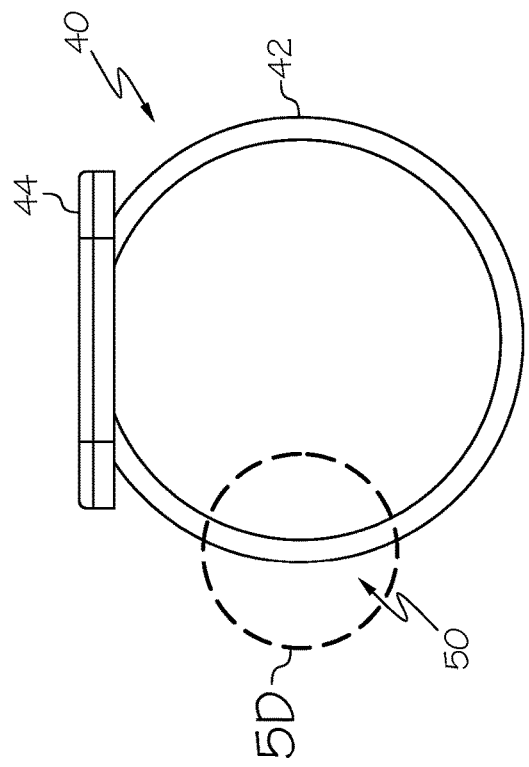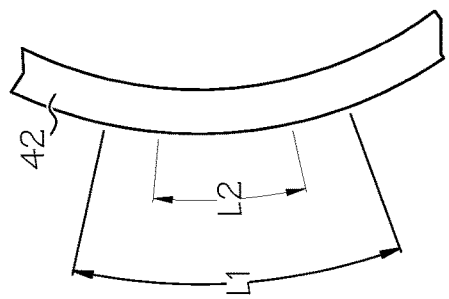

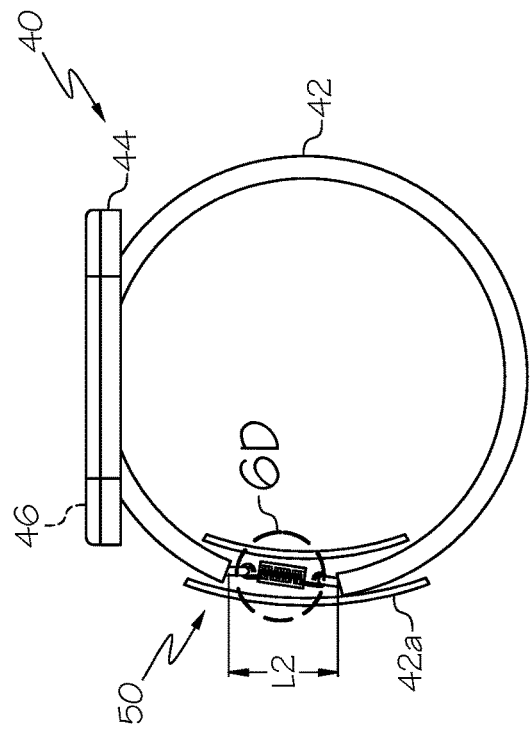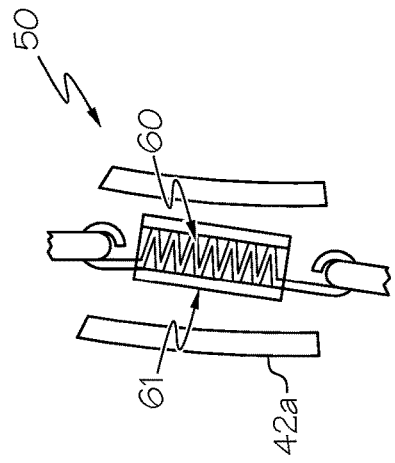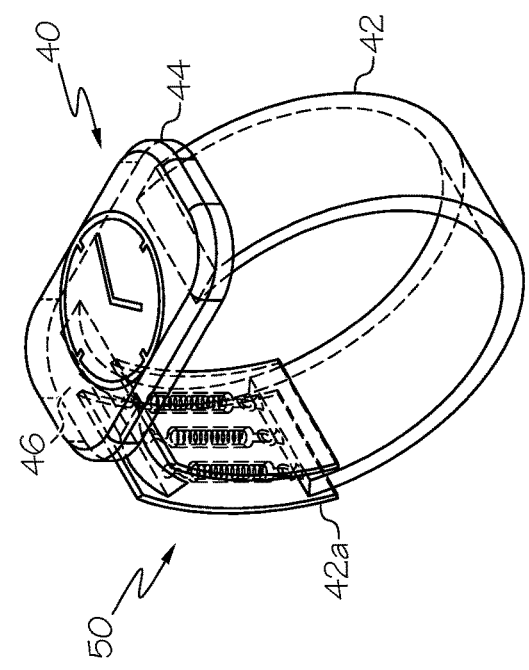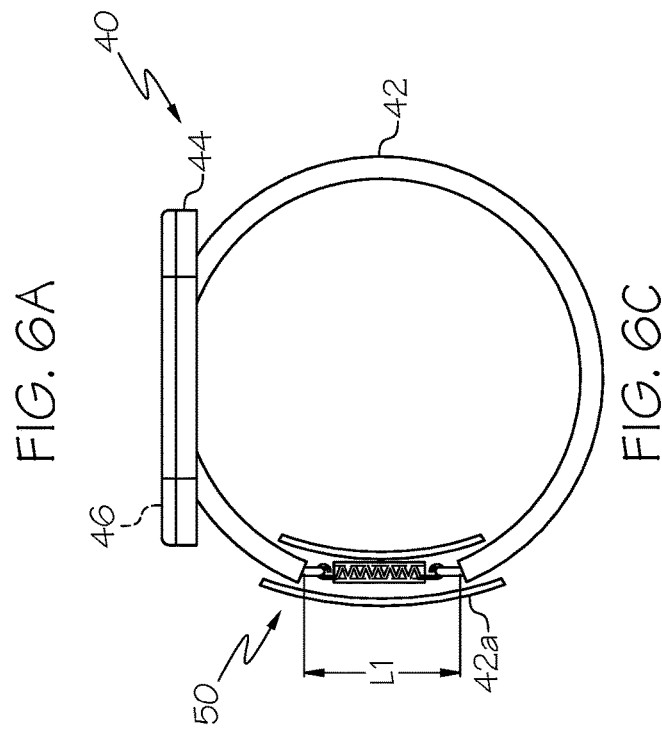
FIG. 6A
FIG. 6B
FIG. 6C
FIG. 6D

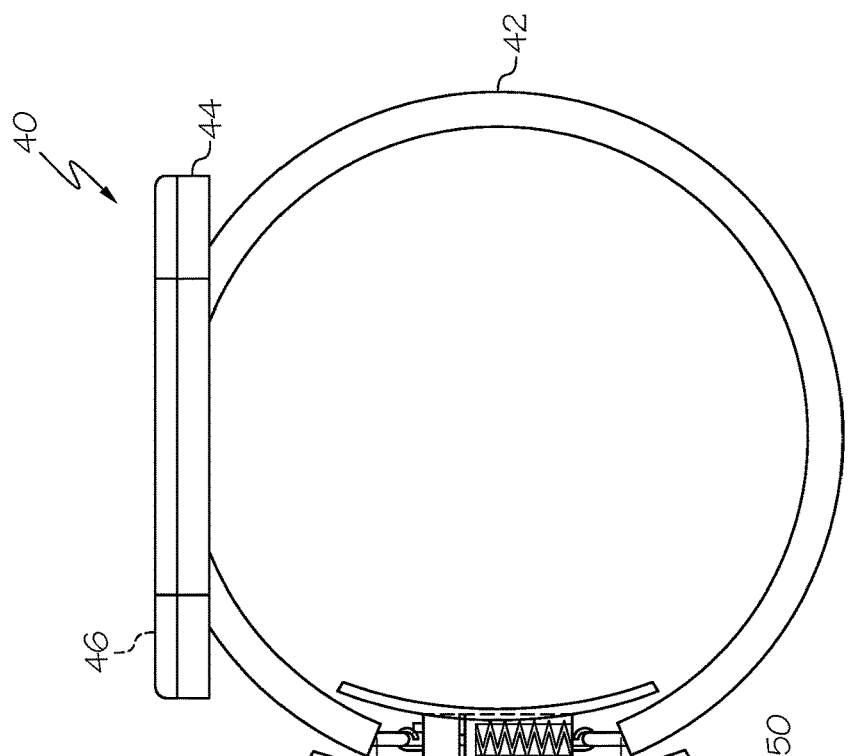
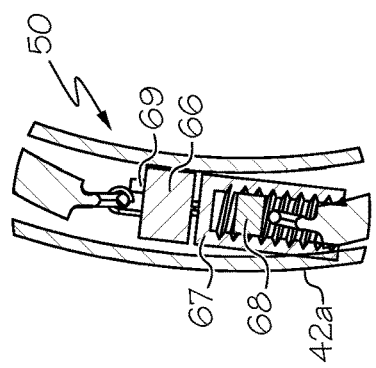
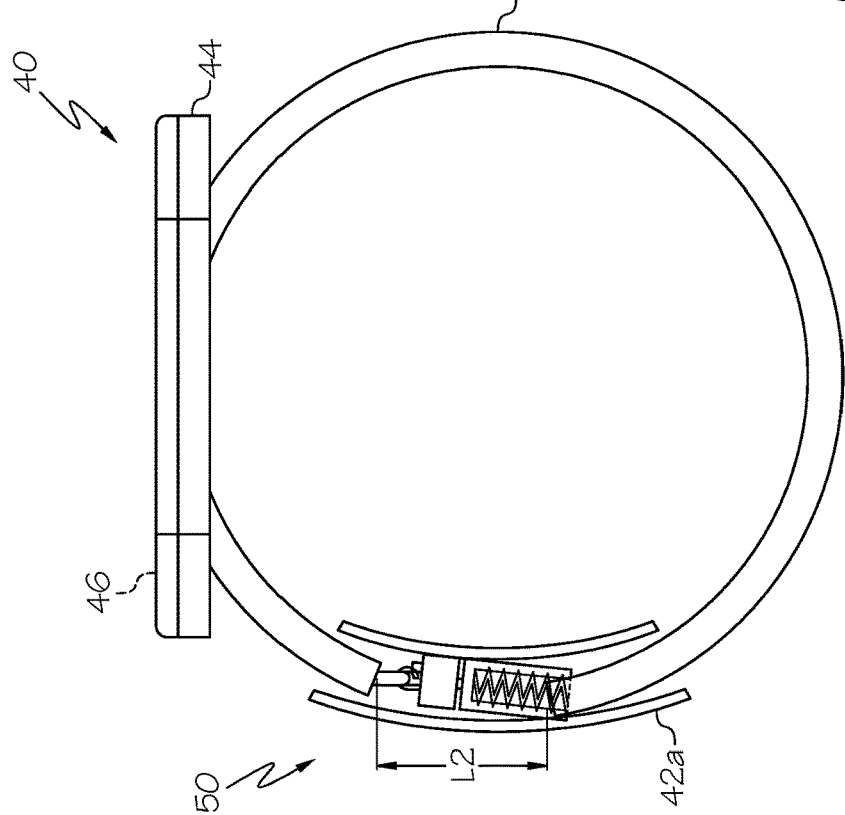
FIG. 8D
FIG. 8E
FIG. 8C

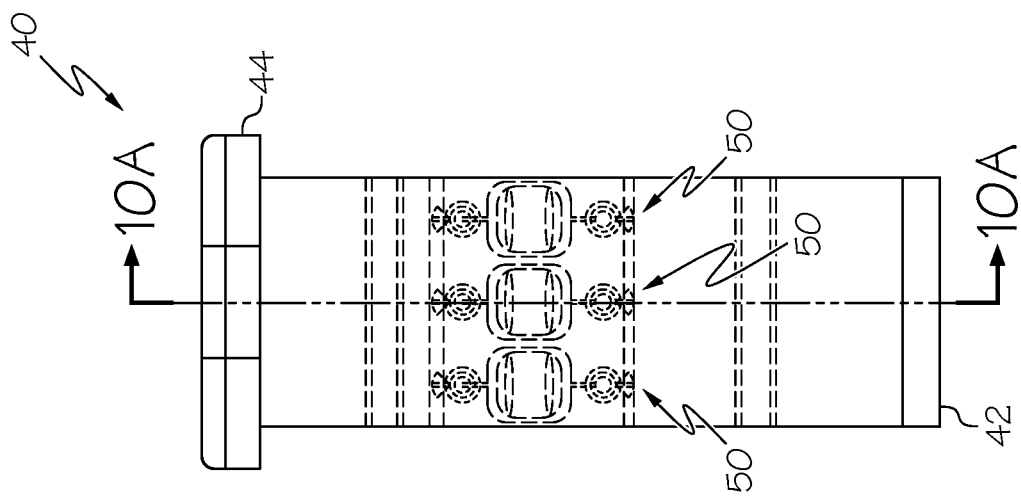
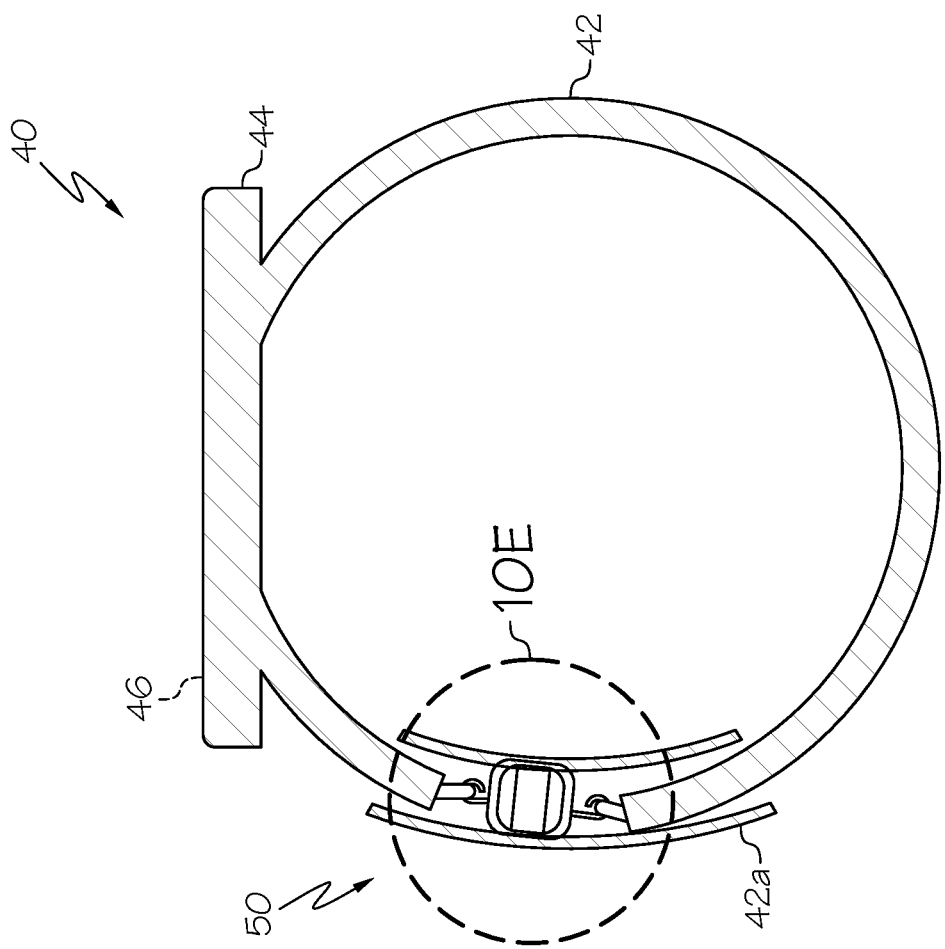

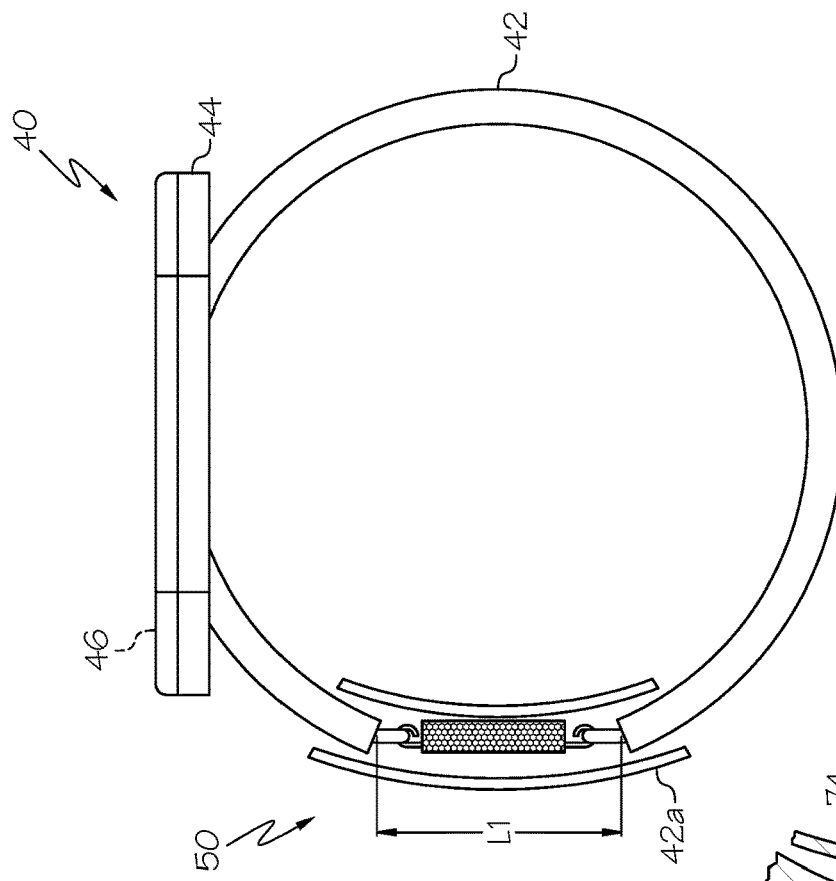
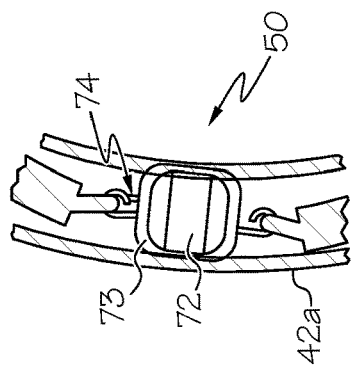
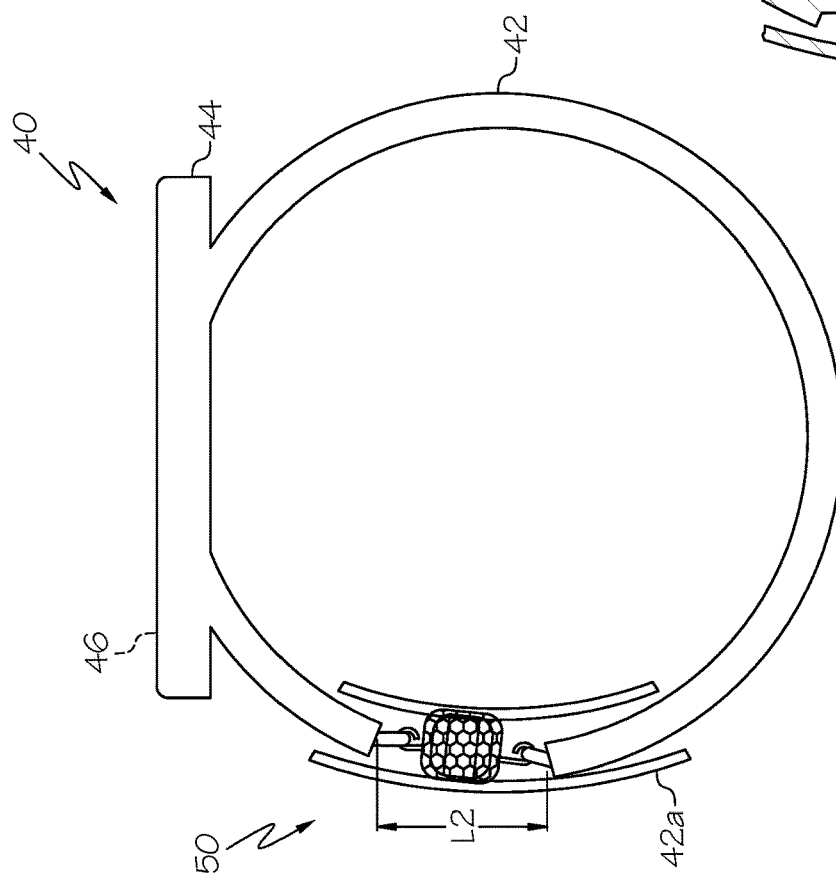

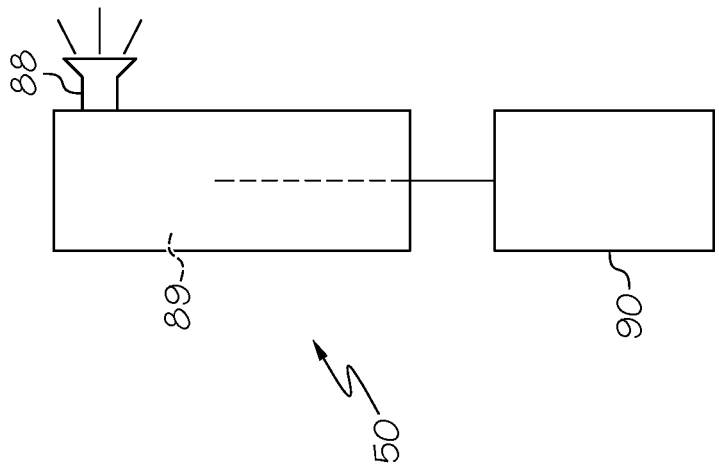
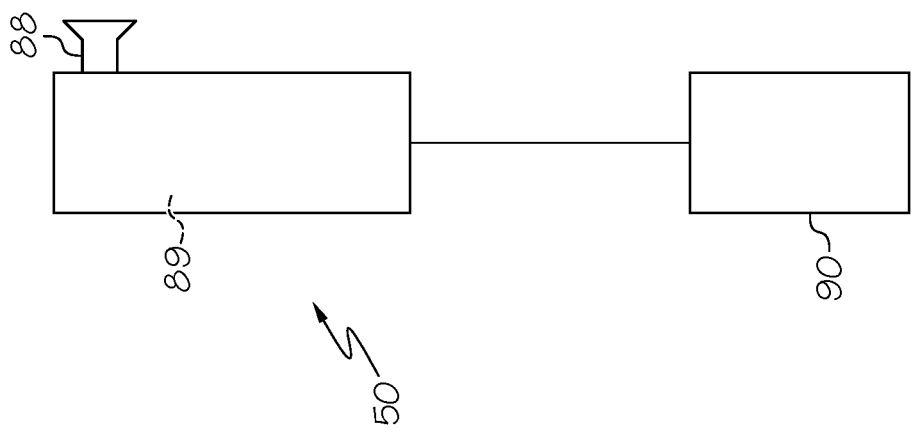

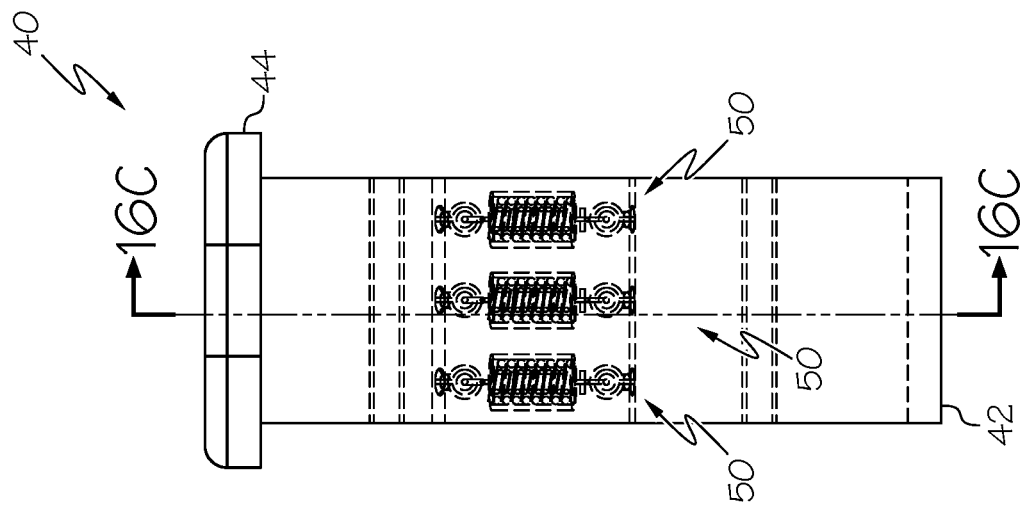
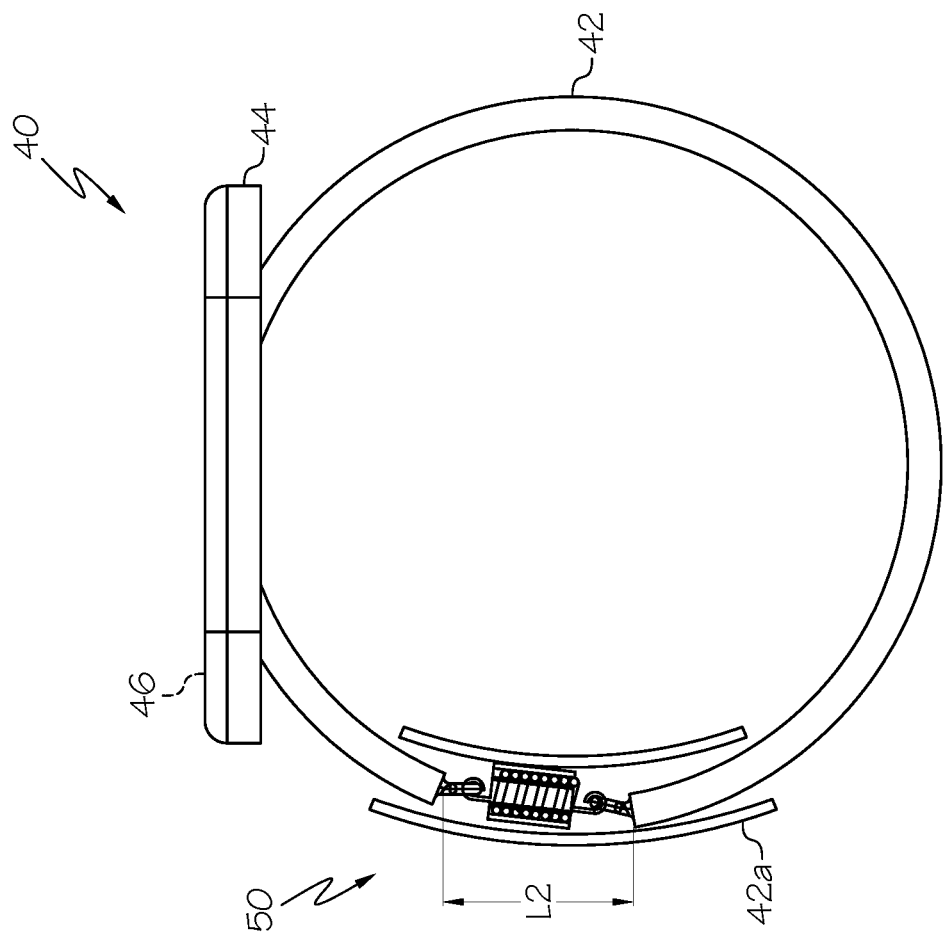
FIG. 16B
FIG. 16A

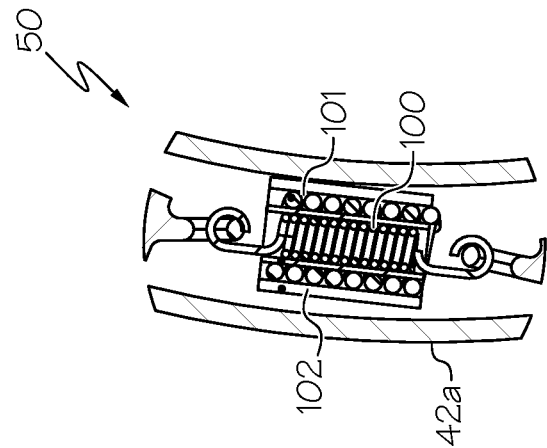
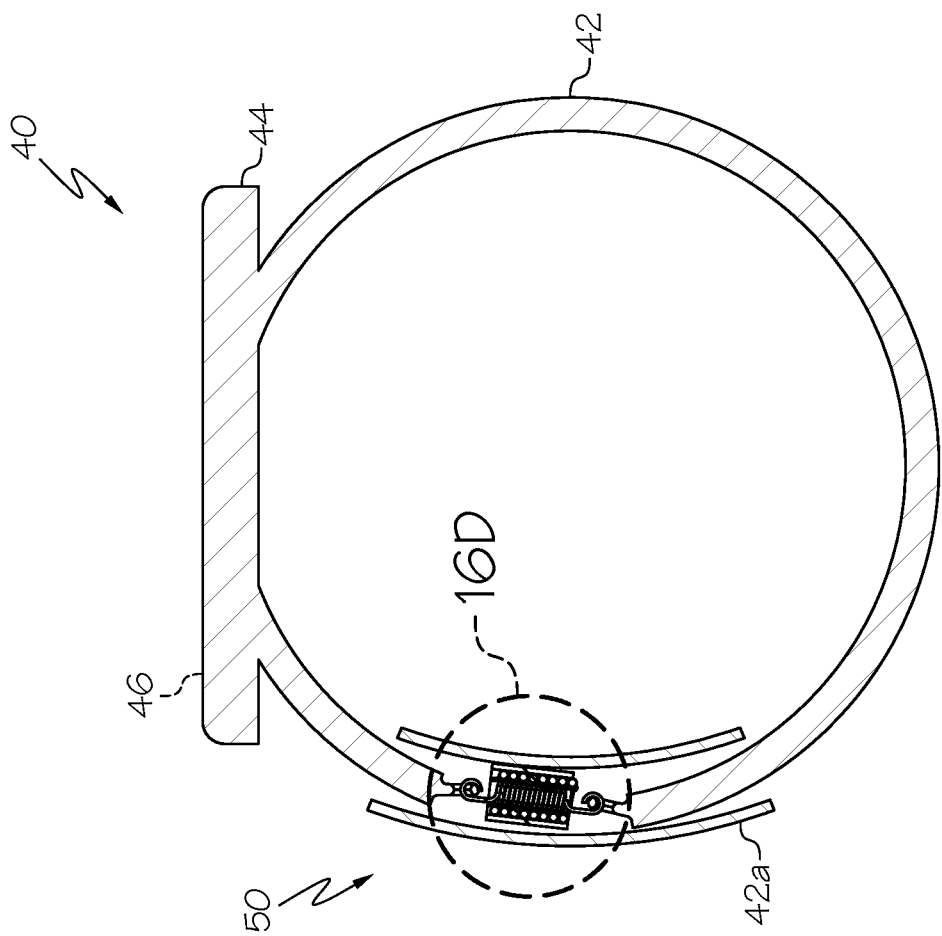

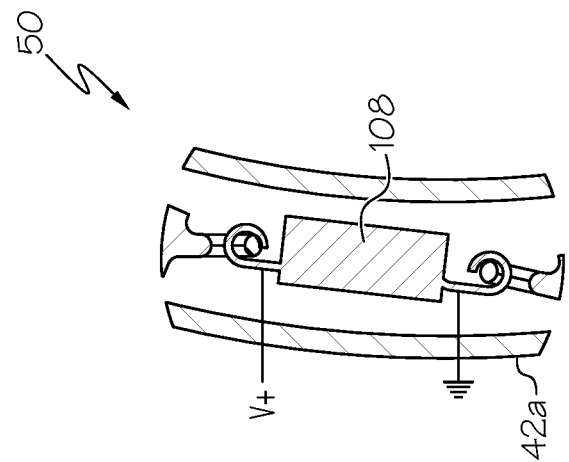
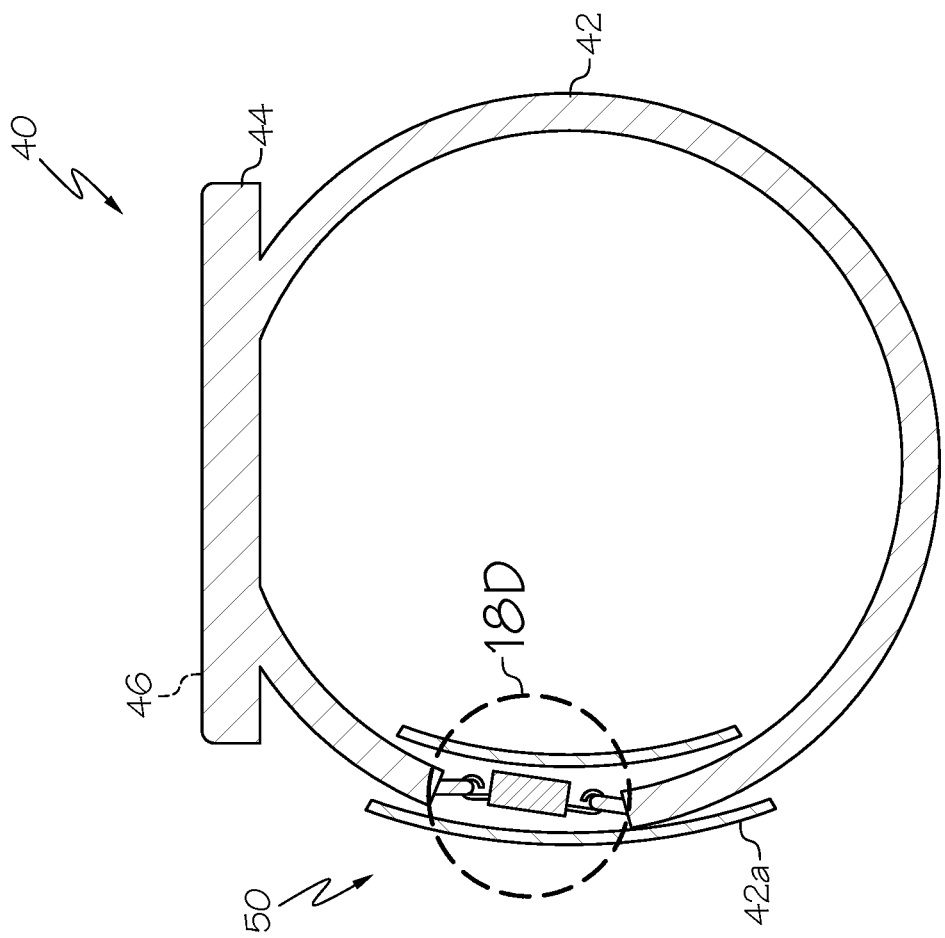

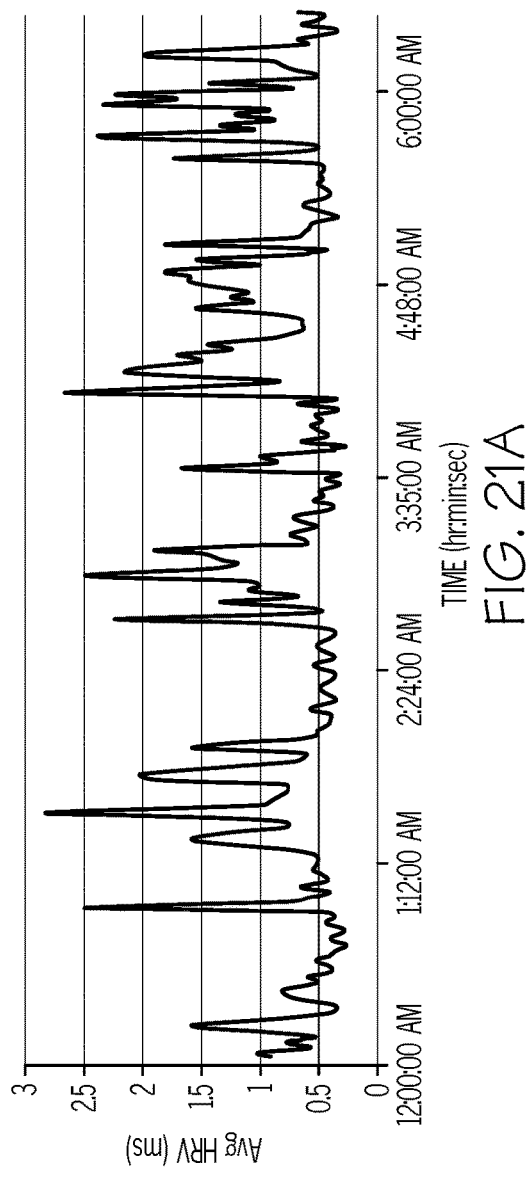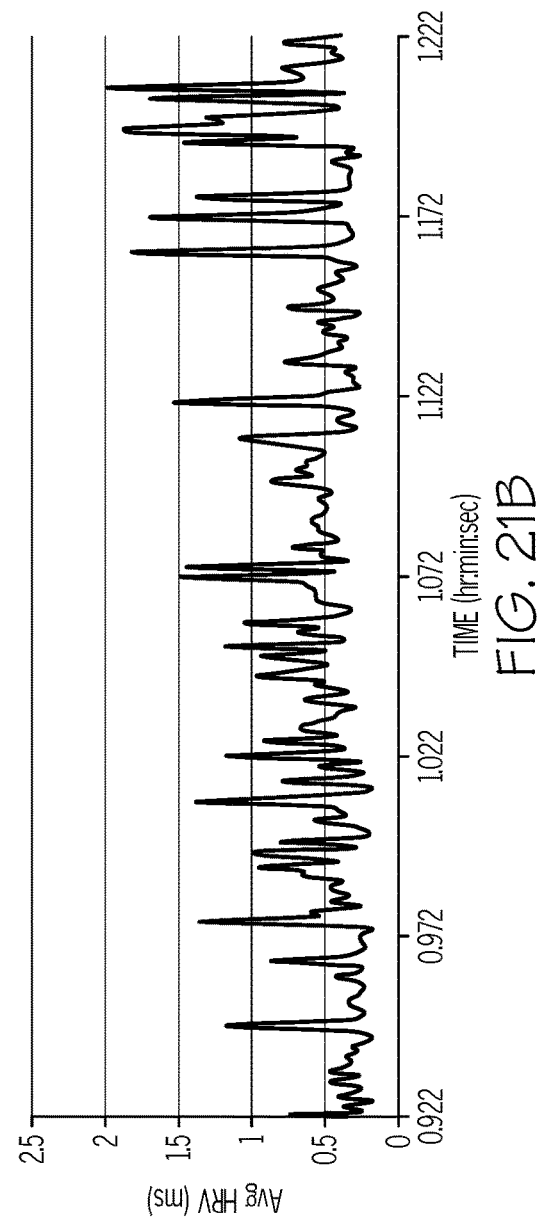

PHYSIOLOGICAL MONITORING DEVICES WITH ADJUSTABLE STABILITY

RELATED APPLICATIONS

This application is a continuation application of pending U.S. patent application Ser. No. 15/318,449, filed Dec. 13, 2016, which is a 35 U.S.C. § 371 national stage application of PCT Application No. PCT/US2015/042636, filed on Jul. 29, 2015, which claims the benefit of and priority to U.S. Provisional Patent Application No. 62/031,019 filed Jul. 30, 2014, and U.S. Provisional Patent Application No. 62/110,784 filed Feb. 2, 2015, the disclosures of which are incorporated herein by reference as if set forth in their entireties. The above-referenced PCT International Application was published in the English language as International Publication No. WO 2016/019002 on Feb. 4, 2016.

FIELD OF THE INVENTION

The present invention relates generally to monitoring devices and, more particularly, to monitoring devices for measuring physiological information.

BACKGROUND OF THE INVENTION

Photoplethysmography (PPG) is based upon shining light into the human body and measuring how the scattered light intensity changes with each pulse of blood flow. The scattered light intensity will change in time with respect to changes in blood flow or blood opacity associated with heart beats, breaths, blood oxygen level ($SpO_2$), and the like. Such a sensing methodology may require the magnitude of light energy reaching the volume of flesh being interrogated to be steady and consistent so that small changes in the quantity of scattered photons can be attributed to varying blood flow. If the incidental and scattered photon count magnitude changes due to light coupling variation between the source or detector and the skin or other body tissue, then the signal of interest can be difficult to ascertain due to large photon count variability caused by motion artifacts. Changes in the surface area (and volume) of skin or other body tissue being impacted with photons, or varying skin surface curvature reflecting significant portions of the photons may also significantly impact optical coupling efficiency. Physical activity, such a walking, cycling, running, etc., may cause motion artifacts in the optical scatter signal from the body, and time-varying changes in photon intensity due to motion artifacts may swamp-out time-varying changes in photon intensity due to blood flow changes. Each of these changes in optical coupling can dramatically reduce the signal-to-noise ratio (S/N) of biometric PPG information to total time-varying photonic interrogation count. This can result in a much lower accuracy in metrics derived from PPG data, such as heart rate and breathing rate.

An earphone, such as a headset, earbud, etc., may be a good choice for incorporation of a photoplethysmograph device because it is a form factor that individuals may be familiar with, it is a device that may be commonly worn for long periods of time, and it frequently may be used during exercise which is a time when individuals may benefit most from having accurate heart rate data (or other physiological data). Unfortunately, incorporation of a photoplethysmograph device into an earphone poses several challenges. For example, earphones may be uncomfortable to wear for long periods of time, particularly if they deform the ear surface. Moreover, human ear anatomy may vary significantly from person to person, so finding an earbud form that will fit comfortably in many ears may pose significant challenges. In addition, earbuds made for vigorous physical activity typically incorporate an elastomeric surface and/or elastomeric features to function as springs that dampen earbud acceleration within the ear. Although, these features may facilitate retention of an earbud within an ear during high acceleration and impact modalities, they may not adequately address optical skin coupling requirements needed to achieve quality photoplethysmography.

Conventional photoplethysmography devices, as illustrated for example in FIGS. 1A-1C, typically suffer from reduced skin coupling as a result of subject motion. For example, most conventional photoplethysmography devices use a spring to clip the sensor onto either an earlobe (FIG. 1A) or a fingertip (FIG. 1B). Unfortunately, these conventional devices tend to have a large mass and may not maintain consistent skin contact when subjected to large accelerations, such as when a subject is exercising.

A conventional earbud device that performs photoplethysmography in the ear is the MX-D100 player from Perception Digital of Wanchai, Hong Kong (www.perceptiondigital.com). This earbud device, illustrated in FIG. 1C and indicated as 10, incorporates a spring biased member 12 to improve PPG signal quality. The member 12 is urged in the direction of the arrow $A_1$ by an internal spring (not shown) as indicated in FIG. 1C. However, the spring biased member 12 forcibly presses the entire earbud 10 within the ear E of a subject to minimize motion of the entire earbud 10. There are several drawbacks to the device 10 of FIG. 1C. For example, the source/sensor module is coupled to the entire earbud mass and, as such, may experience larger translation distances resulting in greater signal variability when the ear undergoes accelerations as a result of body motion of a person wearing the device. In addition, because the earbud 10 is held in place with one primary spring force direction, significant discomfort can be experienced by the end user. Moreover, the earbud motion is only constrained in one direction (i.e., the direction indicated by $A_1$) due to the single spring force direction.

Because PPG used in wearable devices employs an optical technology, requiring the powering of optical emitters and microprocessors via a wearable battery, managing power consumption can be challenging. For example, high-power algorithms may be required to accurately measure heart rate during exercise. Thus, employing a high-power algorithm during exercise may have the benefit of accurately monitoring heart rate during exercise but may also have the unwanted effect of draining the battery of the wearable device such that the device will not have enough power to measure a subject over the course of a day or week during non-exercising periods.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a monitoring device configured to be attached to a body of a subject includes a sensor that is configured to detect and/or measure physiological information from the subject, and at least one actuator that is configured to adjust the stability of the monitoring device relative to the subject body in response to the sensor detecting a change in subject activity. The sensor may be an optical sensor that includes at least one optical emitter and at least one optical detector, although various other types of sensors may be utilized. The at least one actuator is configured to increase the stability or tension of the monitoring device relative to the subject body in response to detecting an increase in subject activity, and is configured to decrease the stability or tension of the monitoring device relative to the subject body in response to detecting a decrease in subject activity. In some embodiments, detecting a change in subject activity includes detecting a change in at least one subject vital sign, such as subject heart rate, subject blood pressure, subject temperature, subject respiration rate, and/or subject perspiration rate etc. In other embodiments, the sensor includes a motion sensor, such as an accelerometer, gyroscope, etc., and detecting a change in subject activity includes detecting a change in subject motion via the motion sensor.

According to some embodiments of the present invention, a method of monitoring a subject via a monitoring device includes changing the stability/tension of the monitoring device relative to the subject body in response to detecting a change in subject activity. In some embodiments, changing the stability of the monitoring device relative to the subject body in response to detecting a change in subject activity includes increasing the stability of the monitoring device relative to the subject body in response to detecting an increase in subject activity, and decreasing the stability of the monitoring device relative to the subject body in response to detecting a decrease in subject activity. In some embodiments, detecting a change in subject activity includes detecting a change in at least one subject vital sign, such as subject heart rate, subject blood pressure, subject temperature, subject respiration rate, subject perspiration rate, etc. In other embodiments, the monitoring device includes a motion sensor, and detecting a change in subject activity comprises detecting a change in subject motion via the motion sensor.

According to other embodiments of the present invention, a monitoring device that is configured to be attached to a subject includes a sensor that is configured to detect and/or measure physiological information from the subject and to detect and/or measure at least one environmental condition in a vicinity of the subject. The sensor may be an optical sensor that includes at least one optical emitter and at least one optical detector, although various other types of sensors may be utilized. The monitoring device includes at least one actuator that is configured to change the stability/tension of the monitoring device relative to the subject body in response to the sensor detecting a change in the at least one environmental condition. Exemplary changes in environmental conditions include changes in one or more of the following ambient conditions: temperature, humidity, air quality, barometric pressure, radiation, light intensity, and sound.

According to some embodiments of the present invention, a method of monitoring a subject via a monitoring device includes changing the stability/tension of the monitoring device relative to the subject body in response to detecting a change in the at least one environmental condition. In some embodiments, changing the stability of the monitoring device relative to the subject body in response to detecting a change in the at least one environmental condition includes increasing the stability of the monitoring device relative to the subject body in response to detecting an increase in the at least one environmental condition, and decreasing the stability of the monitoring device relative to the subject body in response to detecting a decrease in the at least one environmental condition.

According to other embodiments of the present invention, a monitoring device that is configured to be attached to a subject includes a clock (e.g., a digital clock, an internal software clock, etc.), and a sensor configured to detect and/or measure physiological information from the subject. The sensor may be an optical sensor that includes at least one optical emitter and at least one optical detector, although various other types of sensors may be utilized. The monitoring device includes at least one actuator that is configured to change the stability/tension of the monitoring device relative to the subject body at one or more predetermined times. For example, the at least one actuator may be configured to increase the stability/tension of the monitoring device relative to the subject body at one or more predetermined times and decrease the stability of the monitoring device relative to the subject body at one or more other predetermined times.

In some embodiments, the at least one actuator is configured to increase the stability of the monitoring device relative to the subject body according to a schedule of when the sensor is to detect and/or measure physiological information from the subject.

In some embodiments, the at least one actuator is configured to increase the stability of the monitoring device relative to the subject body according to the circadian rhythm of the subject.

According to some embodiments, a method of monitoring a subject via a monitoring device includes changing the stability/tension of the monitoring device relative to the subject body at one or more predetermined times. For example, in some embodiments, changing the stability of a monitoring device relative to the subject body at one or more predetermined times includes increasing the stability of the monitoring device relative to the subject body at a first time, and decreasing the stability of the monitoring device relative to the subject body at a second time.

According to other embodiments of the present invention, a monitoring device that is configured to be attached to a subject includes a location sensor, a sensor that is configured to detect and/or measure physiological information from the subject, and at least one actuator configured to change stability of the monitoring device relative to the subject body when the location sensor indicates the subject has changed locations. The sensor may be an optical sensor that includes at least one optical emitter and at least one optical detector, although various other types of sensors may be utilized. The at least one actuator may increase the stability/tension of the monitoring device relative to the subject body when the location sensor indicates the subject is at a particular location, and may decrease the stability of the monitoring device relative to the subject body when the location sensor indicates the subject is no longer at the particular location.

According to some embodiments, a method of monitoring a subject via a monitoring device includes changing the stability of the monitoring device relative to the subject body when the location sensor indicates the subject has changed locations. For example, in some embodiments, changing the stability of the monitoring device relative to the subject body when the location sensor indicates the subject has changed locations includes increasing the stability of the monitoring device relative to the subject body when the location sensor indicates the subject is at a particular location, and decreasing the stability of the monitoring device relative to the subject body when the location sensor indicates the subject is no longer at the particular location.

According to other embodiments of the present invention, a monitoring system includes a wearable monitoring device configured to be attached to a body of a subject and a remote device in communication with the monitoring device, wherein the remote device includes at least one environmental sensor configured to detect and/or measure at least one environmental condition in a vicinity of the subject. The monitoring device includes a sensor that is configured to detect and/or measure physiological information from the subject, and at least one actuator that is configured to adjust stability of the monitoring device relative to the subject body. The at least one actuator is configured to increase the stability of the monitoring device relative to the subject body in response to receiving information from the remote device about an environmental condition in the vicinity of the subject.

According to other embodiments of the present invention, a monitoring system includes a wearable monitoring device configured to be attached to a body of a subject, and at least one processor in communication with the monitoring device. The monitoring device includes a sensor that is configured to detect and/or measure physiological information from the subject, and at least one actuator that is configured to adjust stability of the monitoring device relative to the subject body. The at least one processor is configured to cause the at least one actuator to adjust stability of the monitoring device relative to the subject body according to a preset value when the monitoring device is attached to the body of the subject.

According to other embodiments of the present invention, a monitoring device configured to be attached to a body of a subject includes a sensor that is configured to sense body gestures by the subject, and at least one actuator configured to adjust stability of the monitoring device relative to the subject body in response to the sensor detecting a body gesture by the subject.

According to other embodiments of the present invention, a monitoring system includes a wearable monitoring device configured to be attached to a body of a subject, and at least one processor in communication with the monitoring device. The monitoring device includes a sensor configured to sense body gestures by the subject, and at least one actuator configured to adjust stability of the monitoring device relative to the subject body. The at least one processor is configured to determine if signal quality from the sensor is sufficient for gestural recognition and to cause the at least one actuator to adjust stability of the monitoring device relative to the subject body in response to determining that the signal quality is not sufficient for gestural recognition.

According to other embodiments of the present invention, a monitoring device configured to be attached to a body of a subject includes a sensor that is configured to detect and/or measure physiological information from the subject, at least one actuator, and at least one processor in communication with the sensor. The sensor includes at least one physiological sensor and the at least one actuator is configured to adjust and/or actuate the at least one physiological sensor. The at least one processor is configured to cause the at least one actuator to adjust and/or actuate the at least one physiological sensor in response to detecting that signal quality from the at least one physiological sensor is below a threshold level.

According to other embodiments of the present invention, a monitoring system includes a wearable monitoring device configured to be attached to a body of a subject, and at least one processor. The monitoring device includes a sensor having at least one physiological sensor that is configured to detect and/or measure physiological information from the subject. The monitoring device also includes at least one actuator that is configured to adjust and/or actuate the at least one physiological sensor. The at least one processor is in communication with the sensor and is configured to cause the at least one actuator to adjust and/or actuate the at least one physiological sensor in response to detecting signal quality from the at least one physiological sensor is below a threshold level.

According to other embodiments of the present invention, a monitoring system includes a wearable monitoring device configured to be attached to a body of a subject, and a light source. The monitoring device includes a sensor that is configured to detect and/or measure light exposure and at least one processor in communication with the sensor. The at least one processor is configured to turn on the light source in response to determining that light in a vicinity of the subject is below a threshold.

Various types of actuators may be utilized in accordance with embodiments of the present invention. For example, an actuator may be an expandable and retractable bladder, may include a material that changes shape in response to the application of light and/or heat thereto, may include a material that undergoes a phase change in response to a change in temperature, may include a conductive material that changes shape in response to the application of electrical current thereto, etc. In some embodiments, an actuator may be an electromechanical actuator.

Monitoring devices in accordance with some embodiments of the present invention may be configured to be positioned at or within an ear of a subject and at least one actuator is configured to change stability of the monitoring device relative to a portion of the ear.

Monitoring devices in accordance with some embodiments of the present invention may be configured to be secured to an appendage of a subject and at least one actuator is configured to change stability of the monitoring device relative to a portion of the appendage of the subject. For example, in some embodiments, a monitoring device is a band that surrounds an appendage. One or more actuators are configured to adjust the tension of the band around the appendage of the subject. In some embodiments, the band may include an electro active polymer material, a thermoactive material, or a piezoelectric material.

Monitoring devices, according to embodiments of the present invention, are advantageous over conventional monitoring devices because, by increasing device securing tension and reducing device-to-body movement, a more stable sensor signal may be achieved. Moreover, monitoring devices according to embodiments of the present invention have additional benefits, such as the prevention of a device becoming disconnected from the body. For example, conventional headphones may fall out of a runner's ear during intense sprints. An earbud monitoring device according to embodiments of the present invention can change its shape in response to user activity to more stably couple to the wearer's ear and prevent dislodging. A bracelet or watch according to embodiments of the present invention can be worn in a loose configuration during general inactivity, but can become tighter during more intense activities.

In addition, monitoring devices, according to embodiments of the present invention, can be more comfortable than conventional monitoring devices by helping regulate temperature in a sensor interaction area. Embodiments of the present invention may include fabric or advanced textile support structures that loosen in hot environments to increase skin surface airflow and restrict to insulate in cold environments.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIGS. 2A-2J illustrate monitoring devices that can be positioned within an ear of a subject, according to some embodiments of the present invention. FIG. 2A illustrates a monitoring device in a relaxed mode and FIG. 2B illustrates the monitoring device of FIG. 2A in an actuated mode to increase stability of the monitoring device relative to the ear of the subject. FIG. 2C illustrates a monitoring device in a relaxed mode and FIG. 2D illustrates the monitoring device of FIG. 2C in an actuated mode to increase stability of the monitoring device relative to the ear of the subject. FIG. 2E illustrates a monitoring device in a relaxed mode and FIG. 2F illustrates the monitoring device of FIG. 2E in an actuated mode to increase stability of the monitoring device relative to the ear of the subject. FIG. 2G illustrates a monitoring device in a relaxed mode and FIG. 2H illustrates the monitoring device of FIG. 2G in an actuated mode to increase stability of the monitoring device relative to the ear of the subject. FIG. 2I illustrates the monitoring device of FIG. 2A positioned within an ear of a subject. FIG. 2J illustrates the monitoring device of FIG. 2C positioned within an ear of a subject.

FIG. 3A illustrates the monitoring device in a relaxed mode and FIG. 3B illustrates the monitoring device in an actuated mode to increase stability of the monitoring device relative to the appendage of the subject.

FIGS. 5A-5D illustrate a watch that includes one or more sensors for measuring physiological information from a subject and/or one or more sensors for measuring environmental information in a vicinity of the subject, and wherein the band includes a tensioning mechanism or actuator in accordance with some embodiments of the present invention.

FIGS. 6A-6D illustrate an actuator that incorporates a material such as nitinol that can expand and contract and that can be utilized with various monitoring devices, such as the monitoring devices illustrated in FIGS. 2A-2J, 3A-3B, 4A-4B and 5A-5D, according to some embodiments of the present invention.

FIGS. 8A-8E illustrate an electromechanical device that can be utilized as an actuator with various monitoring devices, such as the monitoring devices illustrated in FIGS. 2A-2J, 3A-3B, 4A-4B and 5A-5D, according to some embodiments of the present invention.

FIGS. 10A-10E illustrate a bladder that extends and retracts and that can be utilized as an actuator with various monitoring devices, such as the monitoring devices illustrated in FIGS. 2A-2J, 3A-3B, 4A-4B and 5A-5D, according to some embodiments of the present invention.

FIG. 12A illustrates the bladders uninflated and FIG. 12B illustrates the bladders inflated.

FIGS. 14A-14B illustrate an actuator that incorporates material that undergoes a phase change when exposed to temperature variations such that the actuator extends and retracts and that can be utilized with various monitoring devices, such as the monitoring devices illustrated in FIGS. 2A-2J, 3A-3B, 4A-4B and 5A-5D, according to some embodiments of the present invention.

2A-2J, 3A-3B, 4A-4B and 5A-5D, according to some embodiments of the present invention.

FIGS. 16A-16E illustrate an actuator that incorporates material that contracts when heated and that can be utilized with various monitoring devices, such as the monitoring devices illustrated in FIGS. 2A-2J, 3A-3B, 4A-4B and 5A-5D, according to some embodiments of the present invention.

Figure 17B:
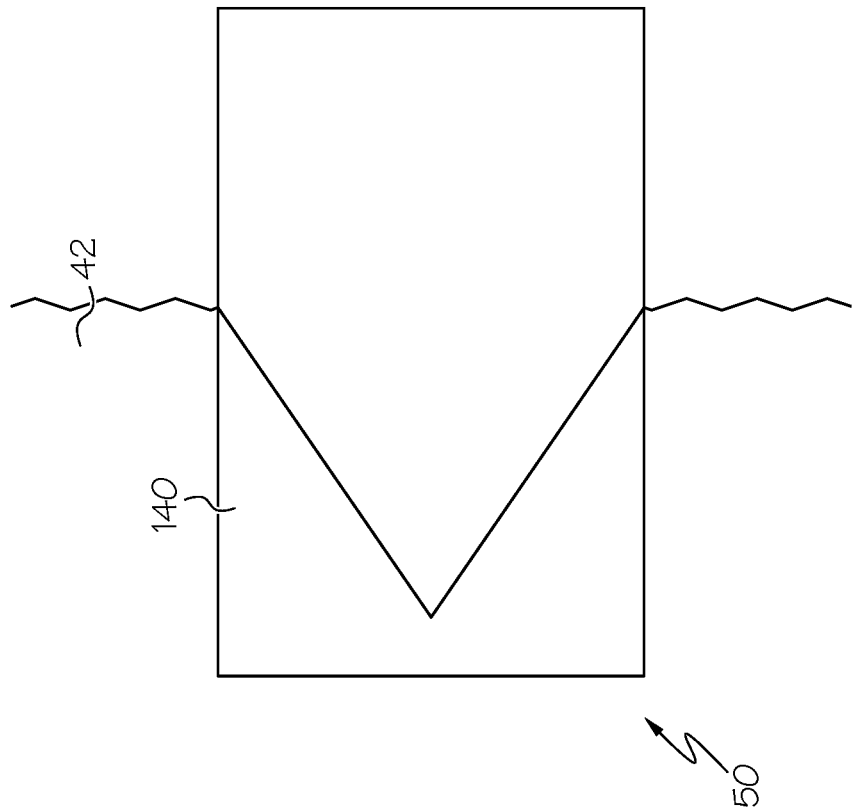
Figure 17A:
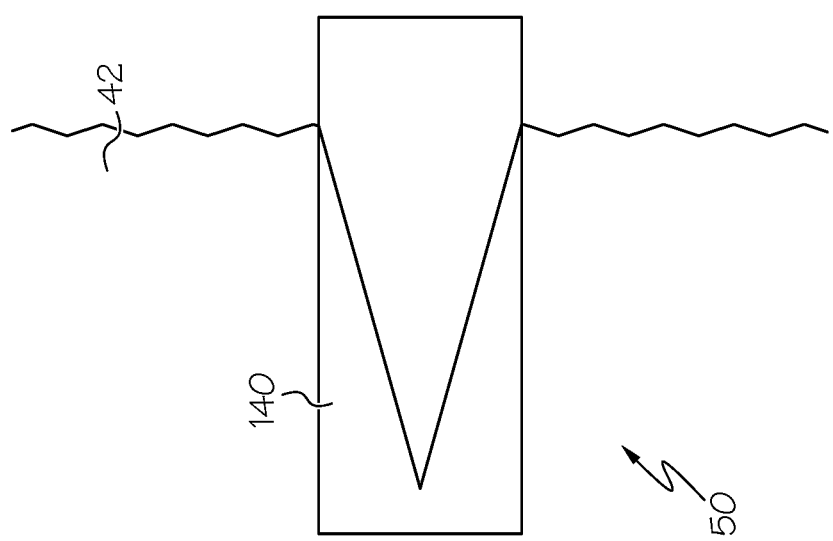

FIGS. 17A-17B illustrate an actuator that incorporates shape memory polymer material that expands and contracts and that can be utilized with various monitoring devices, such as the monitoring devices illustrated in FIGS. 2A-2J, 3A-3B, 4A-4B and 5A-5D, according to some embodiments of the present invention.

FIGS. 18A-18E illustrate an actuator that incorporates a piezoelectric or dielectric elastomer material that expands and contracts and that can be utilized with various monitoring devices, such as the monitoring devices illustrated in FIGS. 2A-2J, 3A-3B, 4A-4B and 5A-5D, according to some embodiments of the present invention.

FIGS. 19A-19F illustrate a monitoring device having a plurality of bladders that expand and retract, according to some embodiments of the present invention.

Figure 20:
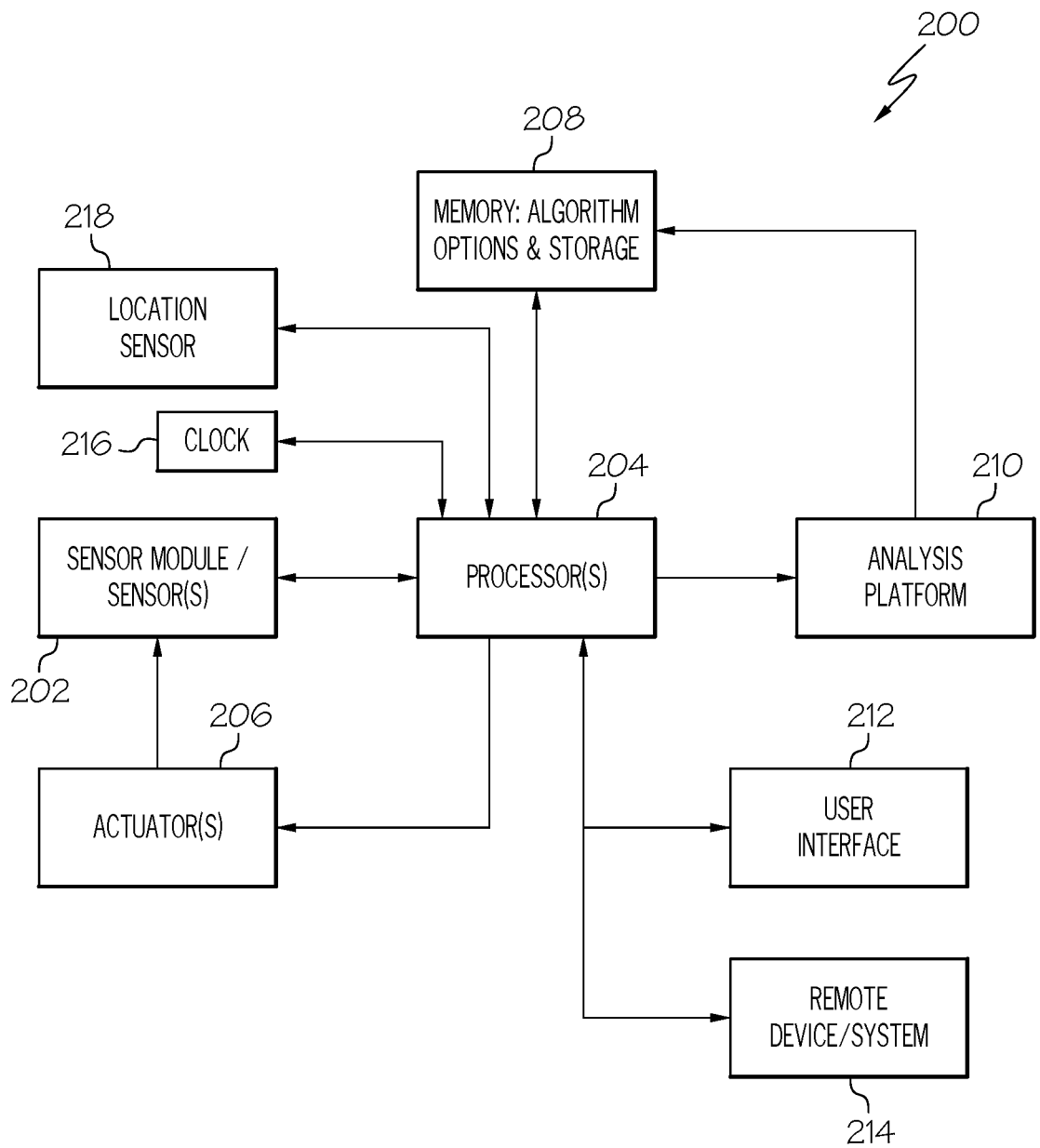

FIG. 20 is a block diagram of a monitoring device according to some embodiments of the present invention.

FIG. 21A is a graph illustrating good sleep quality in terms of heart rate variability (HRV) versus time.

FIG. 21B is a graph illustrating bad sleep quality in terms of HRV versus time.

Figure 22:
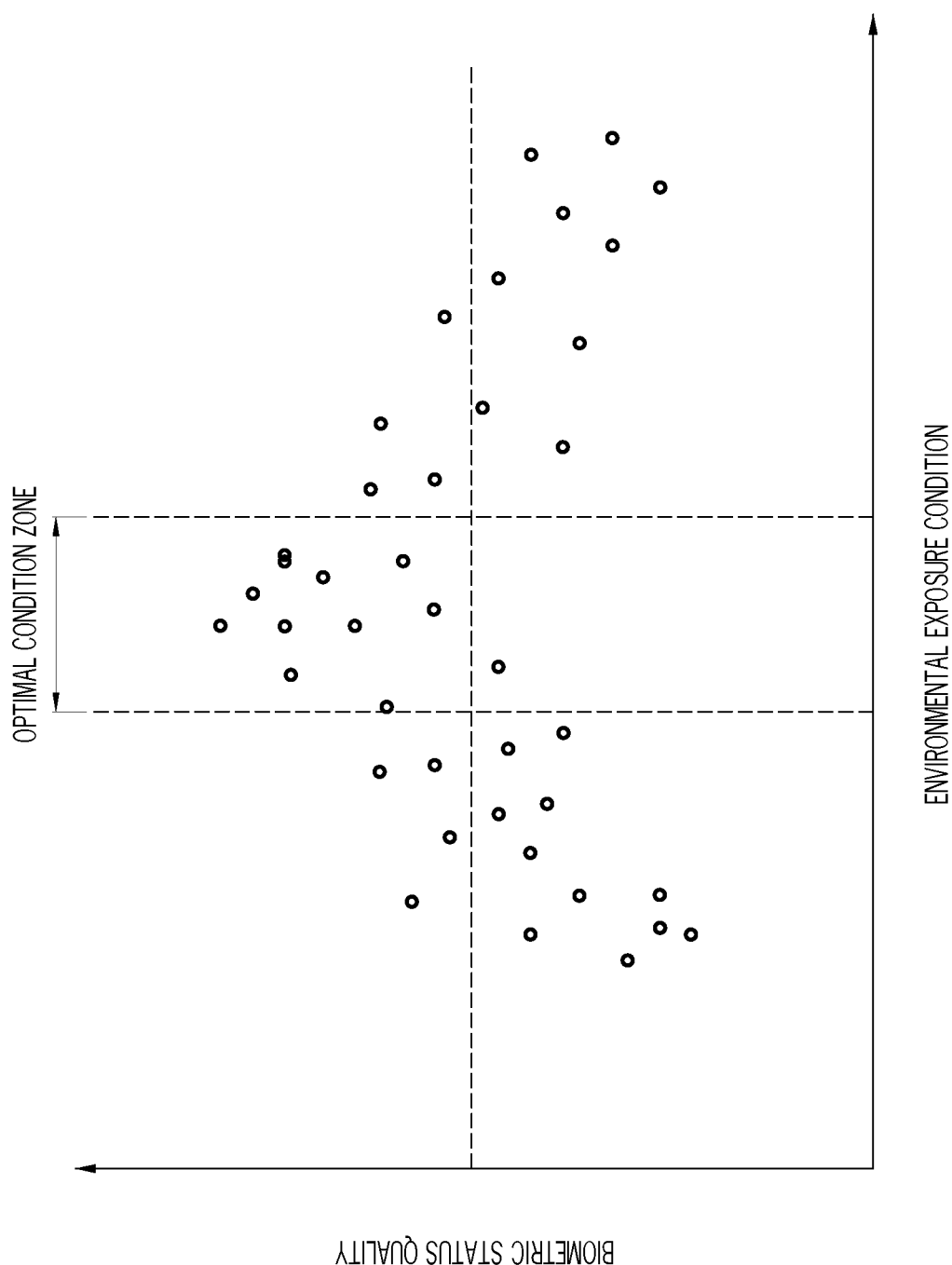

FIG. 22 is a graph illustrating biometric status quality versus environmental exposure condition.

DETAILED DESCRIPTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "secured", "connected", "attached" or "coupled" to another feature or element, it can be directly secured, connected, attached or coupled to the other feature or element or intervening features or elements may be present. In contrast, when a feature or element is referred to as being "directly secured", "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary more or less, for example by +/−20%, +/−10%, +/−5%, +/−1%, +/−0.5%, +/−0.1%, etc.

The terms "sensor", "sensing element", and "sensor module", as used herein, are interchangeable and refer to a sensor element or group of sensor elements that may be utilized to sense information, such as information (e.g., physiological information, body motion, etc.) from the body of a subject and/or environmental information in a vicinity of a subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module.

The term "optical emitter", as used herein, may include a single optical emitter and/or a plurality of separate optical emitters that are associated with each other.

The term "optical detector", as used herein, may include a single optical detector and/or a plurality of separate optical detectors that are associated with each other.

The term "wearable sensor module", as used herein, refers to a sensor module configured to be worn on or near the body of a subject.

The terms "monitoring device" and "biometric monitoring device", as used herein, are interchangeable and include any type of device, article, or clothing that may be worn by and/or attached to a subject and that includes at least one sensor/sensing element/sensor module. Exemplary monitoring devices may be embodied in an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "headset", as used herein, is intended to include any type of device or earpiece that may be attached to or near the ear (or ears) of a user and may have various configurations, without limitation. Headsets incorporating optical sensors, as described herein, may include mono headsets (a device having only one earbud, one earpiece, etc.) and stereo headsets (a device having two earbuds, two earpieces, etc.), earbuds, hearing aids, ear jewelry, face masks, headbands, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination. The terms "headset" and "earphone", as used herein, are interchangeable.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear a monitoring device, according to embodiments of the present invention.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat underwear, etc.), a mouthpiece or tooth piece, contact lenses, or the like. Examples of a distributed processor comprise "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

In the following figures, various monitoring devices will be illustrated and described for attachment to the ear or an appendage of the human body. However, it is to be understood that embodiments of the present invention are not limited to devices worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.);

noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Optical coupling into the blood vessels of the ear may vary between individuals. As used herein, the term "coupling" refers to the interaction or communication between excitation energy (such as light) entering a region and the region itself. For example, one form of optical coupling may be the interaction between excitation light generated from within an optical sensor of an earbud (or other device positioned at or within an ear) and the blood vessels of the ear. In one embodiment, this interaction may involve excitation light entering the ear region and scattering from a blood vessel in the ear such that the temporal change in intensity of scattered light is proportional to a temporal change in blood flow within the blood vessel. Another form of optical coupling may be the interaction between excitation light generated by an optical emitter within an earbud and a light-guiding region of the earbud. Thus, an earbud with integrated light-guiding capabilities, wherein light can be guided to multiple and/or select regions along the earbud, can assure that each individual wearing the earbud will generate an optical signal related to blood flow through the blood vessels. Optical coupling of light to a particular ear region of one person may not yield photoplethysmographic signals for each person. Therefore, coupling light to multiple regions may assure that at least one blood-vessel-rich region will be interrogated for each person wearing an earbud. Coupling multiple regions of the ear to light may also be accomplished by diffusing light from a light source within an earbud.

According to some embodiments of the present invention, "smart" monitoring devices including, but not limited to, armbands and earbuds, that increase tension to the body of a wearer (e.g., tighten up) during extreme activity, at predetermined times, and/or at predetermined locations are provided. The increased tension can prevent device attachment failures commonly experienced during extreme activity, such as running, exercising, etc. Embodiments of the present invention improve sensor performance by stabilizing a monitoring device during extreme activities, during certain times of the day, at one or more locations, and when a user is exposed to one or more environmental conditions. In addition, embodiments of the present invention may provide adjustable comfort for the wearer.

Figure 1A:
FIG. 1A is a perspective view of a conventional PPG device attached to the ear of a person.
Figure 1B:
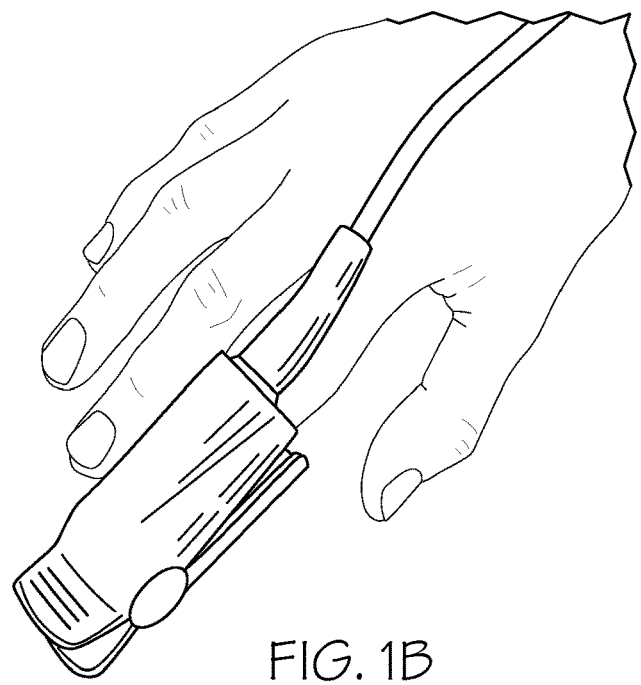
FIG. 1B is a perspective view of a conventional PPG device attached to a finger of a person.
Figure 1C:
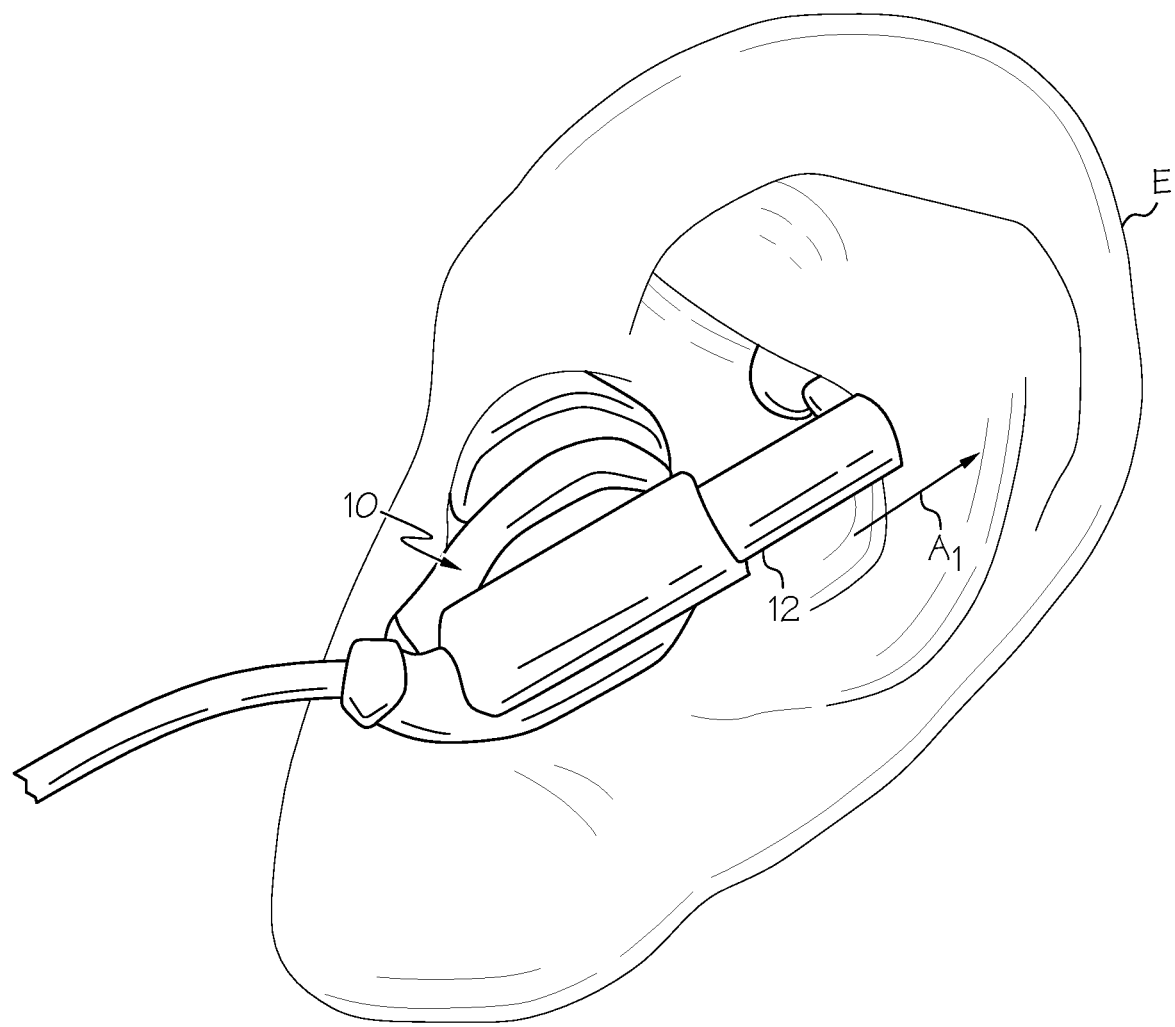
FIG. 1C illustrates a conventional PPG device attached to the ear of a person, and wherein a biasing element is utilized to retain the PPG device in the person's ear.
Figure 2J:
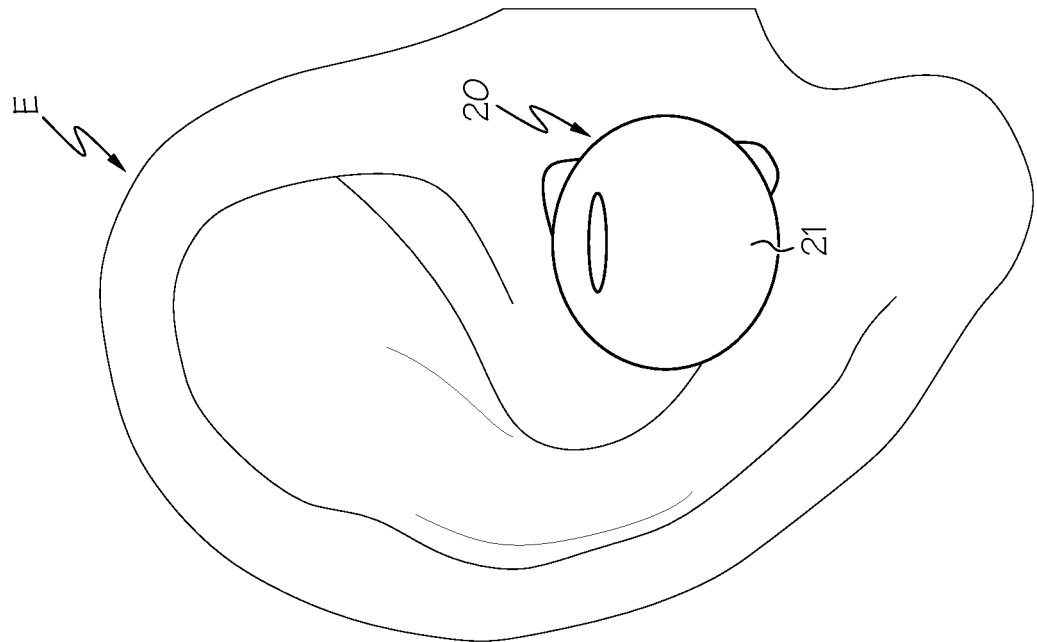
Figure 2I:
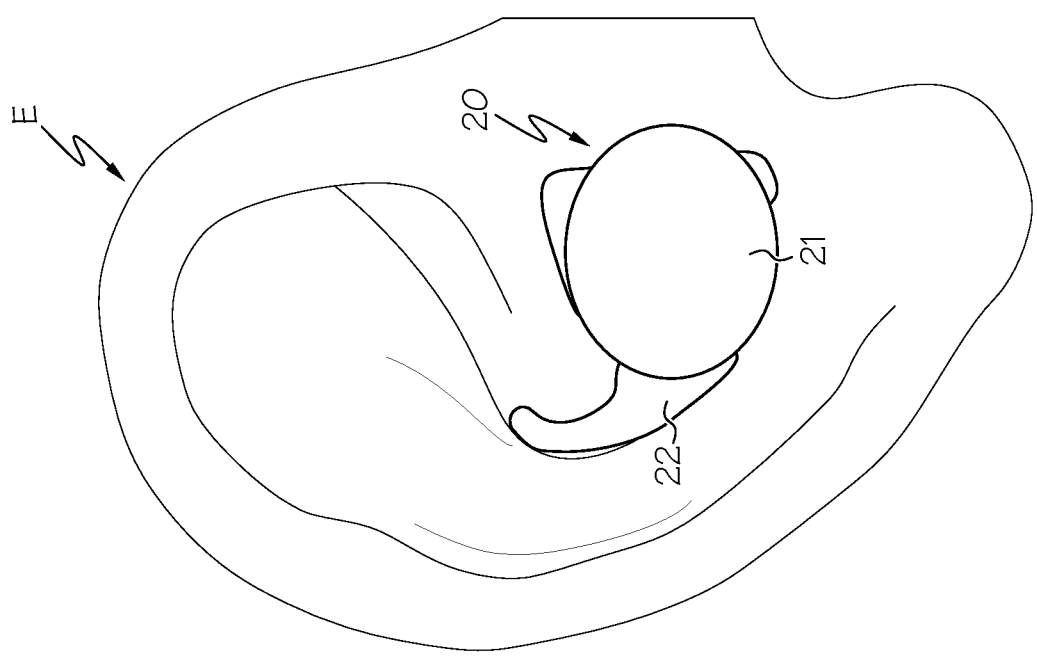

FIGS. 2A-2J illustrate monitoring devices that can be positioned within an ear of a subject, according to some embodiments of the present invention. FIGS. 2A-2B illustrate an earbud monitoring device 20 configured to be positioned within an ear E of a subject (as shown in FIG. 2I) and that includes a housing 21, a stabilizer arm 22 (e.g., configured to engage a part of the ear, such as the helix, antihelix, etc.), and an ear tip or audio port 23 configured to be directed toward the ear canal of the ear. FIG. 2A illustrates the earbud monitoring device 20 in a relaxed mode and FIG. 2B illustrates the monitoring device 20 of FIG. 2A in an actuated mode wherein a size/shape of the device 20 has changed to increase the stability of the monitoring device 20 relative to the ear of the subject. As illustrated in FIG. 2B, the stabilizer 22 has become elongated relative to its relaxed state in FIG. 2A so as to increase the "grip" of the device 20 on the ear, thereby increasing stability of the device 20 in the ear.

FIGS. 2C-2D illustrate an earbud monitoring device 20 configured to be positioned within an ear E of a subject (as shown in FIG. 2J) and that includes a housing 21, an internal stabilizer member 25 associated with the housing 21, and an ear tip or audio port 23 configured to be directed toward the ear canal of the ear. FIG. 2C illustrates the monitoring device 20 in a relaxed mode and FIG. 2D illustrates the monitoring device 20 of FIG. 2C in an actuated mode wherein the size/shape of the device has changed to increase the stability of the monitoring device 20 relative to the ear of the subject. As illustrated in FIG. 2D, the stabilizer member 25 has changed shape relative to its relaxed state in FIG. 2A so as to cause the housing 21 to change shape and thereby increase the "grip" of the device 20 on the ear, thereby increasing the stability of the device 20 in the ear.

FIGS. 2E-2F illustrate the earbud monitoring device 20 of FIGS. 2A-2B. A piezoelectric actuator 26 (e.g., a piezo polymer film with electrodes for voltage stimulation, etc.) is located within the stabilizer arm 22. The piezoelectric actuator 26 is in a relaxed state in FIG. 2E and in an actuated state in FIG. 2F. As illustrated in FIG. 2F, the stabilizer 22 has become elongated relative to its relaxed state in FIG. 2E because of actuation of the piezoelectric actuator 26.

FIGS. 2G-2H illustrate the earbud monitoring device 20 of FIGS. 2C-2D. A piezoelectric actuator 26 (e.g., a piezo polymer film with electrodes for voltage stimulation, etc.) is located within the housing 21. The piezoelectric actuator 26 is in a relaxed state in FIG. 2G and in an actuated state in FIG. 2H. As illustrated in FIG. 2H, the stabilizer 22 has become elongated relative to its relaxed state in FIG. 2G because of actuation of the piezoelectric actuator 26 so as to change the shape of the housing 21.

The housing 21 of each monitoring device 20 illustrated in FIGS. 2A-2J includes at least one sensor region (not shown) that is configured to contact a selected area of the ear when the housing 21 is attached to the ear E. The sensor region(s) may be contoured (i.e., is "form-fitted") to matingly engage a portion of the ear, such as between the anti tragus and acoustic meatus, etc. However, monitoring devices in accordance with embodiments of the present invention can have sensor regions configured to engage various portions of the ear.

The sensor region in each monitoring device 20 includes a sensor module (202, FIG. 21) that is configured to detect and/or measure physiological information from the subject. In some embodiments, the sensor module may be configured to detect and/or measure one or more environmental conditions in a vicinity of the subject wearing the monitoring device. The sensor module may be an optical sensor module that includes at least one optical emitter and at least one optical detector. Exemplary optical emitters include, but are not limited to light-emitting diodes (LEDs), laser diodes (LDs), compact incandescent bulbs, micro-plasma emitters, IR blackbody sources, or the like.

In addition, the sensor module may include various types of sensors including and/or in addition to optical sensors. For example, the sensor module may include one or more inertial sensors (e.g., an accelerometer, piezoelectric sensor, vibration sensor, photoreflector sensor, etc.) for detecting changes in motion, one or more thermal sensors (e.g., a thermopile, thermistor, resistor, etc.) for measuring temperature of a part of the body, one or more electrical sensors for measuring changes in electrical conduction, one or more skin humidity sensors, and one or more acoustical sensors.

Each monitoring device 20 in FIGS. 2A-2J includes at least one actuator (e.g., piezoelectric actuator 26, etc.) that is configured to adjust the stability of the monitoring device 20 relative to the ear of the subject in response to the sensor module detecting a change in subject activity. In some embodiments, the sensor region or one or more other portions of the monitoring device 20 is expanded to increase the "grip" of the device on the ear, thereby increasing the stability of the monitoring device 20 relative to the ear in response to detecting an increase in subject activity, and is configured to retract so as to decrease the "grip" on the ear in response to detecting a decrease in subject activity. Detecting a change in subject activity may include detecting a change in at least one subject vital sign, such as subject heart rate, subject blood pressure, subject temperature, subject respiration rate, subject perspiration rate, etc. In other embodiments, the sensor module includes a motion sensor, such as an accelerometer, gyroscope, etc., and detecting a change in subject activity includes detecting a change in subject motion via the motion sensor.

It should be noted that the exemplary devices 20 of FIGS. 2A-2J may comprise an adjustable stabilizer that may be adjusted for the user autonomously and/or manually. For example, the exemplary earbud 20 of FIGS. 2E and 2F may include an actuator that may be adjusted manually for comfort, and that may or may not be adjusted autonomously by the user. As a specific example, if the piezoelectric arm 26 illustrated in FIGS. 2E and 2F was replaced with a manually bendable arm, such as an arm made out of pliable or reshapeable material (such as metal or soft plastics) or an arm having a hinging feature, the user may adjust the stabilization manually by folding (or extending the arm). This may be useful for an application where a user wants to wear the device 20 during everyday life activities, where higher comfort is involved, but needs more stabilization during exercise, where stabilization (and not comfort) is a key a priority. This may be particularly true for earbuds, where an extending stabilization arm may be discomforting for all-day use.

According to some embodiments, the type of activity may be identified or predicted via the sensor module and the sensor region or one or more other portions of the monitoring device 20 is expanded to increase the stability of the monitoring device 20 relative to the ear in response to the identified or predicted activity. The implemented actuation may be based on stored profiles (such as a look-up table) or learned profiles (such as machine learning with human input).

According to other embodiments of the present invention, the sensor region or one or more other portions of the monitoring device 20 is expanded to increase the "grip" of the device 20 on the ear, thereby increasing the stability of the monitoring device 20 relative to the ear in response to the sensor module detecting a change in an environmental condition in the vicinity of the subject. Exemplary changes in environmental conditions include changes in one or more of the following ambient conditions: temperature, humidity, air quality, barometric pressure, radiation, light intensity, and sound. For example, the sensor region or other portions of the monitoring device may be expanded when air quality worsens or becomes detrimental to the wearer, and may be retracted when air quality improves.

According to other embodiments of the present invention, the sensor module of the monitoring device 20 includes a clock (216, FIG. 21), and the sensor region or one or more other portions of the monitoring device is expanded to increase the stability of the monitoring device 20 relative to the ear at one or more predetermined times. For example, an actuator may be configured to expand the sensor region at a particular time of day (e.g., the time of day when the wearer is typically exercising) to thereby increase stability of the monitoring device. The actuator may retract the sensor region or other actuated portion of the monitoring device at another time of day, for example, at a time of day when the wearer is less active (e.g., nighttime, etc.).

According to other embodiments of the present invention, the sensor module of the monitoring device 20 may include a location sensor (218, FIG. 21), such as a GPS receiver or other geolocation device, and the sensor region or one or more other portions of the monitoring device 20 is expanded to increase the stability of the monitoring device 20 relative to the ear when the location sensor indicates the subject has changed locations. For example, an actuator may be configured to expand the sensor region or other portions of the monitoring device 20 when the location sensor indicates the subject is at a particular location (e.g., at the gym, at the mall, etc.), and may retract the sensor region when the location sensor indicates the subject is no longer at the particular location (e.g., when the wearer is at work, home etc.). The locations selected for actuation of monitoring devices 20, according to embodiments of the present invention, may be personalized for the user and stored in memory.

In other embodiments, the location sensor may be associated with a separate device carried by the subject, such as a handset, smartphone, etc.

In some embodiments, when the monitoring device 20 is first engaged or turned on, the actuator may vibrate to stimulate blood flow and facilitate measurement via the sensor module.

Other factors may be utilized to trigger actuation of an actuator of the monitoring device 20 to thereby increase stability of the monitoring device 20. For example, higher body temperature readings detected by a thermal sensor associated with the sensor module may trigger actuation. The principle behind this may be that higher body temperatures are associated with higher motion, for example. The detection of higher light levels, the detection of higher changes in light intensity, and/or the detection of particular wavelengths via an optical sensor associated with the sensor module may trigger actuation. Lower potential drops detected by an electrical sensor associated with the sensor module may trigger actuation. Lower skin humidity readings detected via a humidity sensor associated with the sensor module may trigger actuation. Higher acoustic noise levels detected via an acoustical sensor associated with the sensor module may trigger actuation.

In some embodiments, the trigger for actuation may be caused by an input response from the user. For example, the user may determine that they want a more stabilized reading and then may initiate the actuation directly. This may entail pressing a button, flipping a switch, selecting actuation options from a menu, using verbal commands, using gesture commands, and the like.

In some embodiments, the trigger for actuation may be induced for the purpose of facilitating a measurement that requires a tighter coupling of a wearable device to the body. Nonlimiting examples of such measurements may include heart rate variability (HRV), R-R interval (RRi), blood pressure, cardiac output, respiration rate, heart rate, and the like. A specific example may be described for the case of a subject wearing a sensor-laden device, such as a biometric wristband, armband, earbud, or the like, comprising the system illustrated in FIG. 21. The processor(s) 204 and/or analysis platform 210 of FIG. 21 may asses that a user is in an elevated stress state and then in response initiate a blood pressure measurement. During the blood pressure measurement, the biometric device may automatically compress and decompress, taking sensor readings (such as pressure sensor readings of the wearable device against the skin, for example) throughout the process. In one specific embodiment, the processor(s) 204 and/or analysis platform 210 may determine the systolic and/or diastolic pressure by assessing the pulsatile amplitude of the pulse and measured pressure from a blood pressure sensor 202 (such as with an oscillometric sensor, for example). The peak pulsatile amplitude may be associated with the maximum arterial pressure (MAP), and the systolic and diastolic pressure may then be determined by the measured pressure when the pulsatile amplitude is at certain percentages of that associated with the MAP. For example, the measured pressure at ~70% of the peak pulsatile signal may be associated with systolic pressure, and the pressure at ~50% of the peak pulsatile signal may be associated with the diastolic pressure.

The initiation of a blood pressure reading (or other biometric reading) may be via user input (manual) or autonomous. In some cases, the initiation of a biometric measurement may be triggered by a processor 204 and/or analysis platform 210 determining that the user is in an elevated stress state. For example, an elevated heart rate or an elevated heart rate in absence of substantial physical activity may be indicative of a high risk of a cardiac event. Sensor readings for a PPG sensor 202, for example, may be processed to determine the subject's heart rate, and sensor readings from an inertial sensor 202 (such as an accelerometer) may be processed to determine if the subject is active or at rest. The processor(s) 204 and/or analysis platform 210 may process the PPG sensor information and inertial sensor information to determine whether the user is in an elevated stress state, and this may trigger the actuator(s) to begin an autonomous blood pressure reading as previously described.

In some embodiments, the system of FIG. 21 may be used to assess changes in one type of sensor reading in response to one or more actuation events. In some cases, a physiological assessment may be generated. As a specific example, the processor(s) 204 may initiate a compression event in a wearable device, such as a wearable wrist device as shown in FIGS. 20A-20F. The system may then process the change in sensor readings from one or more PPG sensors within the wearable device. By monitoring how blood flow changes in response to compression and decompression, an assessment of blood perfusion may be generated. Such an assessment may be generated by utilizing an auscultatory sensor instead of a PPG sensor, where blood-flow sounds are used to assess perfusion in response to one or more actuation events.

Figure 3A:
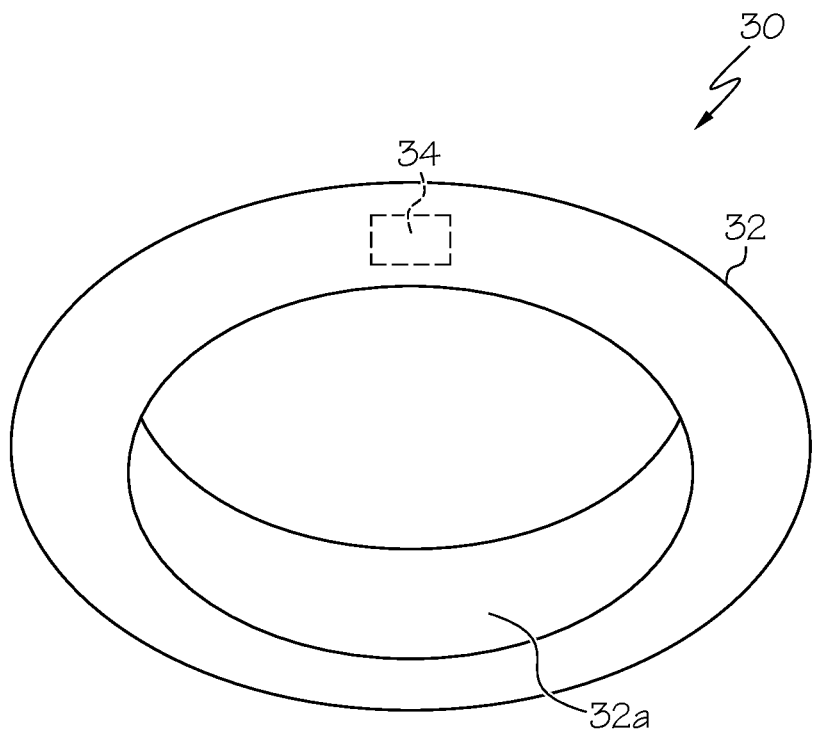
FIGS. 3A-3B illustrate a monitoring device that can be positioned around an appendage of the body of a subject, according to some embodiments of the present invention.
Figure 3B:
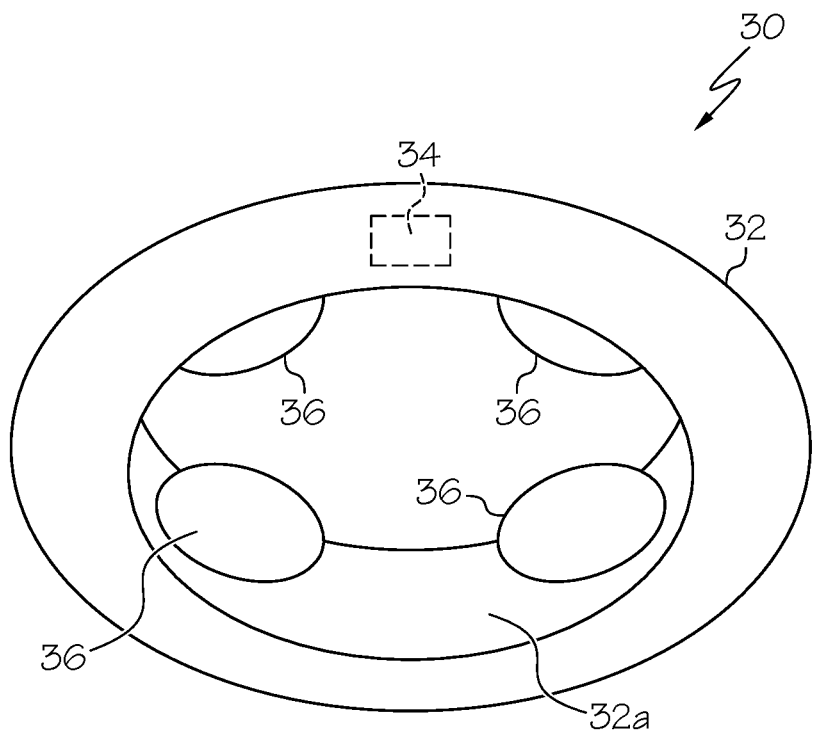

FIGS. 3A-3B illustrate a monitoring apparatus 30 in the form of a sensor band 32 configured to be secured to an appendage (e.g., an arm, wrist, hand, finger, toe, leg, foot, neck, etc.) of a subject. The band 32 includes a sensor region 34 on or extending from the inside surface 32a of the band 32. The sensor region 34 includes a sensor module that is configured to detect and/or measure physiological information from the subject. In some embodiments, the sensor module may be configured to detect and/or measure one or more environmental conditions in a vicinity of the subject wearing the monitoring device 30. The sensor module may be an optical sensor module that includes at least one optical emitter and at least one optical detector. Exemplary optical emitters include, but are not limited to light-emitting diodes (LEDs), laser diodes (LDs), compact incandescent bulbs, micro-plasma emitters, IR blackbody sources, or the like.

In addition, the sensor module may include various types of sensors including and/or in addition to optical sensors. For example, the sensor module may include one or more inertial sensors (e.g., an accelerometer, piezoelectric sensor, vibration sensor, photoreflector sensor, etc.) for detecting changes in motion, one or more thermal sensors (e.g., a thermopile, thermistor, resistor, etc.) for measuring temperature of a part of the body, one or more electrical sensors for measuring changes in electrical conduction, one or more skin humidity sensors, and one or more acoustical sensors.

The illustrated monitoring device 30 also includes a plurality of actuators 36 that are configured to adjust the stability of the monitoring device 30 relative to the appendage of the subject in response to the sensor module detecting a change in subject activity, and/or in response to the detection of a change in an environmental condition in a vicinity of the wearer. In response to detecting an increase in subject activity, the actuators 36 are expanded outwardly to increase the tension of the monitoring device 30 (i.e., tighten) around an appendage, thereby increasing the stability of the monitoring device 30 relative to the appendage. In response to detecting a decrease in subject activity, the actuators 36 can be retracted thereby reducing the tension of the monitoring device 30 (i.e., loosen) relative to the appendage. Detecting a change in subject activity may include detecting a change in at least one subject vital sign, such as subject heart rate, subject blood pressure, subject temperature, subject respiration rate, subject perspiration rate, etc. In other embodiments, the sensor module includes a motion sensor, such as an accelerometer, gyroscope, etc., and detecting a change in subject activity includes detecting a change in subject motion via the motion sensor.

According to some embodiments, the type of activity may be identified or predicted via the sensor module and the actuators 36 may be expanded outwardly to increase the stability of the monitoring device 30 relative to the appendage in response to the identified or predicted activity. The implemented actuation (i.e., expansion of the actuators 36) may be based on stored profiles (such as a look-up table) or learned profiles (such as machine learning with human input). The types of identified activity may include, but are not limited to, running, walking, cycling, swimming, weight-lifting, relaxing, sleeping, sleep state, and the like.

According to other embodiments of the present invention, the actuators 36 are expanded outwardly to increase the stability of the monitoring device 30 relative to the appendage in response to the sensor module detecting a change in an environmental condition in the vicinity of the subject. Exemplary changes in environmental conditions include changes in one or more of the following: temperature, humidity, air quality, barometric pressure, radiation, light intensity, and sound. For example, the actuators 36 may be expanded outwardly when air quality worsens or becomes detrimental to the wearer, and may be retracted when air quality improves.

According to other embodiments of the present invention, the monitoring device 30 includes a clock (not shown), and the actuators 36 are expanded outwardly to increase the stability of the monitoring device 30 relative to the appendage at one or more predetermined times. For example, the actuators 36 may be expanded outwardly at a particular time of day (e.g., the time of day when the wearer is typically exercising) to thereby increase stability of the monitoring device 30. The actuators 36 may be retracted at another time of day, for example, at a time of day when the wearer is less active (e.g., nighttime, etc.).

According to other embodiments of the present invention, the sensor module of the monitoring device 30 may include a location sensor (not shown), such as a GPS receiver or other geolocation device, and the actuators 36 may be expanded outwardly to increase the stability of the monitoring device 30 relative to the appendage when the location sensor indicates the subject has changed locations. For example, the actuators 36 may be expanded outwardly when the location sensor indicates the subject is at a particular location (e.g., at the gym, etc.), and may retract when the location sensor indicates the subject is no longer at the particular location (e.g., when the wearer is at work, etc.).

In some embodiments, when the monitoring device 30 is first engaged or turned on, the actuators 36 may vibrate to stimulate blood flow and facilitate measurement via the sensor module.

As described above with respect to FIGS. 2A-2J, other factors may be utilized to trigger actuation of the actuators 36 of the monitoring device 30 to thereby increase stability of the monitoring device 30. For example, higher body temperature readings detected by a thermal sensor associated with the sensor module may trigger actuation. The detection of higher light levels, the detection of higher changes in light intensity, and/or the detection of particular wavelengths via an optical sensor associated with the sensor module may trigger actuation. Lower potential drops detected by an electrical sensor associated with the sensor module may trigger actuation. Lower skin humidity readings detected via a humidity sensor associated with the sensor module may trigger actuation. Higher acoustic noise levels detected via an acoustical sensor associated with the sensor module may trigger actuation.

Various types of actuators may be utilized in the monitoring device 30 accordance with embodiments of the present invention. For example, an actuator 36 may be an expandable and retractable bladder, may include a material that changes shape in response to the application of light and/or heat thereto, may include a material that undergoes a phase change in response to a change in temperature, may include a conductive material that changes shape in response to the application of electrical current thereto, etc. In some embodiments, an actuator 36 may be an electromechanical actuator.

Figure 4A:
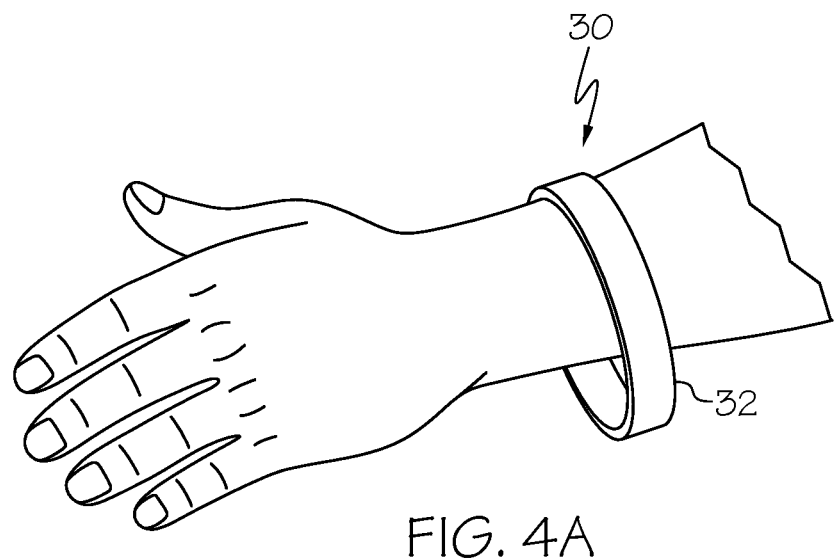
FIG. 4A illustrates a monitoring device according to some embodiments of the present invention that can be positioned around a limb or digit of a subject (illustrated positioned around a wrist), and in a relaxed mode.
Figure 4B:
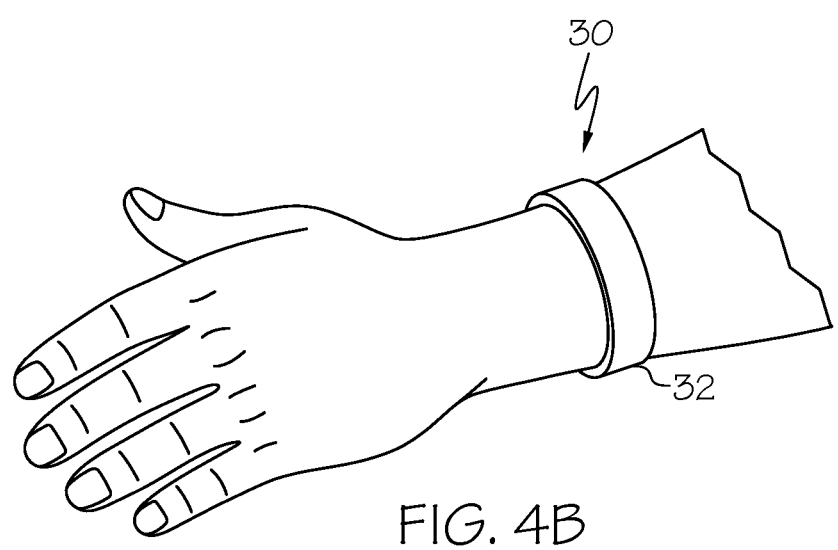
FIG. 4B illustrates the monitoring device of FIG. 4A in an actuated mode wherein the monitoring device grips the wrist of the subject to increase stability of the monitoring device relative to the wrist of the subject.

FIG. 4A illustrates a monitoring device 30 in the configuration of a band, according to some embodiments of the present invention, and in a relaxed mode around an appendage (e.g., an arm, wrist, leg, digit, etc.) of a subject. In the relaxed mode, the monitoring device 30 has a relatively loose fit with respect to the subject's wrist. FIG. 4B illustrates the monitoring device 30 in an actuated mode wherein the band is tightened so as to grip the subject's wrist, thereby increasing stability of the monitoring device relative to the wrist of the subject. This monitoring device 30 may be configured to be worn around other parts of the body. For example, the monitoring device 30 may comprise a band configured to be worn around other limbs, appendages, and digits (fingers and toes) and other parts of the body where bands may be applied (such as the neck, head, and waist).

FIGS. 5A-5D illustrate a monitoring device 40 (shown as a watch) that is configured to be worn on an arm of a subject via a strap or band 42. Although a watch is illustrated, a monitoring device according to embodiments of the present invention can be various other types of devices that wrap around an appendage, such as an arm, leg, finger, toe, etc., or another part of the body, such as a torso, head, neck, waist, etc. Embodiments of the present invention are not limited to monitoring devices that are incorporated in watches. The illustrated watch 40 includes a housing 44 secured to the band 42 and that includes one or more sensors 46 for measuring physiological information from a subject and/or one or more sensors for measuring environmental information in a vicinity of the subject, and/or one or more motion sensors, and/or location sensors, etc. The band 42 includes a tensioning mechanism or actuator 50 for tightening the band 42 relative to the arm (or other appendage) of the subject, as represented by FIG. 5D. In FIG. 5D, $L_1$ represents the length of the band 42 in a relaxed state and $L_2$ represents the length of the band 42 in an actuated or state of increased tension, and wherein $L_2 < L_1$. In other words, the band 42 has a greater length or circumference $L_1$ in a relaxed state, and a shorter length or circumference $L_2$ in an actuated state such that it grips the appendage of a wearer of the device more tightly.

Various types of tensioning mechanisms 50 may be utilized with monitoring devices, such as the monitoring devices 20 of FIGS. 2A-2J, 3A-3B, and 5A-5D. For example, FIGS. 6A-6D illustrates the use of a shape-memory structure, such as a nitinol wire 60 within an elastomeric insulator 61, and which serves as an actuator 50 that is attached to the band 42. Three nitinol wire actuators 50 are utilized, as illustrated in FIG. 6A; however, various numbers of actuators 50 may be utilized in other embodiments.

The nitinol will switch between two different crystal structures upon application of thermal energy, such as that which may be caused by running an electric current along the wire. In the configuration of FIG. 6, the nitinol wire 60 may expand or contract by varying electric current applied thereto from a power source, for example, a power source within the housing 44 of the watch 40. FIG. 6C illustrates the actuator(s) 50 in an extended configuration and FIG. 6B illustrates the actuator(s) 50 in a retracted configuration. The electrical current from the power source applied across the nitinol wire 60 would preferably be modulated in time, such as with pulse-width modulation circuitry or some other pulsing circuitry, to prevent overheating of the wire 60, which would potentially occur under DC (continuous) electrical current. When in the retracted configuration, the actuator(s) 50 cause the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

In some embodiments, the band 42 may include an electro active polymer (EAP) material that changes shape and/or size with electrical stimulation. Such EAPs may be comprised of ferroelectric, piezoelectric, electrostatic and/or electrostrictive polymers, or the like. Thus, the actuation of the band 42 may be activated or deactivated by via controlling the voltage potential across the EAP. The EAP may also be operated in reverse. For example, the EAP may be configured to convert mechanical energy from motion into electrical energy, which may be used for energy harvesting (for powering the watch itself) or may be used for improving the mechanical stability of the band 42 on an appendage. For example, the improvement in stability may be caused by forces applied to the EAP in the band 42 during exercise, and by converting excess mechanical energy to electricity, this may help prevent mechanical vibrations in the band 42. This may provide a significant kinetic advantage over traditional sources based upon smaller mass/momentum systems by using the full momentum of the entire wristwatch to stretch and elongate the EAP band 42.

Figure 7A:
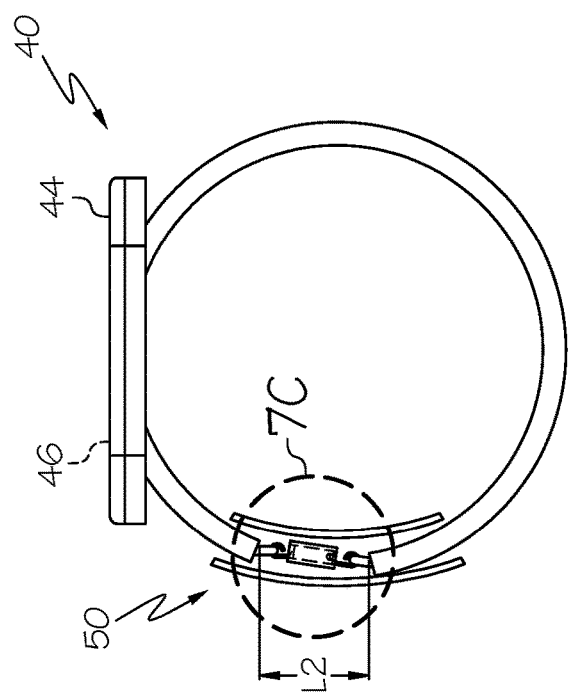
FIGS. 7A-7C illustrate an actuator that incorporates a gel that can expand and contract in the presence of light and that can be utilized with various monitoring devices, such as the monitoring devices illustrated in FIGS. 2A-2J, 3A-3B, 4A-4B and 5A-5D, according to some embodiments of the present invention.
Figure 7B:
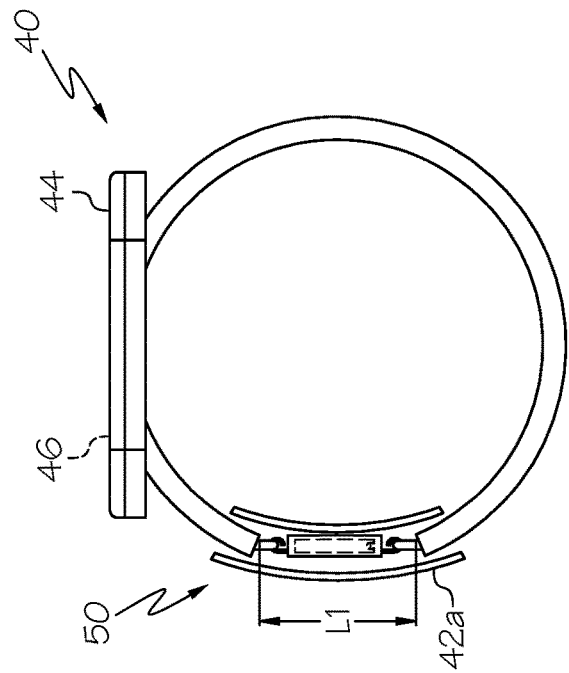
Figure 7C:
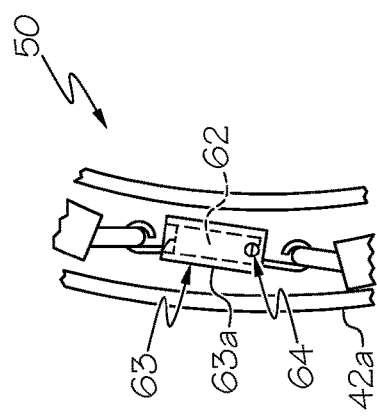
Figure 8B:
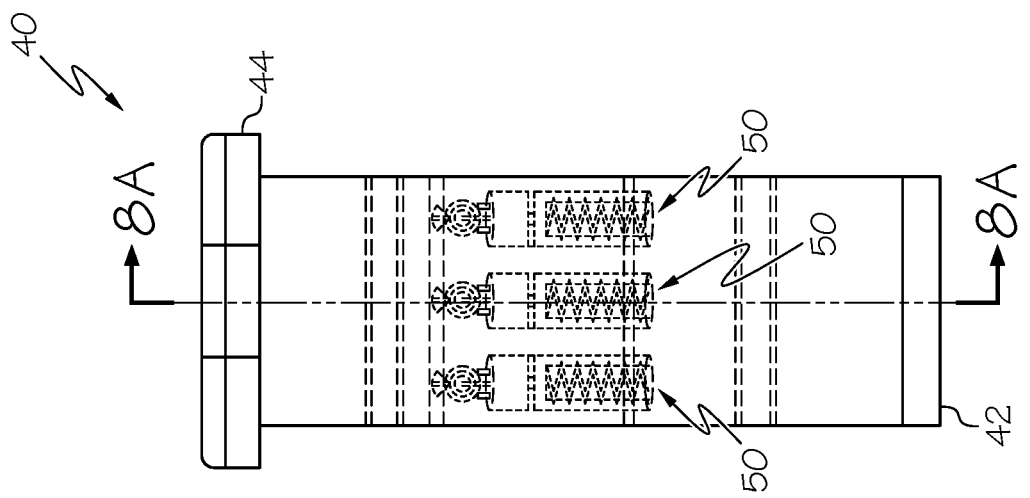
Figure 8A:
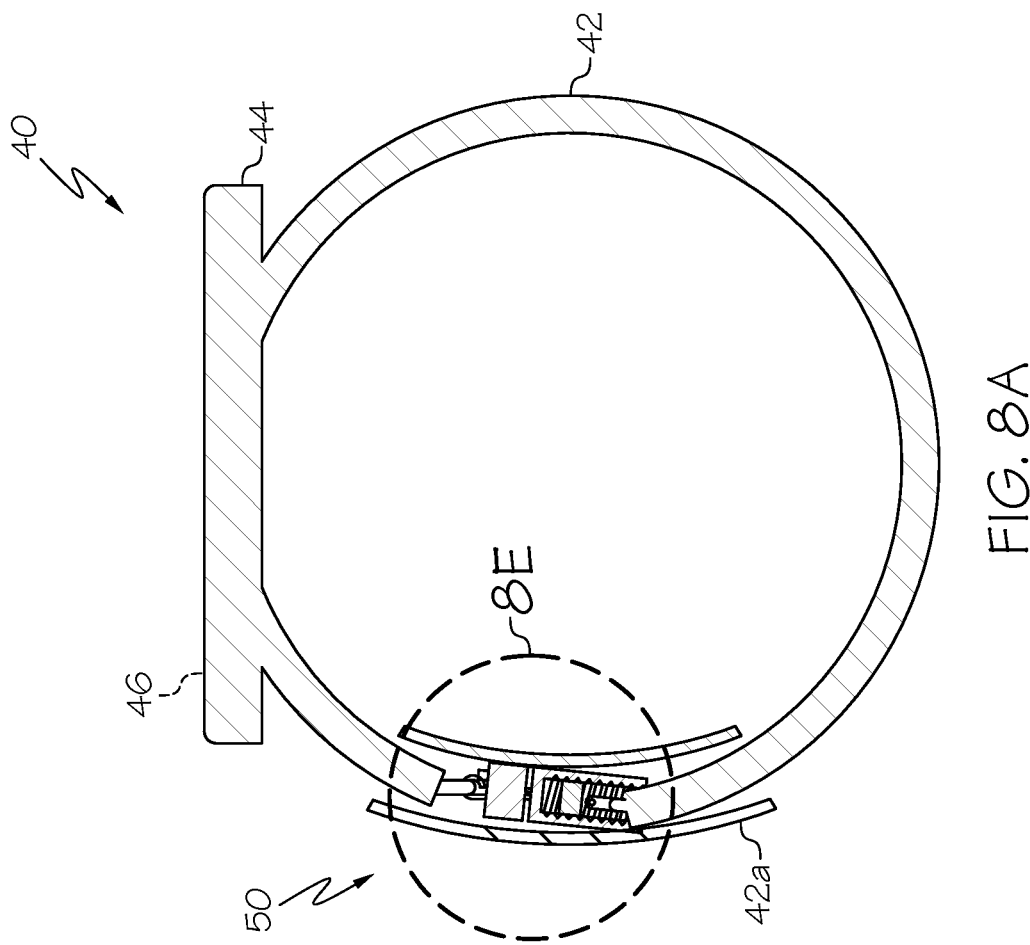

FIGS. 7A-7C illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes an actuator 50 attached to the band 42 as illustrated, and that incorporates a gel 62 within an elastomeric tube 63. The gel 62 is configured to expand or contract in the presence of light from a light source 64. The light source 64 is powered via a power source, such as a power source within the housing 44 of the watch 40. Examples of suitable light sources may include, but are not limited to light-emitting diodes (LEDs), organic LEDs (OLEDs), microplasma sources, incandescent sources, luminescent sources (such as fluorescent or phosphorescent sources), lasers (such as laser diodes), or the like.

In some embodiments, the tube 63 includes a rigid sleeve 63a that contains the gel 62 and the rigid sleeve 63a prevents radial expansion of the gel 62 and elastomeric tube 63. Three actuators 50 are illustrated; however, various numbers of the gel/elastomeric tube actuators 50 may be utilized. FIG. 7B illustrates an actuator 50 in an extended configuration and FIG. 7A illustrates the actuator 50 in a retracted configuration. When in the retracted configuration, the actuator 50 causes the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration. Moreover, various numbers of actuators 50 can be utilized including a single actuator 50.

FIGS. 8A-8E illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes electromechanical devices utilized as actuators 50 that are attached to the band 42, as illustrated. In the illustrated embodiment, three actuators 50 are illustrated; however, various numbers of the electromechanical actuators 50 may be utilized, including a single actuator.

In the illustrated embodiment, each actuator 50 includes an electrical motor 66 that rotates a threaded sleeve 67 and threaded member 68 relative to each other such that the threaded member 68 can extend and retract. The electrical motor 66 has a power connection 69 that receives electrical power from a power source, such as a power source within the housing 44 of the watch 40. FIG. 8D illustrates an actuator 50 in an extended configuration (i.e., band 42 is in a relaxed state) and FIG. 8C illustrates the actuator 50 in a retracted configuration. When in the retracted configuration, the actuators 50 cause the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

Figure 9B:
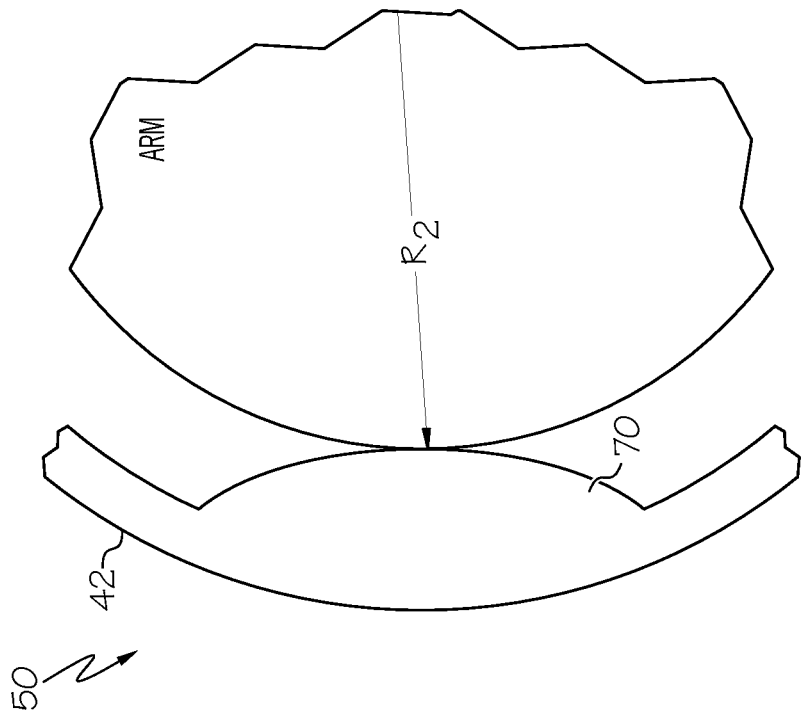
FIGS. 9A-9B illustrate an actuator that incorporates a bladder that can be expanded and retracted and that can be utilized with various monitoring devices, such as the monitoring devices illustrated in FIGS. 2A-2J, 3A-3B, 4A-4B and 5A-5D, according to some embodiments of the present invention.
Figure 9A:
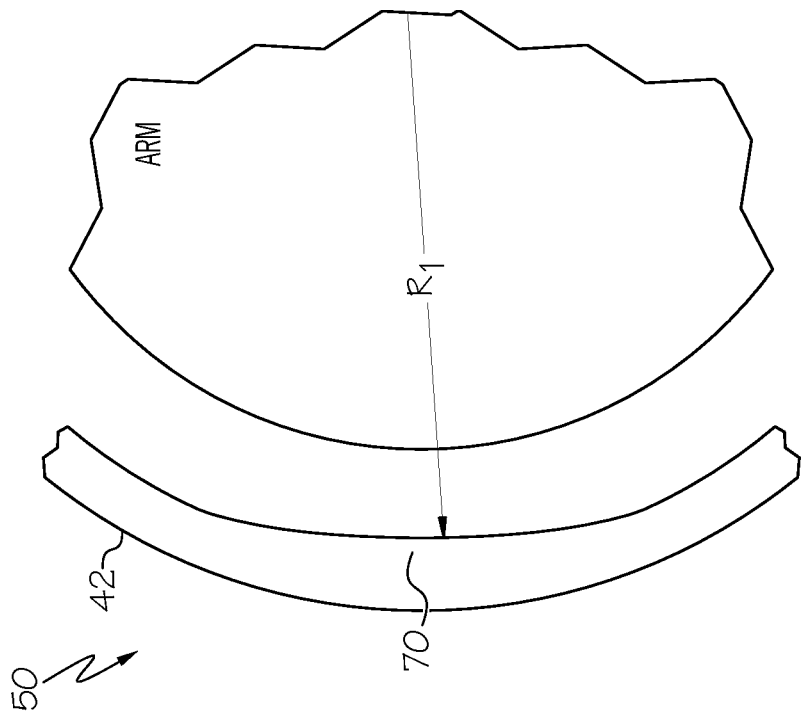

FIGS. 9A-9B illustrate another actuator 50 that can be utilized with a monitoring device according to embodiments of the present invention, such as the watch 40 of FIGS. 5A-5D. The illustrated actuator 50 is a bladder 70 that can be expanded and retracted, for example, via air or other gas/fluid. One or more of the bladders 70 can be provided on the band 42 of the watch 40 illustrated in FIGS. 5A-5D. FIGS. 9A and 9B are only partial illustrations of a band incorporating the bladders 70 and it is understood that a plurality of bladders can be utilized.

FIG. 9A illustrates the bladder 70 in a retracted configuration and FIG. 9B illustrates the bladder 70 filled with a gas/fluid to cause the bladder 70 to expand. When expanded, the bladder 70 causes the band 42 to fit snugly around an arm of a subject. R1 is the radius from the centerline of an appendage (e.g., arm, etc.) to the inner surface of the band 42 when the bladder 70 is not inflated and R2 is the radius from the centerline of the appendage to the inner surface of the band 42 when the bladder 70 is inflated. R2 is shorter in length than R1 because of the inflation of bladder 70.

It should be noted that a liquid metal, eutectic metal alloy, or other electrically conductive alloy may also be used within the bladder 70 to inflate or deflate the bladder 70 of FIGS. 9A-9B. As a specific example, the bladder 70 may be filled with a eutectic liquid (at room temperature) metal alloy comprising gallium and indium, or a solution of the alloy in a liquid (such as water). In such a material or solution, the application of a voltage across the alloy, or across the alloy submerged in a liquid (such as water or other fluid), can cause a substantial reduction in surface tension of the liquid metal, changing its shape. The voltage or potential drop required to reduce the surface tension across the alloy or alloy and liquid may be on the order of just one volt (1V), suitable for consumer electronic devices. By removing the voltage, the surface tension may return, allowing the alloy to revert to its high-surface-tension shape.

The application of embedded electrically active alloys may also be used to control the shape of the shape-changing earbuds 20 of FIGS. 2A-2D and more broadly the stability control of appendage bands 30 (i.e., wrist, arm, leg, digit, etc.) as shown in FIGS. 4A-4B. In such designs, the insides of the earbuds or bands may comprise a bladder region filled with an electrically active alloy (as described above) or an alloy and liquid, with electrodes applied across the alloy or the alloy and liquid. The liquid may be water, a water based solution, or other liquid which can be used to help control the oxidation of the alloy upon an applied voltage across the electrodes. The electrodes may be in communication with an electrical driving circuit, in communication with a processor, for controlling the potential across the electrodes, and this driving circuit and processor may be located on the earbud or band itself. In general, a voltage across the alloy or the alloy and liquid will result in decrease in surface tension, resulting in a flattening of the alloy. When in a band or earbud, this flattening may reduce the stability of the band or earbud on the body of a person. However, this invention may be used to manipulate the shape of the band or earbud in general, to either expand or contract with electrical stimulation, depending on the mechanical coupling between the alloy and the housing or band of the wearable device.

FIGS. 10A-10E illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc.

The monitoring device/watch 40 includes a plurality of actuators 50 (FIG. 10B) attached to the band 42 as illustrated, and each actuator incorporates a linear bladder 72 that can be retracted when inflated and extended when deflated. In the illustrated configuration, three bladder actuators 50 are utilized; however, various numbers of actuators 50 may be utilized in other embodiments, including a single actuator 50.

As shown in FIG. 10E, each bladder 72 is surrounded by a mesh expansion sleeve 73, although other types of expansion sleeve/materials may be utilized. A pneumatic connector 74 is in fluid communication with the bladder 72 and is configured to be connected to a gas/fluid source, such as a source within the housing 44 of the watch 40. FIG. 10D illustrates a bladder actuator 50 in a relaxed, uninflated, length extended configuration and FIG. 10C illustrates the bladder actuator 50 in an actuated (i.e., bladder inflated, length reduced) configuration. When in the bladder inflated configuration, the bladder actuator 50 causes the band 42 to contract and fit snugly around an arm of a subject. In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

Figure 11B:
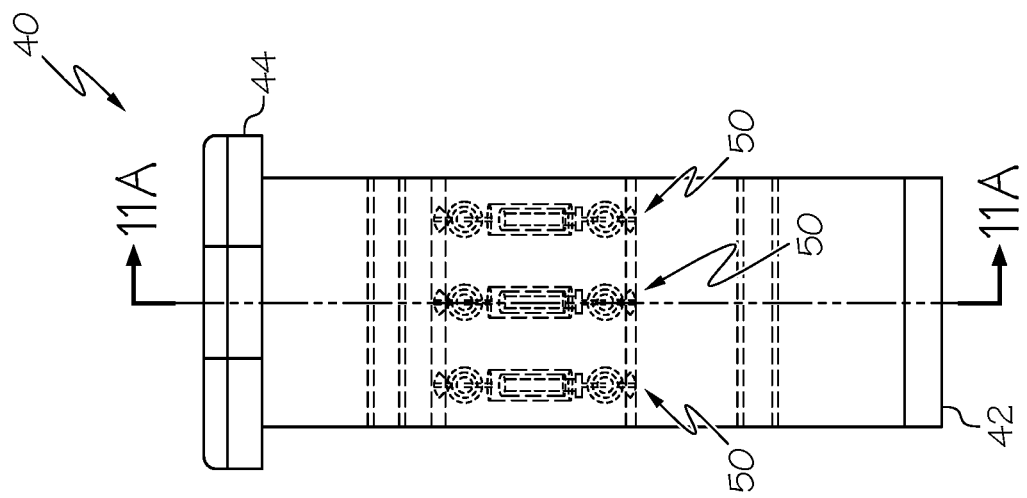
FIGS. 11A-11E illustrate a pneumatic cylinder that extends and retracts and that can be utilized as an actuator with various monitoring devices, such as the monitoring devices illustrated in FIGS. 2A-2J, 3A-3B, 4A-4B and 5A-5D, according to some embodiments of the present invention.
Figure 11A:
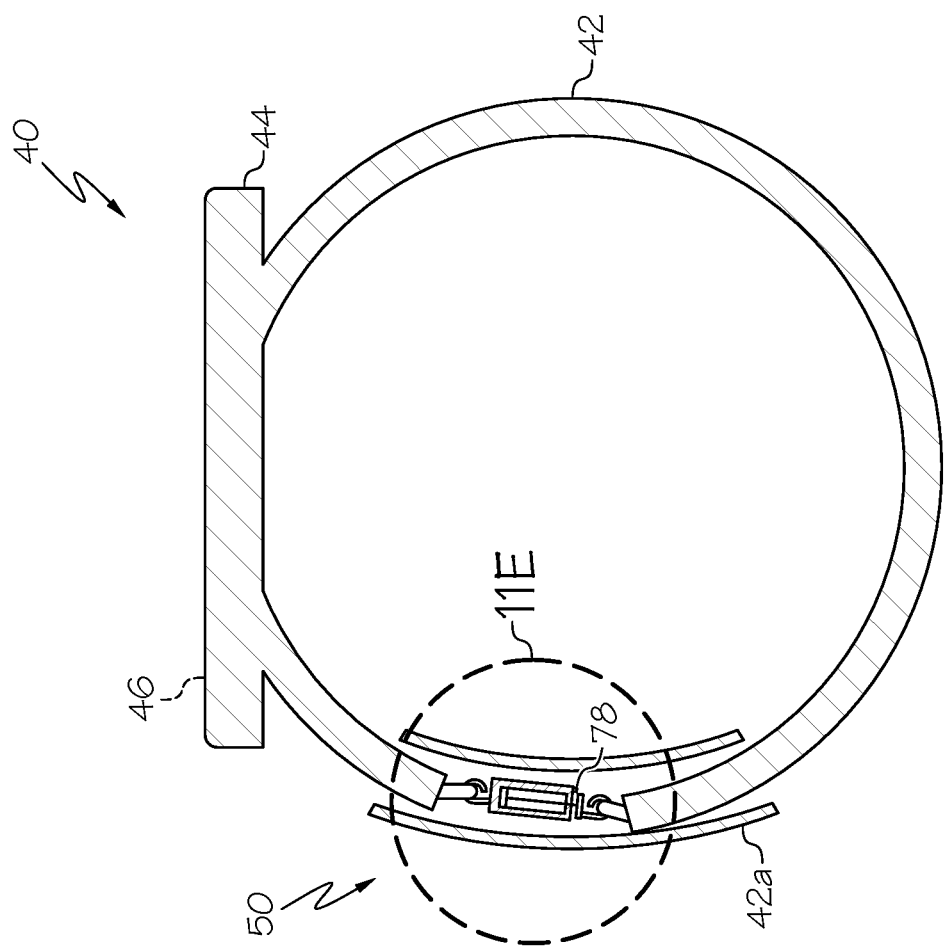
Figure 11D:
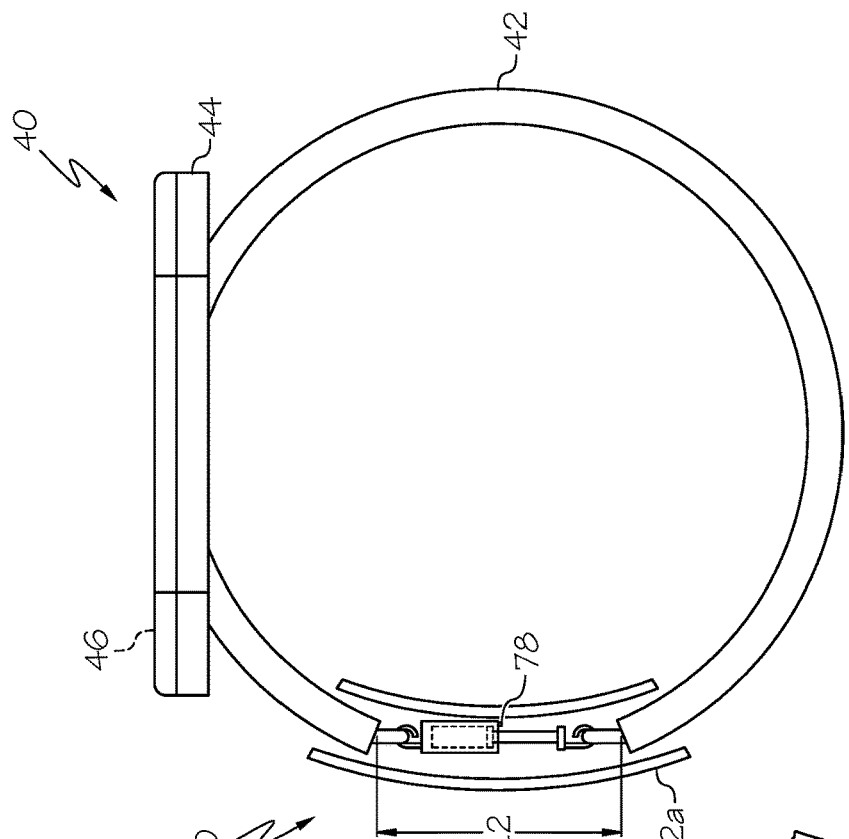
Figure 11E:
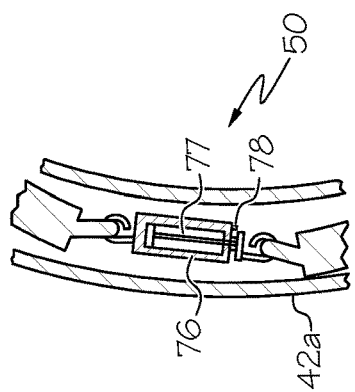
Figure 11C:
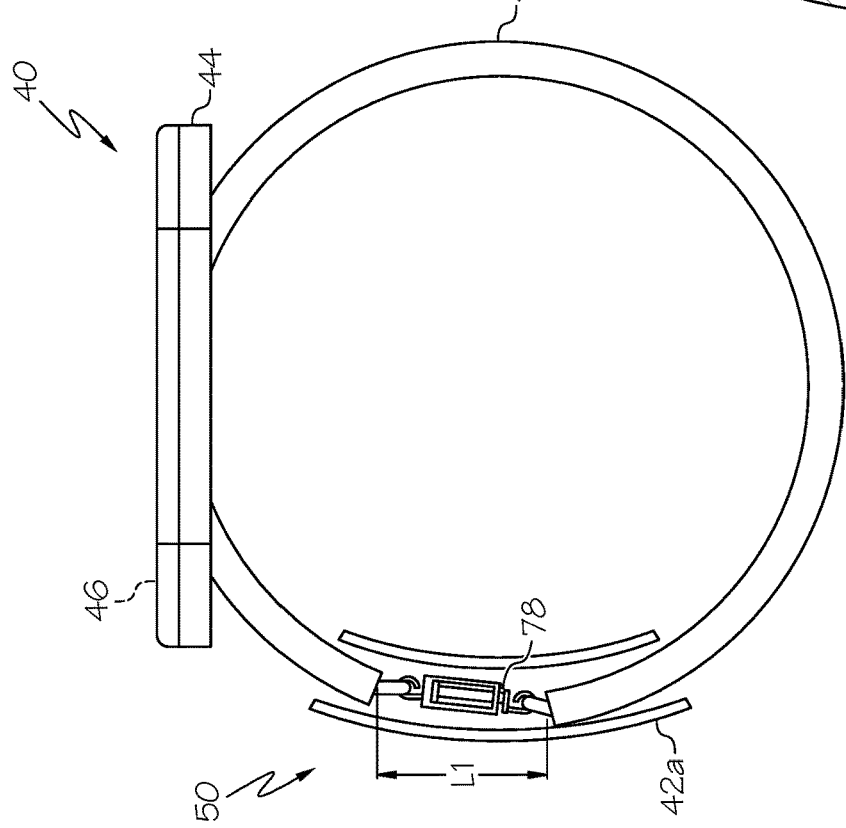

FIGS. 11A-11E illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes a plurality of actuators 50 (FIG. 11B) attached to the band 42 as illustrated, and each actuator incorporates a pneumatic cylinder 76 and a piston 77 movable within the cylinder 76. The piston 77 can be extended and retracted via the application and removal of air or other gas. In some embodiments, the cylinder and piston may be a hydraulic cylinder and piston and wherein the piston can be extended and retracted via the application and removal of fluid. A pneumatic connector 78 is in fluid communication with the bladder cylinder 76 and is configured to be connected to a gas/fluid source, such as a source within the housing 44 of the watch 40. Three cylinder/piston actuators 50 are utilized, as illustrated in FIG. 11B; however, various numbers of cylinder/piston actuators 50 may be utilized in other embodiments, including a single actuator 50. FIG. 11D illustrates an actuator 50 in an extended configuration and FIG. 11C illustrates the actuator 50 in a retracted configuration. When in the retracted configuration, the actuator 50 cause the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

Figures 12A, 12B:
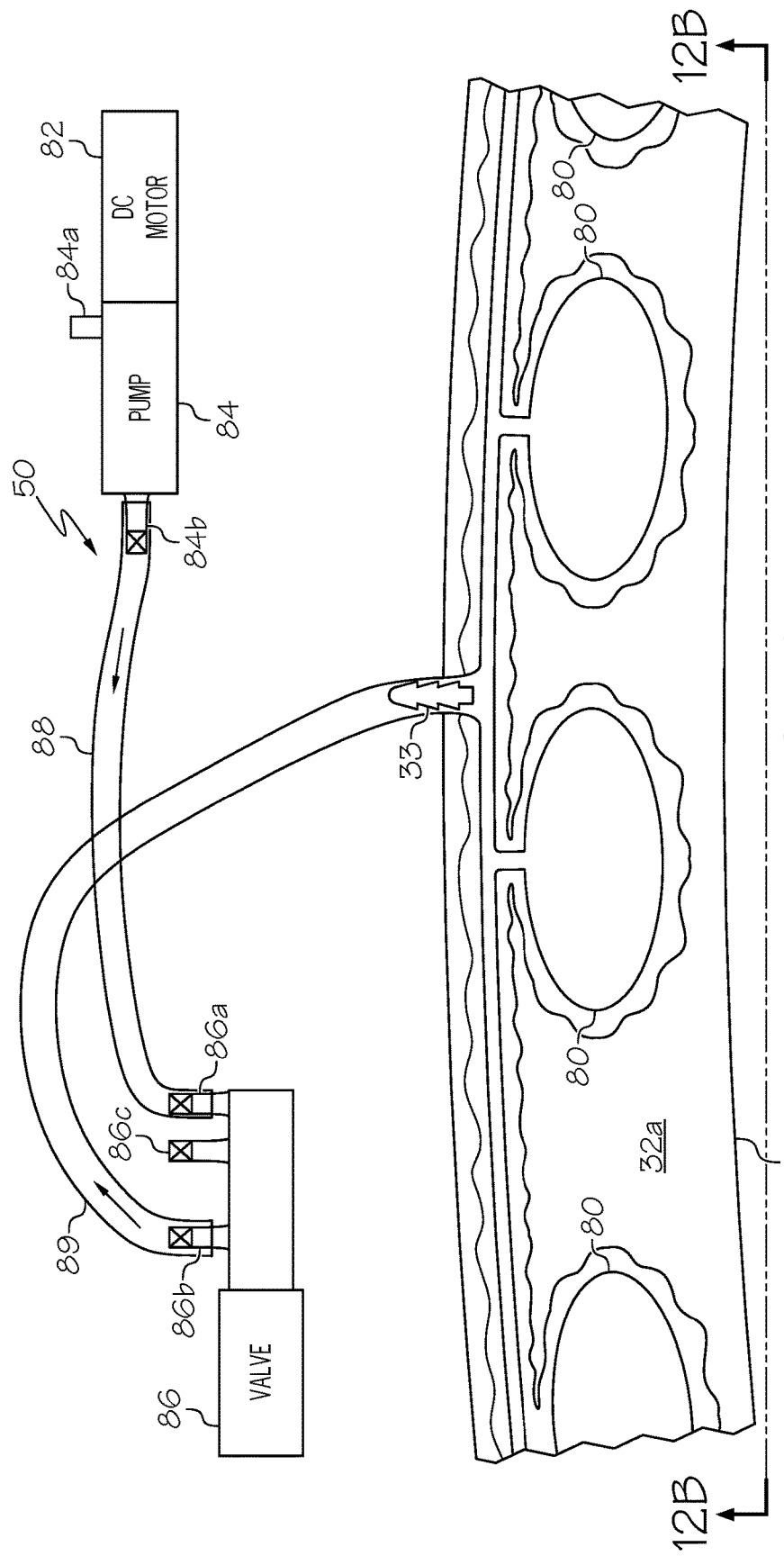
FIGS. 12A-12B illustrate an actuator that incorporates multiple bladders that can be expanded and retracted and that can be utilized with various monitoring devices, such as the monitoring devices illustrated in FIGS. 2A-2J, 3A-3B, 4A-4B and 5A-5D, according to some embodiments of the present invention.

FIGS. 12A-12B illustrate an actuator 50 that incorporates multiple bladders that can be expanded and retracted and that can be utilized with various monitoring devices according to embodiments of the present invention. FIG. 12A illustrates the bladders uninflated and FIG. 12B illustrates the bladders inflated. The actuator 50 can be integrated with a sensor band, such as the sensor band 32 of FIGS. 3A-3B and 4A-4B. When the bladders 80 are retracted or uninflated, the band 32 can fit loosely around an appendage (e.g., an arm, wrist, hand, finger, toe, leg, foot, neck, etc.) of a subject. When the bladders 80 are expanded or inflated, the band 32 fits snugly around the appendage.

In the illustrated embodiment, a motor (e.g., a DC motor) 82 is provided that operates a pump 84 for pumping air (or other gas/fluid) into the bladders 80 to cause the bladders 80 to expand. The pump 84 includes an air inlet 84a and an air outlet 84b. A valve 86 is also provided to facilitate the expansion and retraction of the bladders 80. The valve 86 includes an air inlet 86a, and air outlet 86b, and an air exhaust port 86c. Tubing 88 connects the pump air outlet 84b and the valve air inlet 86a, and tubing 89 connects the valve air outlet 86b with an inlet port 33 of the sensor band 32. The pump causes air to flow through tubing 88, through the valve, through the tubing 89 and into the bladders 80 to expand the bladders 80. To retract the bladders 80, the valve exhaust port 86c can be opened to allow the air to escape therefrom. Alternatively, the pump 84 can be reversed to remove the air from the bladders 80 in order to cause them to retract.

Figure 13B:
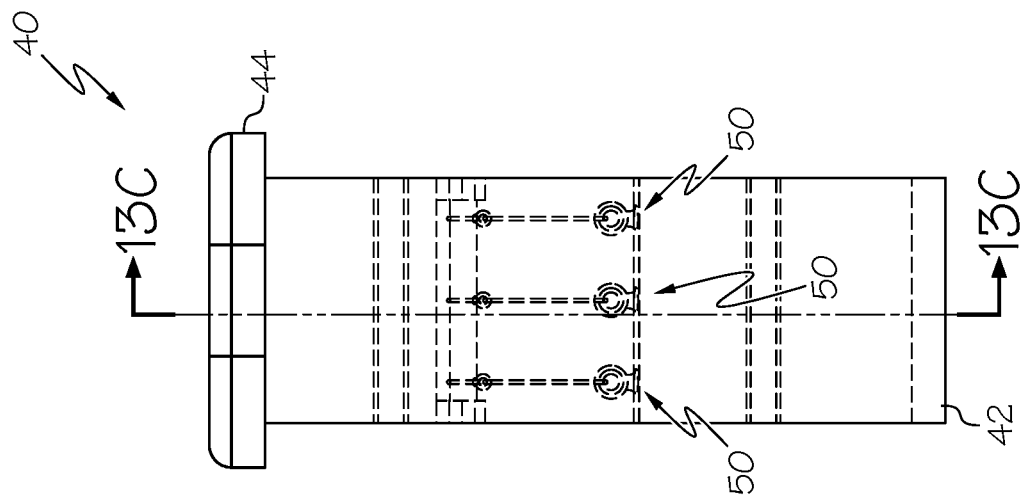
FIGS. 13A-13F illustrate an actuator that incorporates a motor and a mandrel for winding thread/fabric therearound and that can be utilized with various monitoring devices, such as the monitoring devices illustrated in FIGS. 2A-2J, 3A-3B, 4A-4B and 5A-5D, according to some embodiments of the present invention.
Figure 13A:
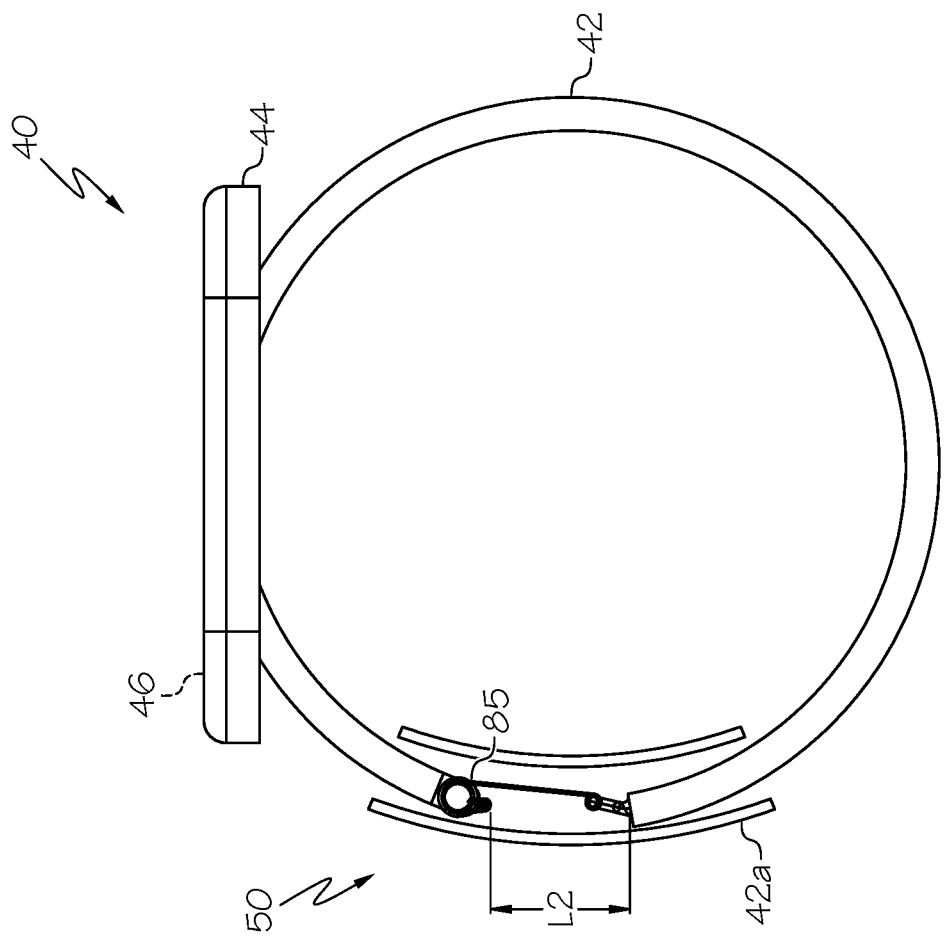
Figure 13D:
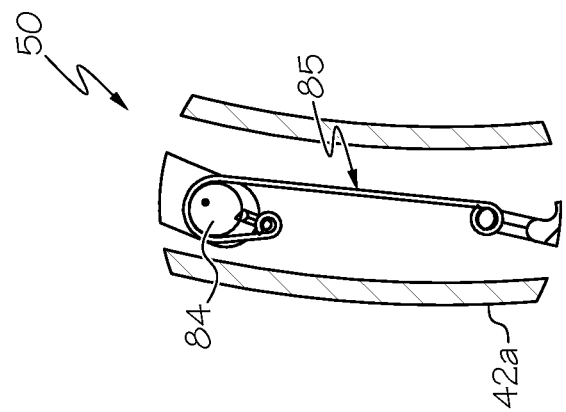
Figure 13C:
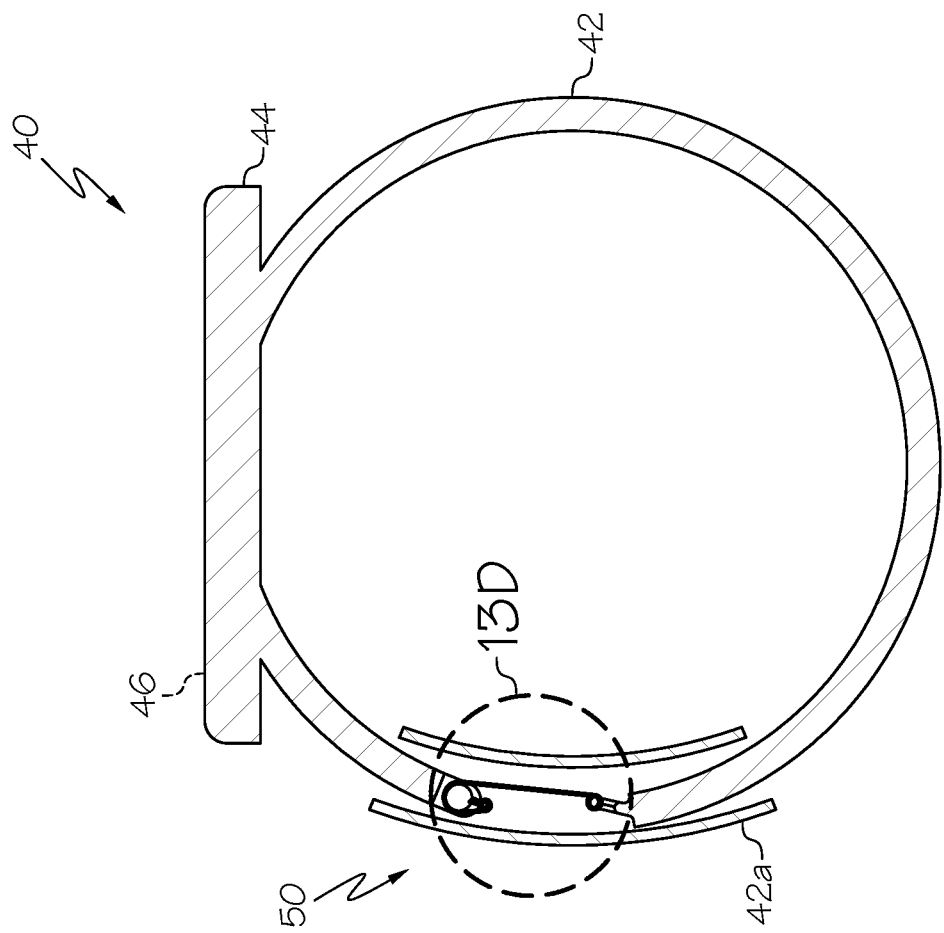
Figure 13F:
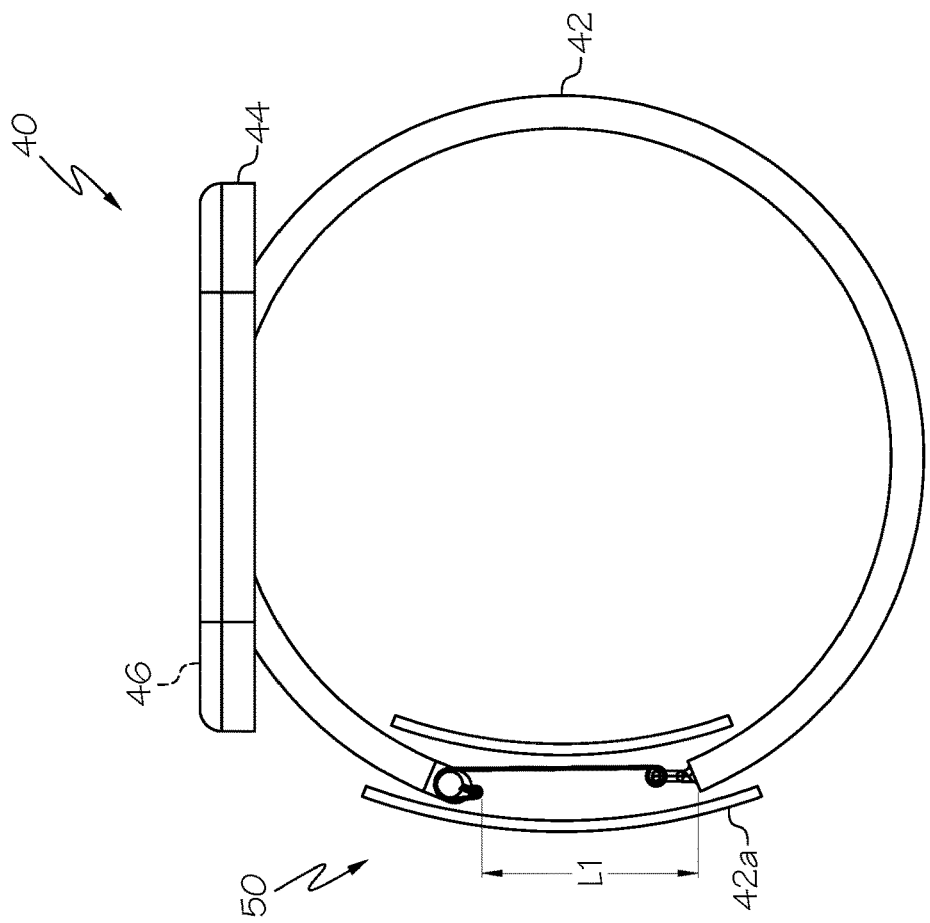
Figure 13E:
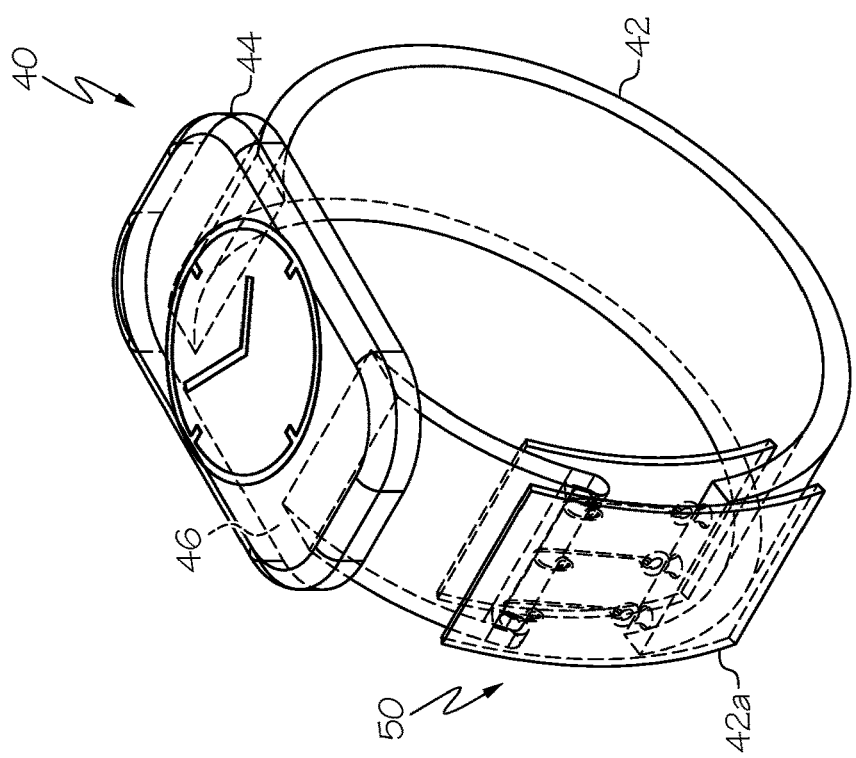

FIGS. 13A-13F illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes a plurality of actuators 50 (FIG. 13B) attached to the band 42 as illustrated, and each actuator incorporates a motor having a mandrel or spindle 84 for winding threads/fabric 85 therearound, as illustrated in FIG. 13D. Rotation of the mandrel 84 via the motor causes the threads/fabric 85 to wind around the mandrel 84, which causes the threads/fabric 85 to tighten. Reversal of the motor causes the threads/fabric 85 to unwind from the mandrel 84, which causes the threads/fabric 85 to loosen. The actuator 50, in some embodiments, may include a spring (not shown) that facilitates unwinding of the threads/fabric 85 from the mandrel 84. In some embodiments, the actuator 50 may include a solenoid device (not shown) for latching which is utilized to maintain the actuator 50 in a wound and/or unwound state. Three actuators 50 are utilized, as illustrated in FIGS. 13B and 13E; however, various numbers of actuators 50 may be utilized in other embodiments, including a single actuator 50.

FIG. 13F illustrates the actuator 50 in an extended configuration (i.e., wherein the band 42 is relatively loose) and FIG. 13A illustrates the actuator 50 in a retracted configuration (i.e., wherein the thread/fabric 85 has been wound around the mandrel 84). When in the retracted configuration, the actuator 50 causes the band 42 to contract and fit snugly around an arm of a subject. In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

Figure 13G:
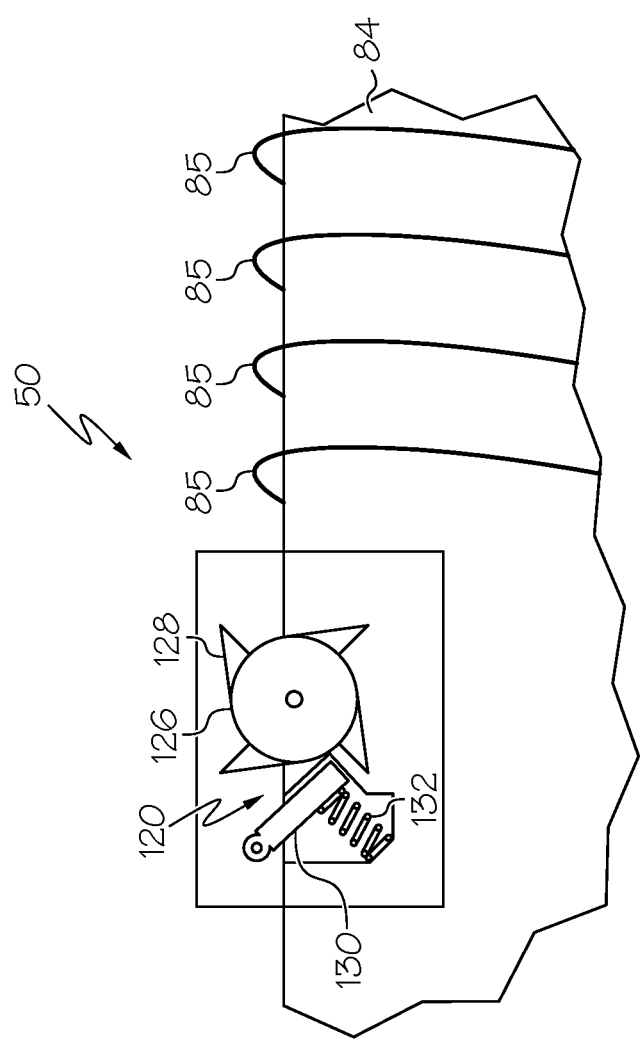
FIG. 13G illustrates a ratchet mechanism that may be utilized with the actuator of FIGS. 13A-13F, according to some embodiments of the present invention.

FIG. 13G illustrates a ratchet mechanism 120 that may be utilized with the actuators 50 of FIGS. 13A-13F. The ratchet mechanism 120 is coupled to each mandrel 84 and includes a gear 126 with angled teeth 128, a pawl 130 and spring 132. The spring 132 urges the pawl 130 into contact with the gear 126 allowing motion in one direction only (i.e., allowing the mandrel 84 to rotate so that the threads/fabric 85 become tightened). To release the tension on the threads/fabric 85, the spring 132 is released from the pawl 130 so that the pawl does not engage the teeth 128 and so that the gear 126 and mandrel 84 can reverse direction, as one with skill in the art would understand.

FIGS. 14A-14B illustrate another actuator 50 that may be utilized in conjunction with a band of a monitoring device, such as the monitoring device/watch 40 of FIGS. 5A-5D. The actuator 50 incorporates material that undergoes a phase change when exposed to temperature variations. Broadly speaking, the phase change material can be any material that changes phase upon a change in thermal energy transfer (i.e., wax, salt hydrates, water, organic oils, polymers, metals or metallic materials, micro- or nano-structured materials, etc.). In some embodiments, the material is a phase change material that vacillates between phases in the range of 0° C. to 100° C.

The illustrated actuator 50 includes a one way valve 88 that is normally closed, but opens to facilitate movement of the phase change material upon the change of phase. Applying or removing thermal energy to the phase change material 89 in the apparatus can cause extension or retraction of a portion 90 of the actuator 50, depending on the phase change material being used. In some embodiments, natural leakage of the phase change material 89 through a valve (such as valve 88) can be used to allow the actuator to retract (i.e., relax).

In some embodiments, the apparatus of FIGS. 14A-14B may include a magnetostrictive ferrofluid, rather than a phase change fluid. In such case, the mechanism for actuation would not comprise thermal energy but rather magnetic energy, such as that provided by an electromagnetic coil. Application of a magnetic field orients the fluid in such a way to extend or retract the actuator portion 90. For both the case of a phase change material or magnetostrictive material, the one-way valve 88 may be used to enable a normally open or normally closed configuration. Namely, the combination of the air backed cylinder controlled with a one-way inlet valve coupled to an actuator controlled by the heat or electrical/magnetic energy may enable the cylinder to have essentially a near-zero-energy state adjustable fixed length. For example, for the case of the phase change material, once the desired actuator portion 90 location is reached, heat could be removed from the system and the phase change material would solidify thus fixing the extension position without the need for additional energy expenditure. Similarly, for the case of magnetostriction, the magnetostrictive material could be configured to enable fluid flow during a magnetic coil energization, but then have a restricted flow in a low power state (when the magnetic coil is deenergized) via a fixed magnetic field acting upon the magnetostriction location.

Figure 15B:
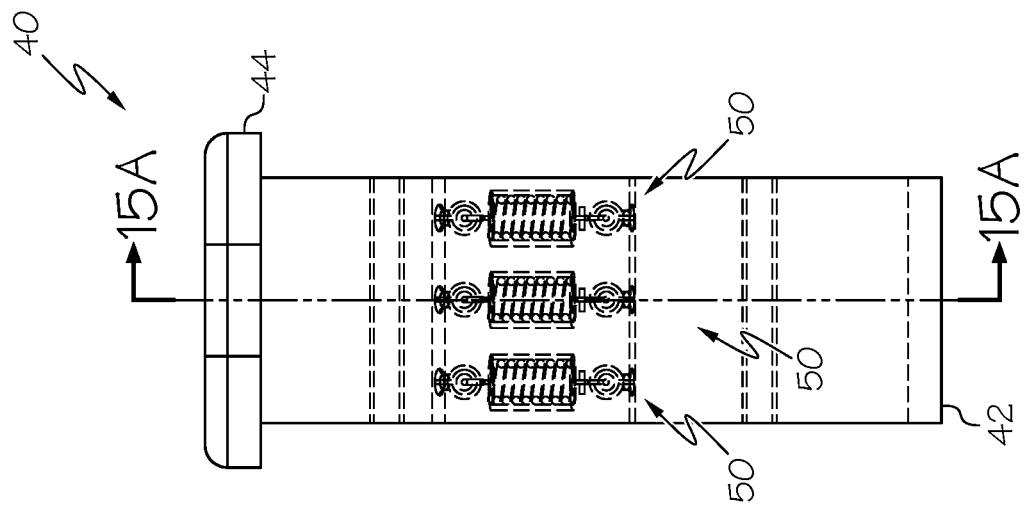
FIGS. 15A-15E illustrate an actuator that incorporates material that undergoes a phase change when exposed to temperature variations such that the actuator extends and retracts and that can be utilized with various monitoring devices, such as the monitoring devices illustrated in FIGS.
Figure 15A:
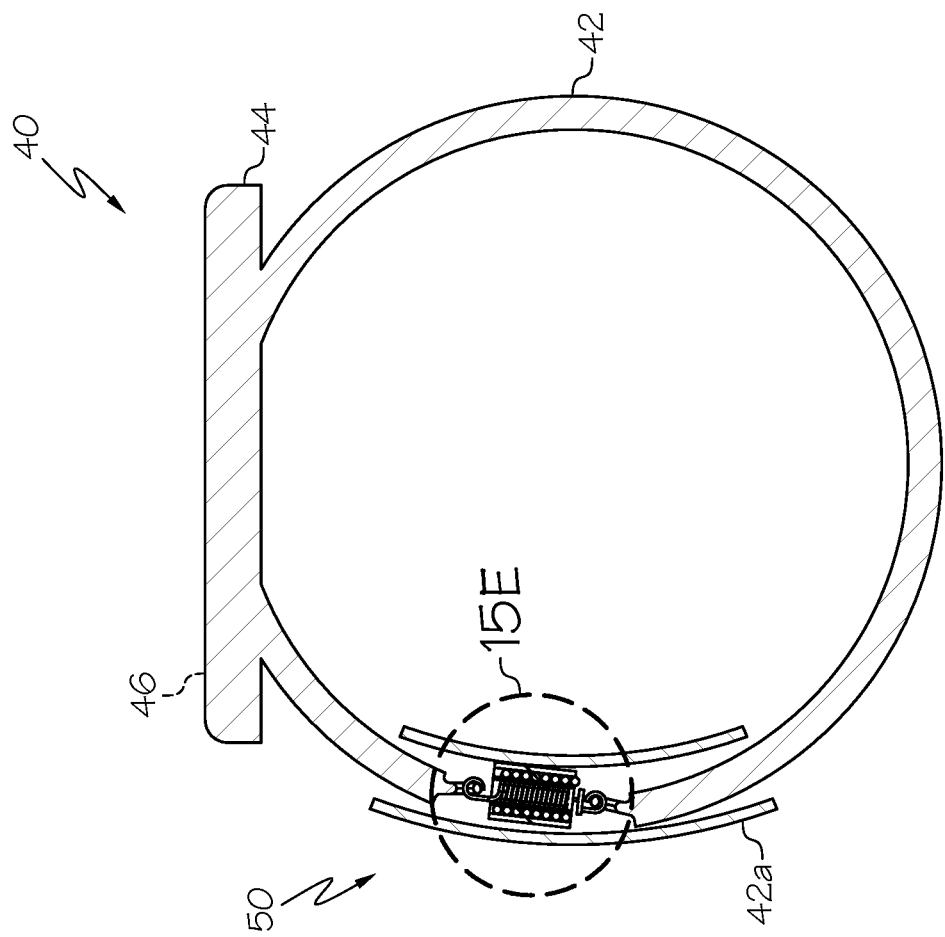
Figure 15D:
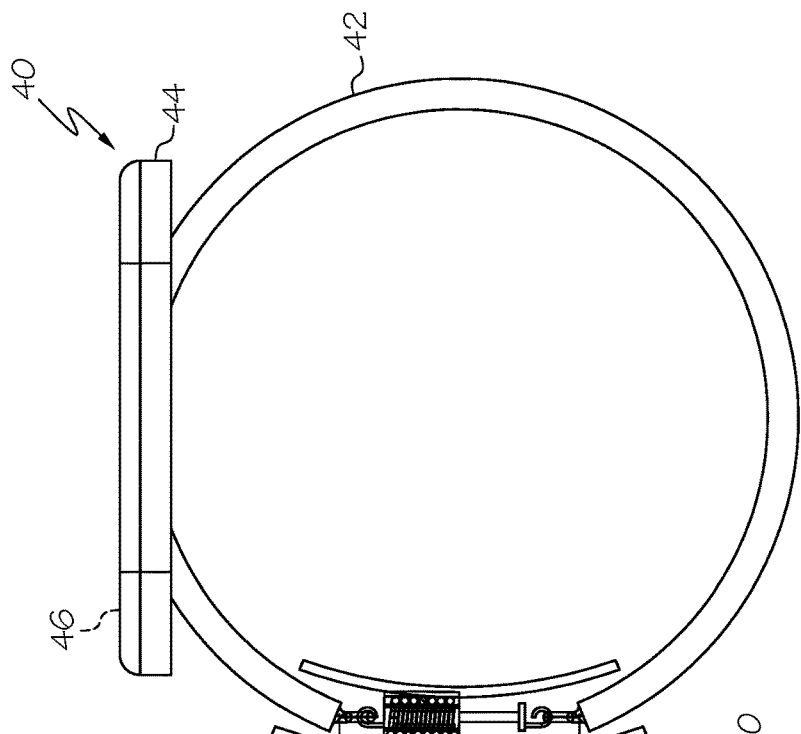
Figure 15E:
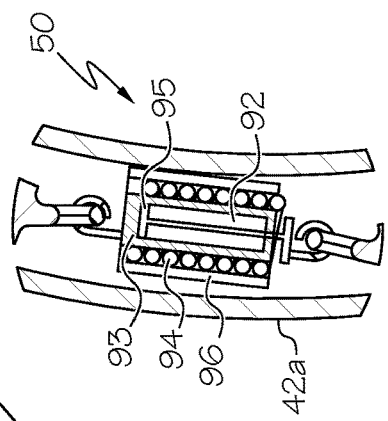

FIGS. 15A-15E illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes a plurality of actuators 50 (FIG. 15B) attached to the band 42 as illustrated, and each actuator 50 incorporates material 92 that undergoes a phase change when exposed to temperature variations. As illustrated in FIG. 15E, each actuator 50 includes a cylinder 93 containing a baffle and a heater coil 94 surrounding the cylinder 93. The heater coil 94 receives electrical power from a power source, such as a power source within the housing 44 of the watch 40. The cylinder 93 is filled with the phase change material 92 that causes a piston 95, such as a porous piston, to extend when the phase change material 92 is heated. Each illustrated actuator 50 is surrounded by an insulator 96.

Figure 15C:
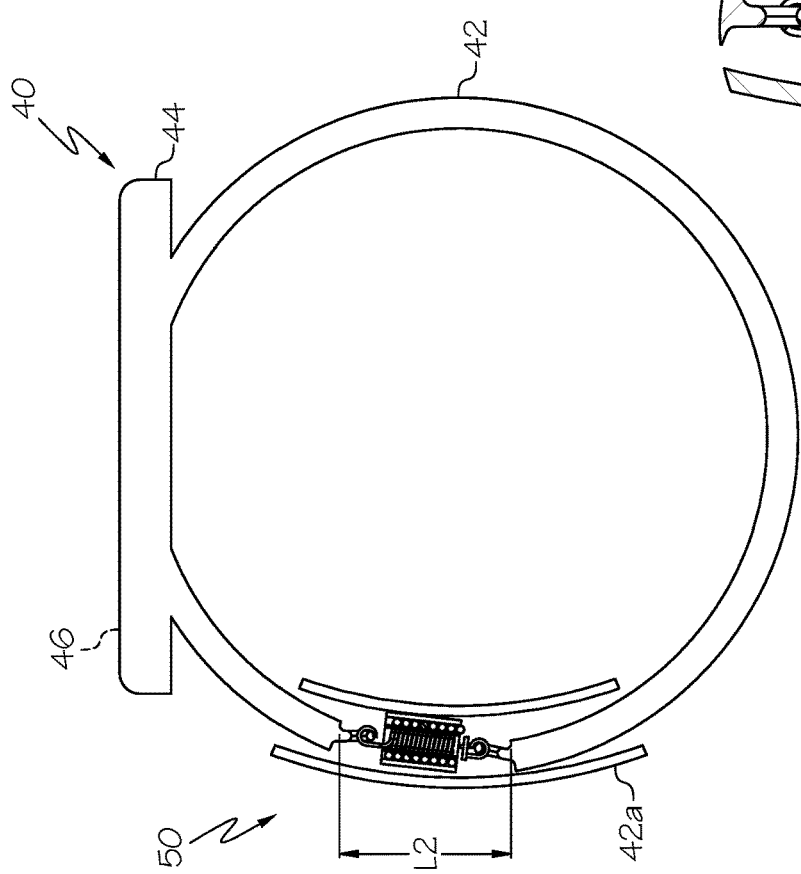

Three phase change material actuators 50 are utilized, as illustrated in FIG. 15B; however, various numbers of actuators 50 may be utilized in other embodiments including a single actuator 50. FIG. 15D illustrates an actuator 50 in an expanded configuration and FIG. 15C illustrates the actuator 50 in a retracted configuration. When in the retracted configuration, the actuator 50 causes the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

Figure 16E:
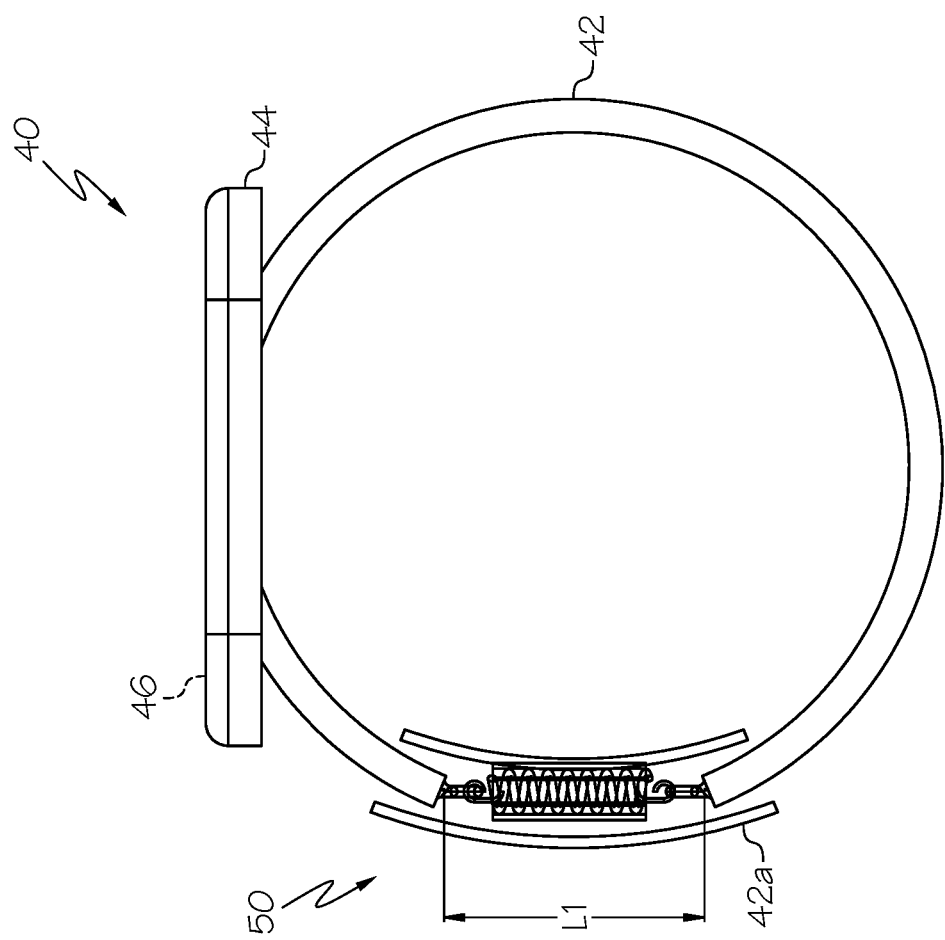

FIGS. 16A-16E illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes a plurality of actuators 50 (FIG. 16B) attached to the band 42 as illustrated, and each actuator 50 is an "artificial muscle" actuator that incorporates material, such as tightly wrapped polyethylene 100, and a heating element 101, as illustrated in FIG. 16D. Each illustrated actuator 50 is surrounded by an insulator 102. The polyethylene material 100 contracts when heated via the heating element 101 and expands when cooled, i.e., when current is not applied to the heating element 101. The heating element 101 receives electrical power from a power source, such as a power source within the housing 44 of the watch 40.

Three "artificial muscle" actuators 50 are utilized, as illustrated in FIG. 16B; however, various numbers of actuators 50 may be utilized in other embodiments including a single actuator 50. FIG. 16E illustrates an actuator 50 in an extended configuration and FIG. 16A illustrates the actuator 50 in a retracted configuration. When in the retracted configuration, the actuator 50 causes the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

FIGS. 17A-17B illustrate an actuator 50 that can be utilized with various monitoring devices, such as the monitoring devices illustrated in FIGS. 2A-2J, 3A-3B, 4A-4B and 5A-5D, according to some embodiments of the present invention. The illustrated actuator 50 incorporates shape memory polymer material 140. The material 140 retracts or shrinks when cold and expands when heated via a heating element, such as described above. FIG. 17B illustrates the actuator 50 in an extended configuration and FIG. 17A illustrates the actuator 50 in a retracted configuration. When in the retracted configuration, the actuator 50 causes a band (e.g., band 42, FIGS. 5A-5D) to contract and fit snugly around an arm or other appendage of a subject.

Figure 18B:
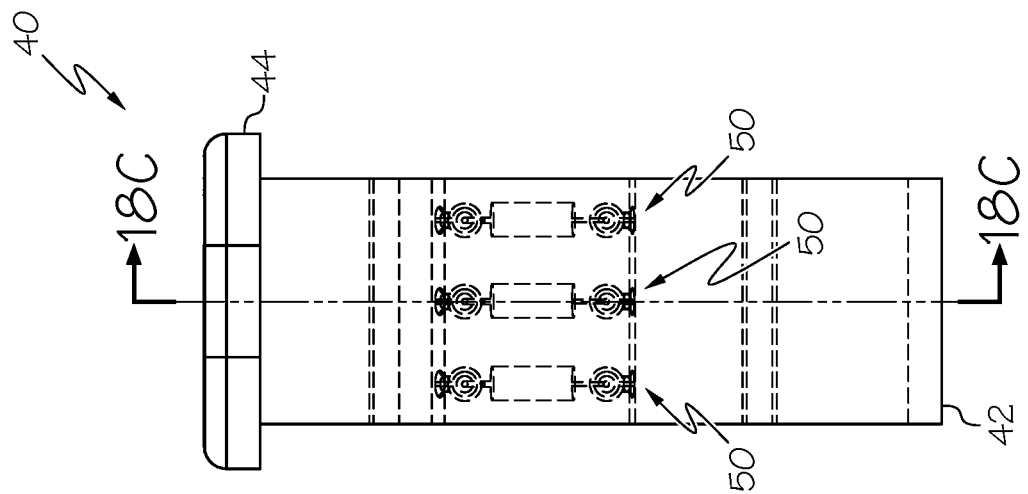

FIGS. 18A-18E illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The monitoring device/watch 40 includes a plurality of actuators 50 (FIG. 16B) attached to the band 42 as illustrated, and each actuator 50 incorporates a dielectric elastomer material or piezoelectric material 108, as illustrated in FIG. 18D. The material 108 expands and retracts based upon the change in voltage applied thereto via a power source, such as a power source within the housing 44 of the watch 40.

Figure 18A:
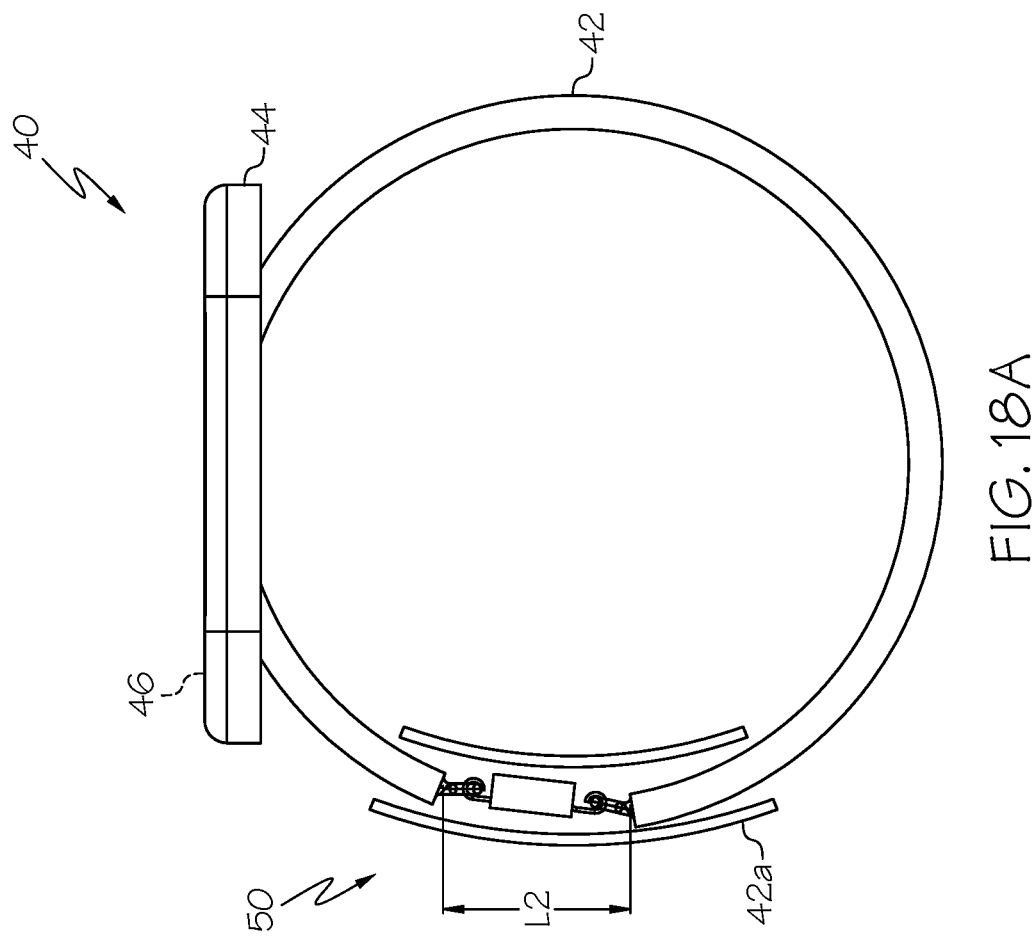
Figure 18E:
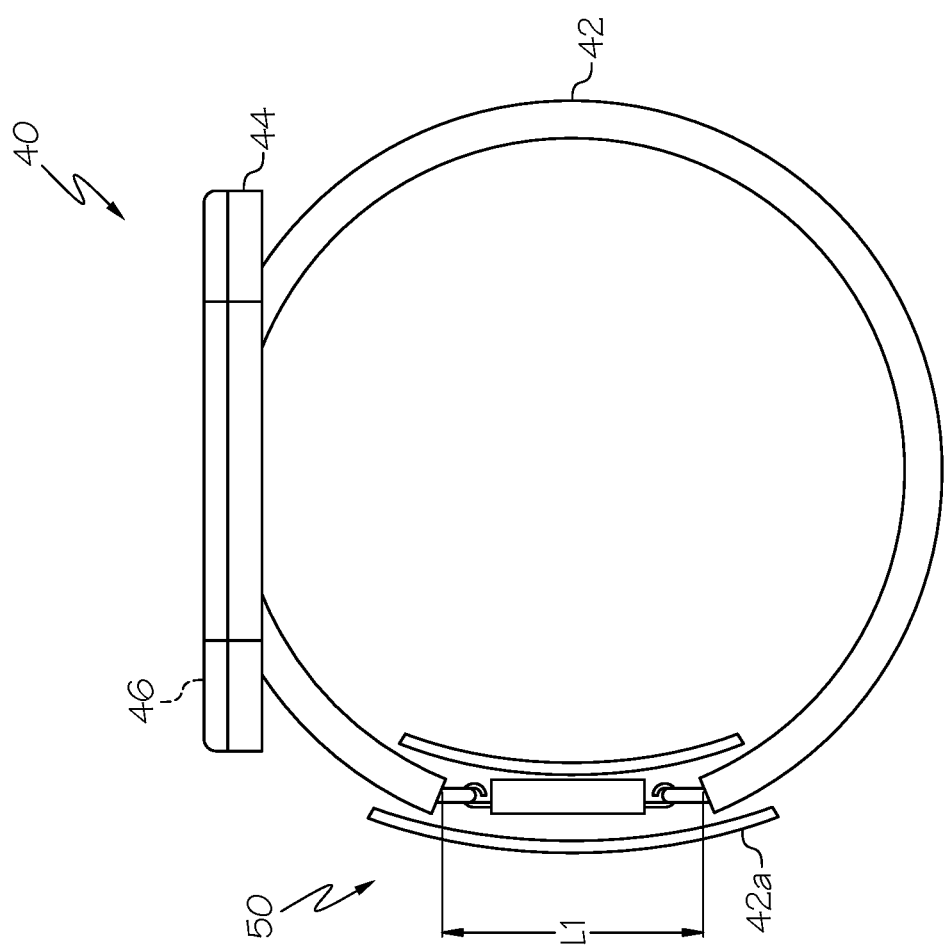

Three actuators 50 are utilized, as illustrated in FIG. 18B; however, various numbers of actuators 50 may be utilized in other embodiments including a single actuator 50. FIG. 18E illustrates an actuator 50 in an extended configuration and FIG. 18A illustrates the actuator 50 in a retracted configuration. When in the retracted configuration, the actuator 50 causes the band 42 to contract and fit snugly around an arm of a subject.

In the illustrated configuration, a sleeve 42a associated with the band 42 surrounds the actuators 50. The sleeve 42a is intended to protect the actuators 50 and to facilitate the changes in length of the band 42 due to activation and de-activation of the actuators 50. The actuators 50 can be incorporated and/or associated with the band 42 in various ways and are not limited to the illustrated configuration.

FIGS. 19A-19F illustrate a monitoring device/watch 40 that is configured to be worn on an arm of a subject via a band 42. The watch 40 includes a housing 44 secured to the band 42 and that includes one or more sensors 46 for measuring physiological information from a subject and/or one or more sensors for measuring environmental information in a vicinity of the subject, motion, and/or location, etc. The band 42 of the monitoring device/watch 40 includes a plurality of bladders 110 that can expand and retract, according to some embodiments of the present invention. The bladders 110 are circumferentially spaced apart along an inside surface 43 of the band 43 and are configured to expand against the arm of a wearer of the device to increase the tension or grip of the band 43 around the arm to thereby stabilize the device 40 relative to the arm when so desired.

Figure 19B:
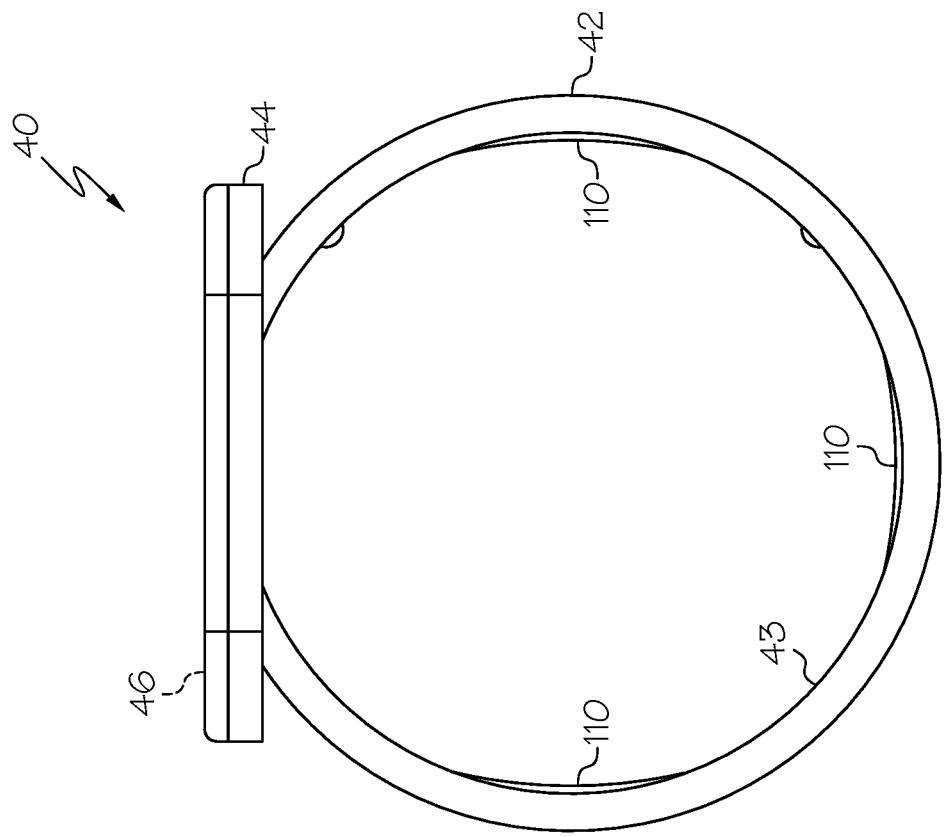
Figure 19A:
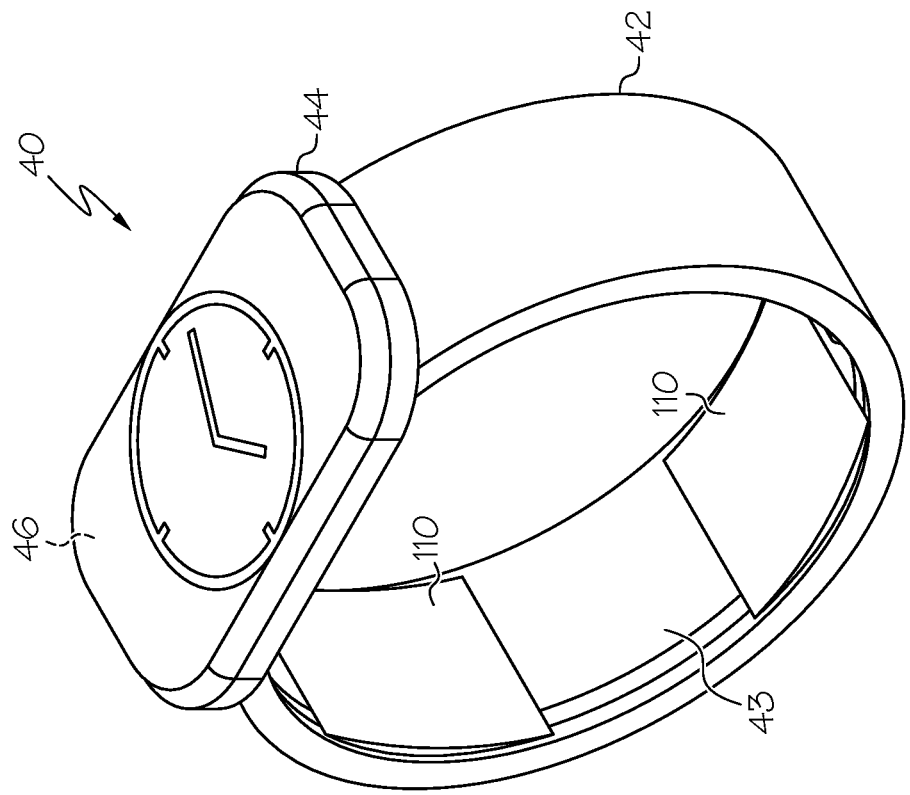
Figure 19D:
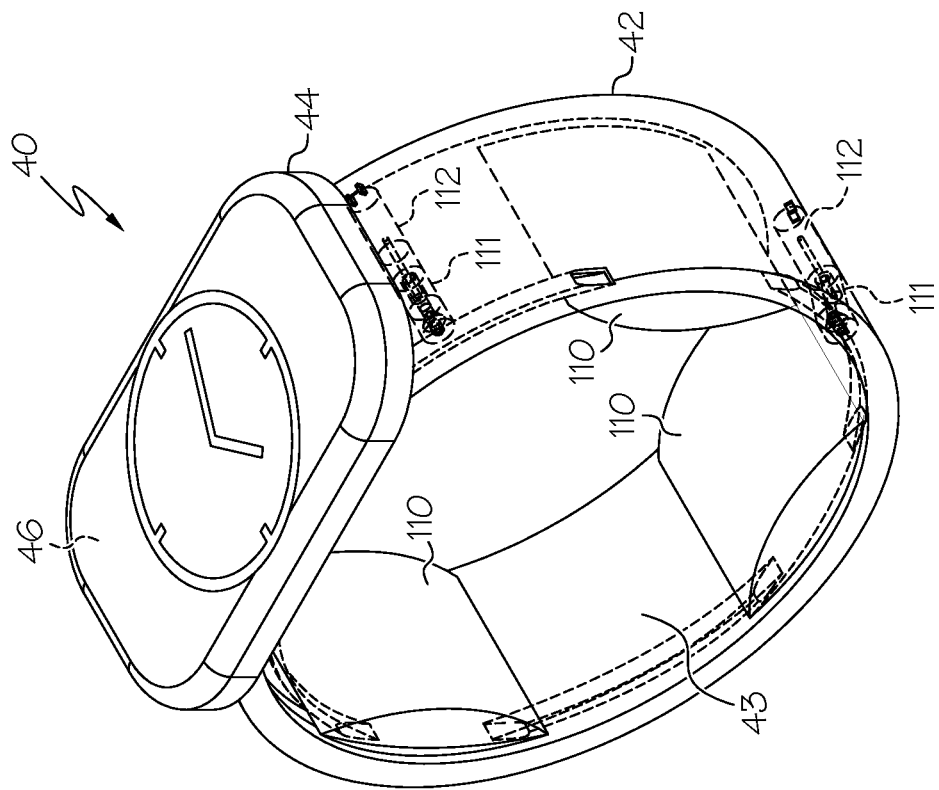
Figure 19C:
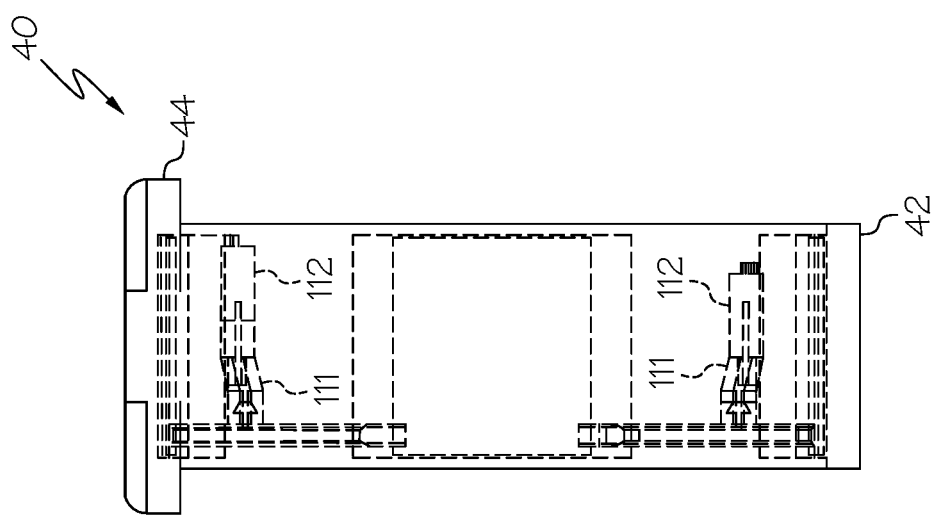
Figure 19E:
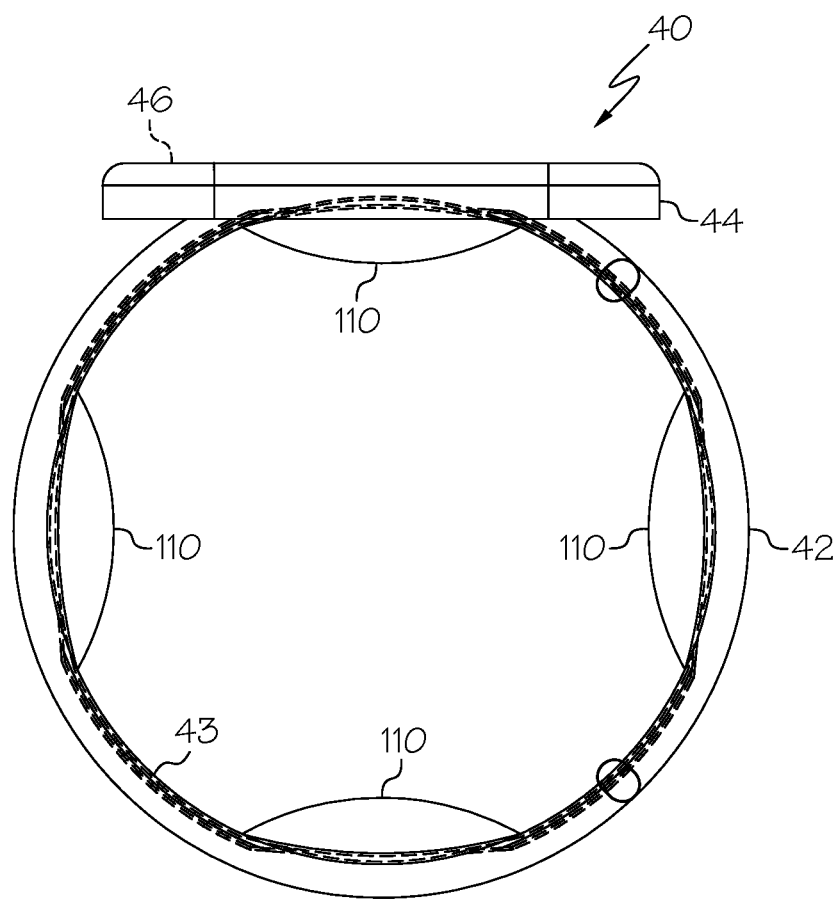
Figure 19F:
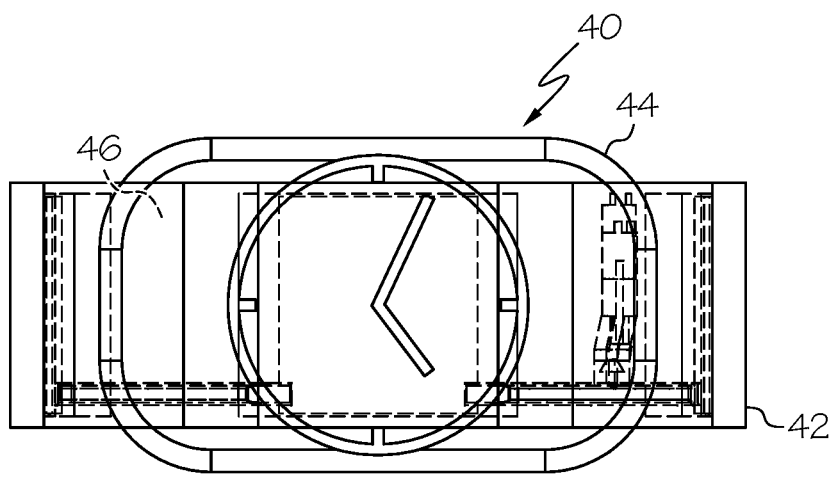

The bladders 110 are expanded via a gas or fluid from a source, such as a source within the housing 44 of the monitoring device/watch 40. One or more pumps 111 and valves 112 (FIGS. 19C, 19D) are utilized to facilitate expansion and contraction of the bladders 110. The one or more pumps 111 and valves 112 may be operated via electrical power from a power source within the monitoring device/watch 40. FIGS. 19A and 19B illustrate the bladders 110 in a deflated configuration and FIGS. 19D and 19E illustrate the bladders 11 in an inflated configuration. When in the inflated configuration, the bladders 110 cause the band 42 to fit snugly around an arm of a subject.

FIG. 20 is a block diagram of an autonomous wearable actuation system 200, according to some embodiments of the present invention. The system 200 may be used with one or more wearable devices and/or wearable device networks having at least one sensor 202 (e.g., physiological sensors, environmental sensors, motion sensors, etc.), processor 204, and at least one actuator 206 in communication with each other. An actuator 206 may include, for example, actuators 26, 36, 50, 110 illustrated in FIGS. 2E-2H, 3B, 5A-5D, 6A-6D, 7A-7C, 8A-8E, 9A-9B, 10A-10E, 11A-11E, 12A-12B, 13A-13G, 14A-14B, 15A-15E, 16A-16E, 17A-17B, 18A-18E, and 19A-19F. In some embodiments, the system 200 may also include a memory 208 for storing various algorithms and also include an analysis platform 210 for analyzing data generated by the processor(s) 204 to generate assessments based on the data. An analysis platform 210 may be in communication with the processor(s) 204 and a memory storage location 200 for the algorithms. An analysis platform 210 may be within a wearable device (e.g., monitoring devices) or may be part of a remote system in wireless or wired communication with the wearable device. An analysis platform 210 may analyze vital sign data (such as heart rate, respiration rate, blood pressure, etc.) in context of the user's activity data (cadence, speed, acceleration, position, etc.) to assess a health or fitness status of the person, such as a health or fitness score. In some embodiments, an analysis platform 210 may process actuation data from the wearable device to determine rules for better actuation on the person and then may update algorithms in the memory location 200. For example, an analysis platform 210 may learn that better physiological signal quality is attained at a certain actuation level (for example, by processing physiological or accelerometry signals from the device and determining a high signal-to-noise ratio exists at a certain actuation level), and then may adjust algorithms accordingly to set a new level of actuation in the wearable device.

The autonomous actuation system 200 may also be in communication with a user interface 212. The user interface 212 may be part of a wearable device itself, a remote device 214, or a distributed between the wearable device and the remote device 214. Examples of user interfaces may include, but are not limited to, audio, visual, touchscreen, haptic (vibrational), gestural, intuitive, mental (such as EEG, for example), biometric (such a biofeedback), mechanical (such as push-button, flip-switch, etc.), or the like.

In some embodiments, elements of the system 200 may be embedded within a wearable biometric device (such as an earbud, headset, hearing aid, armband, wristband, legband, ring, necklace, jewelry, clothing, shoe, sock, glasses, shades, or any other wearable device form-factor). In other embodiments, some elements of system 200 may not be in a wearable device but may rather be distributed in a network, such as the internet, the cloud, a remote device/system 214, a wired processing device, and the like. For example, an environmental sensor 202 may be on a wearable device and/or may be part of a remote device/system 214 in communication with the wearable device, such as a stationary sensor-laden tower or building within a wireless network. Location information, for example from a location sensor 218, may be used to determine the environmental exposure of the person in such case, as the person may be found to be near a region where a fixed environmental sensor is sensing the environment. As a specific example, a person may be standing near an EPA (U.S. Environmental Protection Agency) tower that is measuring air quality, and the processor(s) 204, in remote communication with the EPA tower, may determine that a wearable device must be actuated to allow more breathability or comfort in the wearable device for that particular EPA tower humidity reading. Because the wearable device may be connected to remote systems in a network, location information may be generated and an actuation response may be triggered accordingly, in real-time.

Notwithstanding the foregoing, according to embodiments of the present invention, at least one actuator (e.g., actuators 26, 36, 50, 110, etc.), whether manual or autonomous, is integrated within a wearable device so that a physical adjustment may be made to the wearable device.

The autonomous actuation system 200 may be employed in numerous ways, employing all or portions of the system 200 as described above. For example, readings from sensor(s) 202 can be used to trigger actuation events. Sensor signals may be processed and the processed output may be used to control an actuation event and/or control a biometric signal extraction method. For example, elevated physical activity sensed by an accelerometer may trigger an actuator to move a PPG sensor module (or other sensor module/sensor) towards the skin or away from the skin of a subject wearing a wearable device, etc.

Alternatively or additionally, elevated physical activity may trigger a change in the signal extraction algorithm for PPG towards one of higher acuity (but higher power usage); then, when activity winds down, the algorithm may change to one that is lower acuity (but lower power usage). In this way, battery power is preserved for use cases where high acuity is not needed (such as sedentary behavior where motion artifacts need not be removed.) In other embodiments, the output of a processor 204 or analysis platform 210, in response to processing one or more sensor readings, may trigger an actuation event. For example, a processor 204 may employ a monitoring algorithm to determine if at least one sensor output is within a certain range or to process one or more sensor outputs and calculate a processed output that will trigger an actuation event. As a specific example, the processor 204 may process motion information from a motion (inertial) sensor 202 and/or heart rate information from a heart rate sensor 202 to determine that the user is executing a strength training exercise (for example, by implementing machine learning algorithms developed to characterize strength training based on heart rate and motion information). In such case, a particular amount of tension may be required for the wearable device against the body of the user, and an actuation event may be triggered accordingly.

In other embodiments, data collected over a period of time may be analyzed by an analysis platform 210, and personalized trends may be generated about the person and about other persons in a network who are wearing biometric devices. The trends generated by the analysis platform 210 may then be employed to trigger an actuation event. As a specific example, the analysis platform 210 may be in the cloud (internet based, for example), and long-term biometric signal confidence (signal quality) data or assessments may be generated for one or more physical exercises. The type of exercise (e.g., running, walking, weight lifting, swimming, etc.) may be determined by user input into a network or by autonomous processor calculations based on motion and/or biometric data, for example. The analysis platform 210 may generate a trend showing that a particular exercise always exhibits a low biometric signal quality for a particular person, and this may trigger an actuation event to improve stability of a wearable device worn by the person when such exercise or similar exercises are taking place (as input by the user or autonomously detected, for example). Similarly, the analysis platform 210 may have trends stored for several users wearing a similar type of biometric device, and this aggregated information may be used to generate a generalized trend showing that a particular exercise or activity typically generates low biometric signal quality. This generalized trend may then be used to trigger an actuation event when the user is engaged in that particular (or in a similar) exercise or activity. Ways of generating signal quality scores are described in copending U.S. patent application Ser. No. 14/807,061 filed Jul. 23, 2015, which is incorporated herein by reference in its entirety.

The autonomous actuation system 200 may be employed in numerous ways. As a specific example, the ratcheting actuator 50 of FIG. 13G may be especially well-suited for a biometric wristband, leg band, or armband. As a specific example, a wristband (e.g., 42, FIGS. 5A-5D) embedded with the ratcheting actuator 50 of FIG. 13G may be worn during everyday life activities, and then, during or before exercise use, the actuator 50 may be unwound to facilitate moving the band 42 up along the forearm or upper arm, and then rewound to be stable along these locations. The reasoning for moving the band 42 up along the arm during exercise is that motion artifacts from the wrist may be too intense during the exercise, but not along the forearm or upper arm, where the ratio of pulsatile blood flow to motion noise (the signal-to-noise ratio) is substantially higher. Thus a biometric sensor 202, such as a PPG sensor for example, may sense cleaner biometric information along these locations than for the wrist. However, during everyday life activities, where motion noise may be low, a user wearing a biometric monitoring device with a band 42 may prefer that band 42 be located at the wrist. In a specific embodiment, a biometric sensor 202 or other sensor 202 associated with the band 42 may provide information about the biometric signal confidence (a signal-to-noise indication), and in such case, the autonomous actuation system 200 of FIG. 20 may be employed to notify the user that the ratcheting actuator 50 should be adjusted to move the band 42 higher up the arm.

Alternatively, the system 200 of FIG. 20 may be employed to automatically adjust an actuator ratcheting mechanism (e.g., 50, FIG. 13G) to improve stability, leveraging confidence information. This may be implemented in a feedback loop such that low confidence results in higher stability and high confidence results in lower stability, unless the confidence in the biometric signal quality has a value within an acceptable range for accurate measurement without compromising user comfort. In some embodiments. This same methodology may be employed for earbuds, rings, necklaces, eyewear, clothing (apparel), and other devices built with biometric sensors and actuators. Biometric signal quality is described in U.S. Provisional Patent Application No. 62/110,655 (Attorney Docket No. 9653-30PR2) filed Feb. 2, 2015, which is incorporated herein by reference in its entirety.

It should be noted that the terms "confidence" and "signal quality" may often be used interchangeably herein. However, there are some slight differences between these two terms. Whereas "signal quality" relates primarily to the signal-to-noise ratio of a sensor reading, "confidence" relates primarily to an assessment based on "signal quality". For example, a high signal quality of a given threshold value may correspond with a 100% confidence threshold, such that sensor readings or sensor biometrics associated with signal qualities higher than the threshold value may be assumed to be accurate with a probability of 100%.

In another example, the autonomous actuation system 200 of FIG. 20 may be used to help a user determine presets (such as defaults or customized settings for one or more users) for comfort and accuracy. A wearable device with at least one biometric sensor 202 and actuator 206 may be adjusted for comfort and/or accuracy by the user, either manually and/or autonomously. A preset may be stored within the system 200 such that every time a user puts on a wearable device according to embodiments of the present invention, the wearable device automatically actuates to the appropriate stability for the user. An autonomous preset can be achieved using the system 200 because the processor(s) 204 may be configured to process an algorithm that determines comfort and/or biometric signal quality by processing signals from the associated sensors 202. For example, the processor(s) 204 may determine that the biometric signal quality falls within a suitable range for desired biometric accuracy but that the wearable device is too tight for a comfortable fit, and then an actuation event may be triggered to reduce the stability of the wearable device until comfort is achieved while signal quality is still within an acceptable range. Once comfort and accuracy is satisfactorily achieved, the processor(s) 204 may store the determined "preset settings" in memory.

Alternatively, the user may use one or more user interfaces 212 to acknowledge that the wearable device stability is comfortable, and the processor(s) 204 may determine that biometric signal quality is satisfactory for this stability setting, thereby not triggering an actuation event, or the processor(s) 204 may determine that the biometric signal quality is not satisfactory, thereby notifying the user to change the stability for a repeat stability assessment.

In some embodiments, the actuation system 200 may be used to improve the stability of a wearable device for gestural control. Namely, the processor(s) 204 and/or analysis platform 210 may determine whether the stability of the wearable device is sufficient for adequate gesture recognition. Numerous types of sensors 202 for sensing gesture may be used for sensing motion of the body, as several types of sensors may be configured for measuring fluctuations in matter over time. As a specific example, a wearable device may have sensors 202 for measuring electromagnetic scatter from the body (e.g., using an electromagnetic emitter and electromagnetic detector, such as an optical emitter & detector for example), inertial changes in the body (e.g., using a MEMS device, such as an accelerometer, for example), or electrical signals from the body (as with electromyography or galvanometric readings). The processor(s) 204 may process these sensor inputs to determine if the signal quality is high enough for appropriate gestural recognition (such as detecting head or limb motions, for example). If the signal quality is found to not be sufficient, the system 200 may generate an actuation event to improve the stability of the wearable device against the body. Once stability is determined to be satisfactory, then the actuation event may cease to establish the appropriate stability.

In another embodiment, the user themselves may determine whether the gestural control is satisfactory—perhaps by noting the motion of a cursor on a screen, for example, in response to eye motions for limb motions. The user may then input to the system 200, using a user interface 212, that the stability is satisfactory, thereby establishing a preset stability setting as described previously, which may then be stored in memory 208 for future use such that stability is automatically adjusted for satisfactory gestural control in the future.

In some embodiments, the system 200 may be used to actuate a particular sensor mechanism rather than stabilizing the entire wearable device. As a particular example, and actuation event may trigger the automatic focusing of an optical lens or camera (such as a CCD imager), the movement or placement of optical elements of a PPG sensor, or the automatic adjustment of an optical pattern to be shown against the skin of a person during PPG. For example, the processor(s) 204 may read PPG signals from a PPG sensor 202 to assess signal quality as the PPG sensor optics are actuated. Once the processor(s) 204 determines the actuation range for satisfactory PPG readings, this information may be stored in memory 208 for a preset value as described earlier. Additionally or alternatively, the processor(s) 204 may also select a region between the range of acceptable actuation, such a the midpoint for example, and then send a command to actuate the PPG sensor 202 to the midpoint setting. Though this particular example has been directed towards PPG sensing, this direction should not be construed to limit the invention to actuation of sensor mechanisms that are PPG-related, such as with bioimpedance or body thermography.

As another specific example, an auscultatory sensor 202 may be actuated according the invention as well, to help better couple the acoustic energy from the body with the auscultatory sensor 202. There are many examples of how sensors 202 may be actuated including, but not limited to, changes in sensor placement, changes in sensor position with respect to the body, changes in sensor impedance, changes in sensor stability with respect to the body, changes is audio coupling between the auscultatory sensor and the body, and the like. Similarly, the actuation event may be used to change the position of electrodes near the body. For example, the electrodes may be positioned to be more or less stable along the body or be positioned to have closer or farther spacing between each other.

In some embodiments of the present invention, an "actuation event" may not involve a physical actuation. For example, an "actuation event" may relate to a change in sensor impedance, as with a processing step directed to change the sensor impedance in response to a low-signal-quality. As a particular example, in the case of bioimpedance sensing, as with electrodes 202 located along the skin, the system 200 may determine that the electrode readings exhibit unsatisfactory signal quality, and the processor(s) 204 may send a signal to adjust the impedance of electrodes to a value where signal quality is determined to be satisfactory.

In some embodiments, the system 200 may be used to actuate another device other than the wearable device, such as a remote device. As an example, the system 200 may monitor and/or record sleeping patterns and/or sleeping quality via sensors 202 on a wearable device. The system 200 may also receive sensor readings, such as temperature or humidity readings, from a remote device such as a thermostat (such as a wireless "smart thermostat"). The system 200 (e.g., either the processor(s) 204 and/or the analysis platform 210) may then process a history of sleeping patterns and/or sleeping quality in context of the environmental conditions (such as temperature, humidity, pressure, etc.) to generate an analysis of which environmental settings generally lead to better sleep quality and/or sleeping patterns. As a specific example, the heart rate variability (HRV) of a person donning a wearable sensor device during sleep may be analyzed to generate an assessment of sleep quality. The wearable device could be a wristband, earplug or earpiece, patch, armband, headband, ring, or numerous other form-factors. An example of good sleep quality in terms of HRV vs. time is presented in FIG. 21A, and an example of bad sleep quality in terms of HRV vs. time is presented in FIG. 21B. It should be noted that a rhythmic behavior of alternating high and low HRV is observed for a subject reporting good sleep quality; in contrast, a less rhythmic HRV is observed for a subject reporting bad sleep quality. The processor(s) 204 or analysis platform 210 may process one or more nights of sleep quality by assessing the HRV pattern and generating a sleep quality score. In some embodiments, this may be accomplished by implementing an autocorrelation function on a given night's sleep to help generate a score for the rhythmic pattern of a person's sleep during a particular night.

As shown in FIG. 22, this score may be then be analyzed and/or plotted by the analysis platform 210 (FIG. 20) in context with the associated environmental conditions, (such as temperature or a combination of temperature and humidity, for example), and the analysis platform 210 may then determine which environmental conditions are associated with the best likelihood of high sleep quality. This analysis results may then trigger an actuation event to the subject's thermostat such that the person's room temperature is adjusted to the most optimal settings for a good night's sleep. Because a person's optimal settings may change over time, this analysis-actuation process may adapt with the user over time. As shown in FIG. 22, the analysis-actuation method described, though exemplified through the sleep quality example, may be more broadly applied to any biometric status quality vs. an environmental exposure condition.

For example, an assessment of overall cardiovascular fitness in context of air pollution quality may be assessed using this method. In such an embodiment, a wearable device may comprise a fitness sensor 202 (such as a PPG or ECG sensor) and a remote system may be an air pollution monitor, such as that mounted on an EPA tower or in a home or building.

In yet another embodiment of the analysis-actuation system 200 of FIG. 20, the analysis platform may analyze biometric sensor data from a wearable device, such as a device comprising vital signs sensors 202 (heart rate, respiration rate, blood pressure, HRV and the like) in context of sensed light exposure, via at least one light exposure sensor 202 which may be in the wearable device or another wearable or portable device. The system 200 may then run an algorithm to determine if the subject is receiving adequate light exposure by evaluating one or more vital signs in context of the subject's light exposure. Optimum lighting conditions may be determined, and then the system 200 may trigger an actuation to one or more lights or lighting systems that are in communication with the system of FIG. 21 such that the subject's optimum light exposure is realized.

In the aforementioned cases comprising optimizing environmental exposures in context of biometric sensor information, it may be difficult for a subject to have optimum settings of environmental exposure throughout the day. This may be further complicated with multiple subjects using the same system 200 for environmental exposure, as one subject's optimum exposure conditions (such as the optimal amount of sun exposure or optimal amount of outdoor air) may not be closely matched to that of another subject using the system 200. For this reason, the system 200 may comprise an algorithm for normalizing the optimum conditions of users within the system. For example, the algorithm may take the average of the optimum conditions of subjects using the system 200, or the algorithm may identify common critical environmental exposure conditions that are required for each subject to have a sufficient biometric status quality. Then the system 200 may send an actuation event to normalize remote devices for the group of multiple subjects accordingly to be in line with these conditions (i.e., the averaged conditions or identified critical conditions). In the case where it is impossible for the subject to receive sufficient dosing of environmental exposure conditions within the system 200, then the user may be notified via a user interface 212 (such as one on a wearable device or a remote device) to move to a location where the user can receive the appropriate dose. In order to execute this feature, the system 200 has access to the user's location, which may be provided via several methods, such as GPS (on a wearable device or with a portable communication device), Wi-Fi location detection, or other location network methods that are able to interface with an electronic system.

Example embodiments are described herein with reference to block diagrams. It is understood that a block of the block diagrams, and combinations of blocks in the block diagrams, can be implemented by computer program instructions that are performed by one or more computer circuits, such as electrical circuits having analog and/or digital elements. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams, and thereby create means (functionality) and/or structure for implementing the functions/acts specified in the block diagrams.

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-eRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams. Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that the functionality of a given block of the block diagrams may be separated into multiple blocks and/or the functionality of two or more blocks of the block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A monitoring device configured to be attached to a body of a subject, the monitoring device comprising:
    at least one physiological sensor configured to detect and/or measure physiological information from the subject;
    at least one activity sensor configured to sense physical activity information from the subject;
    at least one actuator configured to adjust stability of the monitoring device relative to the body of the subject; and
    at least one processor in communication with the at least one activity sensor and the at least one actuator, wherein the at least one processor is configured to process the physical activity information to detect a change in a physical activity of the subject and to control the at least one actuator to adjust the stability of the monitoring device relative to the body of the subject in response to detecting that the change in the physical activity of the subject has occurred.

2. The monitoring device of claim 1, wherein the at least one processor controls the at least one actuator to increase the stability of the monitoring device relative to the body of the subject in response to detecting an increase in the physical activity of the subject, and wherein the at least one processor controls the at least one actuator to decrease the stability of the monitoring device relative to the body of the subject in response to detecting a decrease in the physical activity of the subject.

3. The monitoring device of claim 1, wherein the at least one processor is further configured to detect a change in the physical activity of the subject by detecting a change in at least one subject vital sign detected and/or measured by the at least one physiological sensor, wherein the at least one subject vital sign includes subject heart rate, subject blood pressure, subject temperature, subject respiration rate and/or subject perspiration rate.

4. The monitoring device of claim 1, wherein the at least one processor is further configured to detect a change in the physical activity of the subject by identifying or predicting a type of activity.

5. The monitoring device of claim 1, wherein the at least one activity sensor comprises a motion sensor.

6. The monitoring device of claim 1, wherein the at least one actuator comprises one or more of the following: at least one bladder that is expandable and retractable, a material that changes shape in response to an application of light and/or heat thereto, a material that undergoes a phase change in response to a change in temperature, a conductive material that changes shape in response to an application of electrical current thereto, at least one electromechanical actuator.

7. The monitoring device of claim 1, wherein the monitoring device is configured to be positioned at or within an ear of the subject, and wherein the at least one actuator is configured to adjust the stability of the monitoring device relative to a portion of the ear of the subject.

8. The monitoring device of claim 1, wherein the monitoring device comprises a band configured to be secured to an appendage of the subject, and wherein the at least one actuator is configured to adjust the stability of the monitoring device relative to a portion of the appendage of the subject.

9. The monitoring device of claim 8, wherein the at least one actuator is configured to adjust tension of the band around the appendage of the subject.

10. The monitoring device of claim 8, wherein the band comprises an electroactive polymer material, a thermoactive material, or a piezoactive material.

11. The monitoring device of claim 1, wherein the at least one physiological sensor comprises at least one optical emitter and at least one optical detector.

12. A method of monitoring a subject via a monitoring device, wherein the monitoring device includes at least one physiological sensor configured to detect and/or measure physiological information from the subject, at least one activity sensor configured to sense physical activity information from the subject, at least one actuator configured to adjust stability of the monitoring device relative to a body of the subject, and at least one processor in communication with the at least one activity sensor and the at least one actuator, the method comprising:
    detecting and/or measuring physiological information from the subject via the at least one physiological sensor;
    detecting a change in a physical activity of the subject by processing, via the at least one processor, physical activity information sensed by the at least one activity sensor; and
    controlling the at least one actuator, via the at least one processor, to adjust the stability of the monitoring device relative to the body of the subject in response to detecting a change in the physical activity of the subject.

13. The method of claim 12, wherein controlling the at least one actuator comprises controlling the at least one actuator to:
    increase the stability of the monitoring device relative to the body of the subject in response to detecting an increase in the physical activity of the subject; and
    decrease the stability of the monitoring device relative to the body of the subject in response to detecting a decrease in the physical activity of the subject.

14. The method of claim 12, further comprising detecting a change in the physical activity of the subject by detecting, via the at least one processor, a change in at least one subject vital sign sensed by the at least one physiological sensor, wherein the at least one subject vital sign includes subject heart rate, subject blood pressure, subject temperature, subject respiration rate, and/or subject perspiration rate.

15. The method of claim 12, wherein the at least one activity sensor comprises a motion sensor.

16. A method of monitoring a subject via a monitoring device, wherein the monitoring device comprises an actuator configured to adjust stability of the monitoring device, the method comprising:
    collecting physiological data from a physiological sensor worn by the subject;
    collecting physical activity data from an activity sensor worn by the subject;

processing the collected physical activity data and the physiological data via at least one processor to detect a change in a physical activity of the subject; and controlling the actuator via the at least one processor to adjust the stability of the monitoring device relative to a body of the subject in response to detecting a change in the physical activity of the subject.

17. The method of claim 16, wherein controlling the actuator comprises controlling the actuator to:

increase the stability of the monitoring device relative to the body of the subject in response to detecting an increase in the physical activity of the subject; and decrease the stability of the monitoring device relative to the body of the subject in response to detecting a decrease in the physical activity of the subject.

18. The method of claim 16, wherein the activity sensor comprises a motion sensor.

* * * * *